(12) United States Patent
Iyer et al.

(10) Patent No.: US 11,109,965 B2
(45) Date of Patent: Sep. 7, 2021

(54) TRANSCATHETER HEART VALVE PROSTHESIS ASSEMBLED INSIDE HEART CHAMBERS OR BLOOD VESSELS

(71) Applicant: Laplace Interventional Inc.

(72) Inventors: Ramji Iyer, Maple Grove, MN (US); Stephen Anderson, Minneapolis, MN (US); Samuel Thomas Johnson, Maple Grove, MN (US)

(73) Assignee: Laplace Interventional Inc., Plymouth, MN (US)

( * ) Notice: Subject to any disclaimer, the term of this patent is extended or adjusted under 35 U.S.C. 154(b) by 0 days.

(21) Appl. No.: 17/165,244

(22) Filed: Feb. 2, 2021

(65) Prior Publication Data
US 2021/0244535 A1     Aug. 12, 2021

Related U.S. Application Data

(60) Provisional application No. 63/130,201, filed on Dec. 23, 2020, provisional application No. 62/970,967, filed on Feb. 6, 2020.

(51) Int. Cl.
*A61F 2/24*      (2006.01)

(52) U.S. Cl.
CPC .......... *A61F 2/2418* (2013.01); *A61F 2/2436* (2013.01)

(58) Field of Classification Search
CPC .. A61F 2/24; A61F 2/07; A61F 2/2418; A61F 2/2409; A61F 2/2469; A61F 2/2412; A61F 2/82; A61F 2/86; A61F 2/246; A61F 2/06; A61F 2/2436
See application file for complete search history.

(56) References Cited

U.S. PATENT DOCUMENTS

| | | | |
|---|---|---|---|
| 9,393,110 B2 | 7/2016 | Levi et al. | |
| 9,579,196 B2 | 2/2017 | Morriss | |
| 9,681,951 B2 | 6/2017 | Ratz et al. | |
| 10,213,307 B2 | 2/2019 | Dwork et al. | |
| 10,321,995 B1 | 6/2019 | Christianson | |
| 10,583,000 B2 | 3/2020 | Ratz | |
| 10,779,936 B2 | 9/2020 | Pollak | |
| 2005/0149181 A1 | 7/2005 | Eberhardt | |
| 2007/0055356 A1* | 3/2007 | Eidenschink | A61F 2/958 623/1.25 |
| 2010/0023046 A1* | 1/2010 | Heidner | A61B 17/12036 606/191 |

(Continued)

FOREIGN PATENT DOCUMENTS

WO    WO 2015/052570    4/2015

OTHER PUBLICATIONS

Invitation to Pay Additional Fees in International Application No. PCT/US2021/016150, dated Apr. 6, 2021, 2 pages.

(Continued)

*Primary Examiner* — Seema Mathew
(74) *Attorney, Agent, or Firm* — Fish & Richardson P.C.

(57) ABSTRACT

Some embodiments described herein include a heart valve replacement system that may be delivered to the targeted heart valve site via a delivery catheter. In some embodiments, the heart valve replacement system can assemble a valve device after the valve device is delivered to the heart. In some embodiments, heart valve replacement system includes two anterior flaps that are separate but overlap each other.

22 Claims, 45 Drawing Sheets

(56) References Cited

U.S. PATENT DOCUMENTS

| | | | | |
|---|---|---|---|---|
| 2010/0316830 A1* | 12/2010 | Hartley | ..................... | A61F 2/07 |
| | | | | 428/64.1 |
| 2014/0277390 A1 | 9/2014 | Ratz | | |
| 2015/0216653 A1* | 8/2015 | Freudenthal | .............. | A61F 2/90 |
| | | | | 623/2.17 |
| 2017/0325945 A1* | 11/2017 | Dale | ..................... | A61F 2/2418 |
| 2018/0000586 A1 | 1/2018 | Ganesan | | |
| 2019/0008636 A1* | 1/2019 | Francis | ................. | A61B 5/068 |
| 2020/0179109 A1 | 6/2020 | Reimer | | |
| 2020/0268512 A1 | 8/2020 | Mohl | | |

OTHER PUBLICATIONS

PCT International Search Report and Written Opinion in International Appln. No. PCT/US2021/016150, dated Jun. 29, 2021, 17 pages.

\* cited by examiner

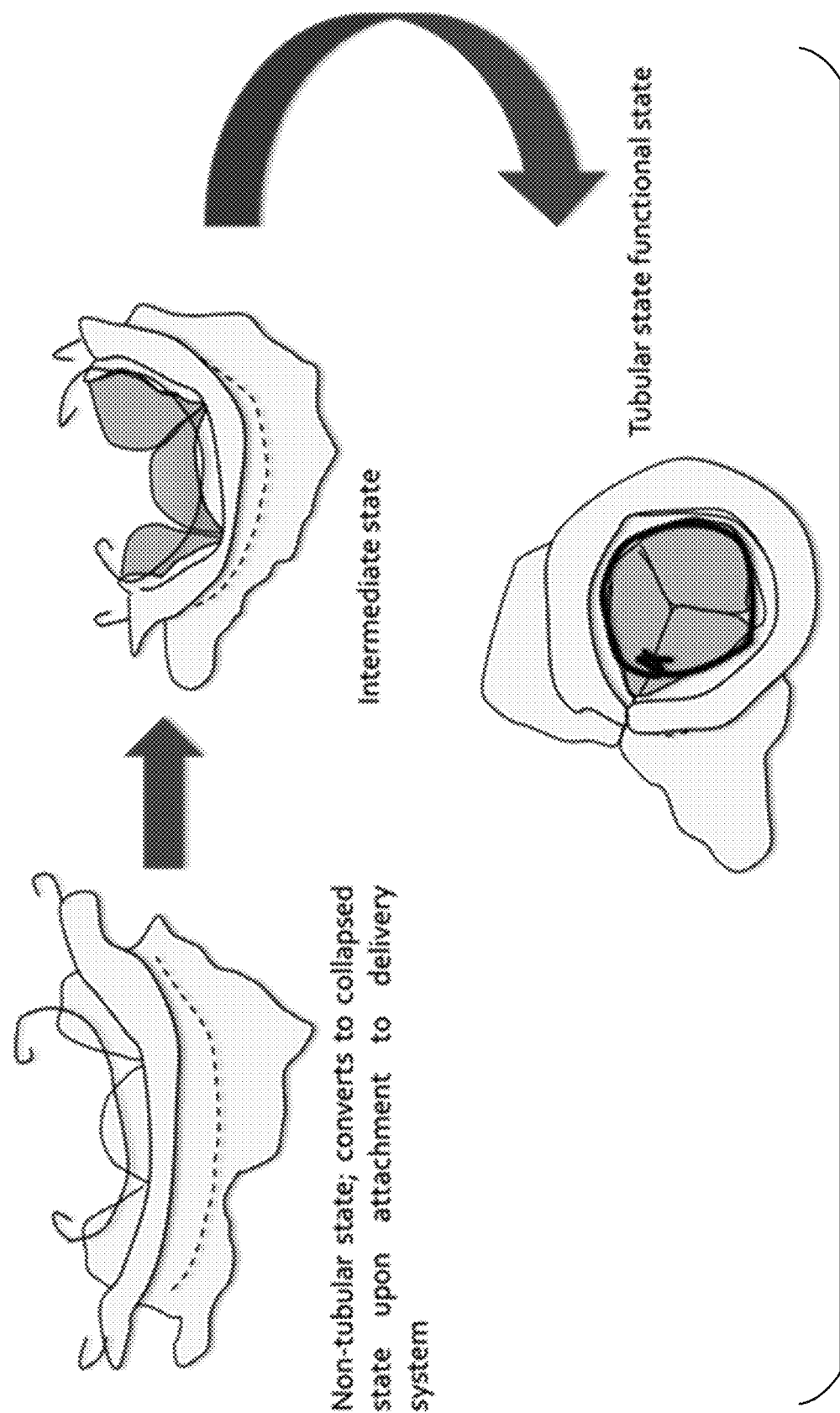

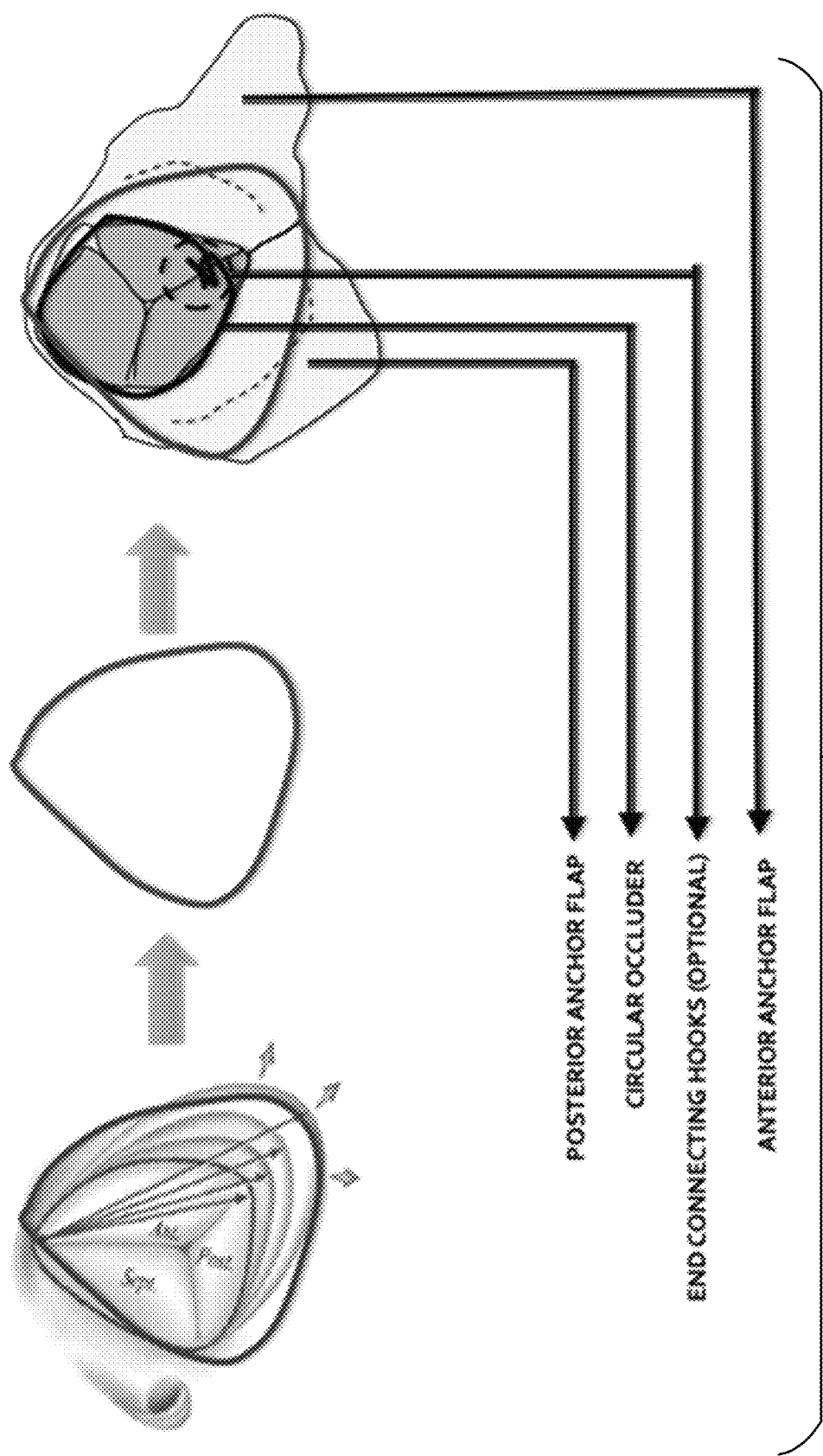

RA – Right Atrium
LA – Left Atrium
RV – Right Ventricle
LV – Left Ventricle
Ao – Aorta
MPA – Main Pulmonary Artery
SVC – Superior Vena Cava
IVC – Inferior Vena Cava

- Trans-Jugular access to RA.
- Float balloon through Tricuspid Annulus.

Balloon to cross tricuspid valve

- Obtain Guidewire access into RV.

- Deflectable Sheath access to RA over Guidewire
- Valve attached to Valve Delivery Catheter and collapsed inside Deflectable Sheath.

Advance Valve Delivery Catheter with Anterior anchoring flap in RV.

- After satisfactory Valve Performance evaluations, Deploy Valve fully by detaching from Delivery Catheter.
- Retract Delivery Catheter into Deflectable Sheath.

- Retract Guidewire into Deflectable Sheath.

- Retract Deflectable Sheath.
- Close Vessel access site.

- Retract the Outer Proximal Catheter and Inner Distal Catheter into the Sheath

- Retract Guidewire into Sheath.

- Remove Sheath

TRANSCATHETER HEART VALVE PROSTHESIS ASSEMBLED INSIDE HEART CHAMBERS OR BLOOD VESSELS

CROSS-REFERENCE TO RELATED APPLICATIONS

This application claims the benefit of U.S. Provisional Application Ser. No. 62/970,967, filed Feb. 6, 2020, and U.S. Provisional Application Ser. No. 63/130,201, filed Dec. 23, 2020. The disclosures of the prior applications are considered part of (and are incorporated by reference in) the disclosure of this application.

FIELD OF INVENTION

This disclosure generally relates to transcatheter heart valve systems, and more particularly to a valve prosthesis that is adapted to be assembled to a final configuration while the valve prosthesis is located within a target patient's heart chambers or blood vessels. Such a system can be used to replace a sub-optimally functioning native heart valve, including but not limited to a tricuspid valve.

BACKGROUND

A human heart includes four heart valves that ensure blood flow in a specific direction: mitral, tricuspid, aortic and pulmonary valves. The aortic and pulmonary valves are semilunar valves, which are in the arteries leaving the heart; and prevent blood from flowing back into left ventricle and right ventricle respectively when closed. The mitral and tricuspid valves are atrio-ventricular valves, which are between the atria and the ventricles; and prevent blood from flowing back into left atrium and right atrium respectively when closed. Both conditions of stenosis (when valve doesn't open fully) as well as regurgitation/insufficiency (when valve doesn't close properly resulting in leaks) are recognized as significant contributor to mortality and morbidity.

Some valve replacement systems include valve prostheses that are compressed into a delivery catheter, also referred to as transcatheter valves, so as to avoid open heart surgery. Most transcatheter valve prostheses developed have a tubular frame that may or may not be axisymmetric with two or more leaflets. While these transcatheter valve prostheses can be compressed into a catheter, they may still require a large delivery system (for example, a required catheter size of 45 French). This is especially true in case of mitral valve replacement systems and tricuspid valve replacement systems, which often require valve prostheses with a larger foot print.

SUMMARY

Some embodiments described herein include a heart valve replacement system that may be delivered to the targeted heart valve site via a delivery catheter. In particular implementations, the system can include transcatheter valve device that occupies a smaller delivery profile, thereby facilitating a smaller delivery catheter for advancement to the heart. In some optional embodiments, the system includes a transcatheter prosthetic heart valve device that, during the delivery stage, is non-tubular and has two free ends (or "open ends") such that these two free ends can be subsequently attached together or otherwise deployed after delivery inside the patient's body, to thereby form a tubular structure that functions as a heart valve prosthesis. The valve device may achieve a tubular structure, for instance, when it defines a generally tubular path through which blood can flow after deployment of the valve device at or near a targeted native valve site. For example, in some embodiments the two free ends of the valve device can be mechanically connected to one another after the valve device is delivered into a targeted chamber of the heart or at a targeted native valve site in the heart, to form a tubular structure that is anchored at the targeted native valve site to function as a heart valve prosthesis.

In one aspect, this disclosure is directed to a prosthetic tricuspid valve that includes a main body comprising an occluder having valve leaflets, a first anterior flap extending laterally from an end of the main body, and a second anterior flap extending laterally from the end of the main body in a same direction as the first anterior flap. Such a prosthetic tricuspid valve may optionally include one or more of the following features. In some embodiments, portions of the first anterior flap and the second anterior flap overlap each other. The prosthetic tricuspid valve may also include a posterior flap extending laterally from the end of the main body in an opposite direction as the first and second anterior flaps. In some embodiments, the first and second anterior flaps extend farther laterally than the posterior flap. In particular embodiments, the first and second anterior flaps in combination are wider than the posterior flap. A framework of the prosthetic tricuspid valve that comprises the main body, the first and second anterior flaps, and the posterior flap may be made of a single, unitary material that was cut and expanded. In some embodiments, a distal tip portion of the posterior flap extends along an axis that is at a non-zero angle relative to a portion of the posterior flap that extends directly from the main body. In some examples, having the portions of the first anterior flap and the second anterior flap that overlap each other increases a bending resistance of the first anterior flap and the second anterior flap in combination as compared to the the first anterior flap and the second anterior flap individually. Having the portions of the first anterior flap and the second anterior flap as separate members can configure the prosthetic tricuspid valve to have a pacemaker lead pass through the prosthetic tricuspid valve between the first and second anterior flaps. The prosthetic tricuspid valve may also include one or more additional anterior flaps extending laterally from the end of the main body in the same direction as the first and second anterior flaps. The prosthetic tricuspid valve may also include two or more posterior flaps extending laterally from the end of the main body in an opposite direction as the first and second anterior flaps.

A deployment system may be used in combination with the prosthetic tricuspid valve. Such a deployment system may include a sheath catheter defining a first lumen, an outer proximal catheter slidably disposed within the first lumen and defining a second lumen, and an inner distal catheter slidably disposed within the second lumen. The prosthetic tricuspid valve may be disposed within the first lumen in a low profile delivery configuration and may be releasably attached to both the outer proximal catheter and the inner distal catheter. In some embodiments, the the main body is releasably attached to outer proximal catheter, and/or the first and second anterior flaps are releasably attached to the inner distal catheter. The prosthetic tricuspid valve may also include a posterior flap extending laterally from the end of the main body in an opposite direction as the first and second anterior flaps. The posterior flap may be disposed within the first lumen while not being directly attached to the deployment system. In some embodiments, the first and second anterior flaps are individually releasably attached to the inner distal catheter.

In another aspect, this disclosure is directed to a method of deploying a prosthetic tricuspid valve. The method includes advancing the prosthetic tricuspid valve contained within a deployment system toward a native tricuspid valve. The prosthetic tricuspid valve, when unconstrained by the deployment system, can include: (i) a main body comprising an occluder having valve leaflets; (ii) a first anterior flap extending laterally from an end of the main body; (iii) a second anterior flap extending laterally from the end of the main body in a same direction as the first anterior flap; and (iv) a posterior flap extending laterally from the end of the main body in an opposite direction as the first and second anterior flaps. The deployment system can include: (i) a sheath catheter defining a first lumen; (ii) an outer proximal catheter slidably disposed within the first lumen and defining a second lumen; and (iii) an inner distal catheter slidably disposed within the second lumen. The method also includes retracting the sheath catheter relative to the outer proximal catheter and the inner distal catheter. The retracting causes the posterior flap to emerge from being contained within the sheath catheter. The method also includes positioning the posterior flap in a posterior region of a right ventricle and, after the posterior flap is positioned in the posterior region of the right ventricle, releasing the first anterior flap from being attached to the inner distal catheter and releasing the second anterior flap from being attached to the inner distal catheter. The method also includes positioning the first and second anterior flaps in a right ventricular outflow tract (RVOT) of the right ventricle, and after the first and second anterior flaps are positioned in the RVOT, releasing the main body from being attached to the outer proximal catheter.

Such a method of deploying a prosthetic tricuspid valve may optionally include one or more of the following features. The first and second anterior flaps may be released in separate steps from each other. When the first and second anterior flaps are positioned in the RVOT, the first and second anterior flaps may overlap each other. In some embodiments, during the advancing: (i) the first and second anterior flaps are releasably attached to the inner distal catheter using removable sutures, and/or (ii) the main body is releasably attached to the outer proximal catheter using a removable suture.

In another aspect, this disclosure is directed to a method of treating a deficiency of a native tricuspid valve. The method includes implanting a prosthetic tricuspid valve in the native tricuspid valve. The prosthetic tricuspid valve may include: (i) a main body comprising an occluder having valve leaflets; (ii) a first anterior flap extending laterally from an end of the main body; (iii) a second anterior flap extending laterally from the end of the main body in a same direction as the first anterior flap; and (iv) a posterior flap extending laterally from the end of the main body in an opposite direction as the first and second anterior flaps. In some embodiments, the implanting comprises: (i) positioning the posterior flap in a posterior region of a right ventricle, and (ii) positioning the first and second anterior flaps in a right ventricular outflow tract (RVOT) of the right ventricle.

DESCRIPTION OF FIGURES

FIG. 4A depicts the device in a first configuration, FIG. 5A depicts the device in a second (intermediate) configuration, and FIG. 6A depicts the device in a third (deployed) configuration.

FIG. 4B depicts the device in a first configuration, FIG. 5B depicts the device in a second (intermediate) configuration, and FIG. 6B depicts the device in a third (deployed) configuration.

FIG. 4C depicts the device in a first configuration, FIG. 5C depicts the device in a second (intermediate) configuration, and FIG. 6C depicts the device in a third (deployed) configuration.

FIG. 4D depicts the device in a first configuration, FIG. 5D depicts the device in a second (intermediate) configuration, and FIG. 6D depicts the device in a third (deployed) configuration.

FIG. 8B shows the transformation of the second embodiment of the device of FIGS. 4B, 5B, and 6B to a deployed transcatheter tricuspid valve prosthesis device having with anterior and posterior anchoring flaps in their functioning state and having an atrial shelf.

FIG. 9 shows a top view of a tricuspid annulus in a diseased state with the first embodiment of the transcatheter valve prosthesis device (of FIG. *A) deployed in it.

DETAILED DESCRIPTION

1. Description of Transcatheter Valve Replacement System (Valve and Delivery System)

Some embodiments of a heart valve replacement device that may be delivered to the targeted heart valve site via a delivery system are described herein. As detailed below, the system may include a transcatheter prosthetic valve device that is arranged in a non-tubular state during the delivery stage and that is subsequently assembled into a tubular state after it is delivered into the heart. Particular embodiments that can achieve such a beneficial configuration are depicted, for example, in FIGS. 4A-D, 5A-D, 6A-D, and 8A-D, which are described in more detail below.

For example, the transcatheter prosthetic valve device may be configurable/positionable in a first configuration in which two matable ends of the valve device's frame are spaced apart from one another (e.g., during delivery to the heart, e.g., embodiments further described subsequently in connection with FIGS. 17-19), and a second, deployed configuration in which the two matable ends of the frame are joined together so that the frame defines a generally tubular path through which blood can flow (e.g., after deployment within the heart, e.g., embodiments further described subsequently in connection with FIGS. 20-22). During the delivery stage, a first matable end of the two matable ends can be positioned adjacent to a first point along the distal end portion of a catheter, and a second matable end of the two matable ends is positioned adjacent to a second point along the distal end portion of a catheter (the second point being longitudinally/axially spaced apart from the first point along the distal end portion of the catheter). This allows for axial (longitudinal) separation along the length of the prosthetic valve device, for example, by packing the valve device in a non-tubular, helical arrangement during delivery to the heart. In some implementations, this configuration during delivery can advantageously provide a reduced profile during the delivery stage, especially in particular embodiments where only one leaflet of the multiple occluder leaflets of the valve device is compressed against the catheter at any given axial position along the length of the distal end portion of the catheter.

Figure 1:
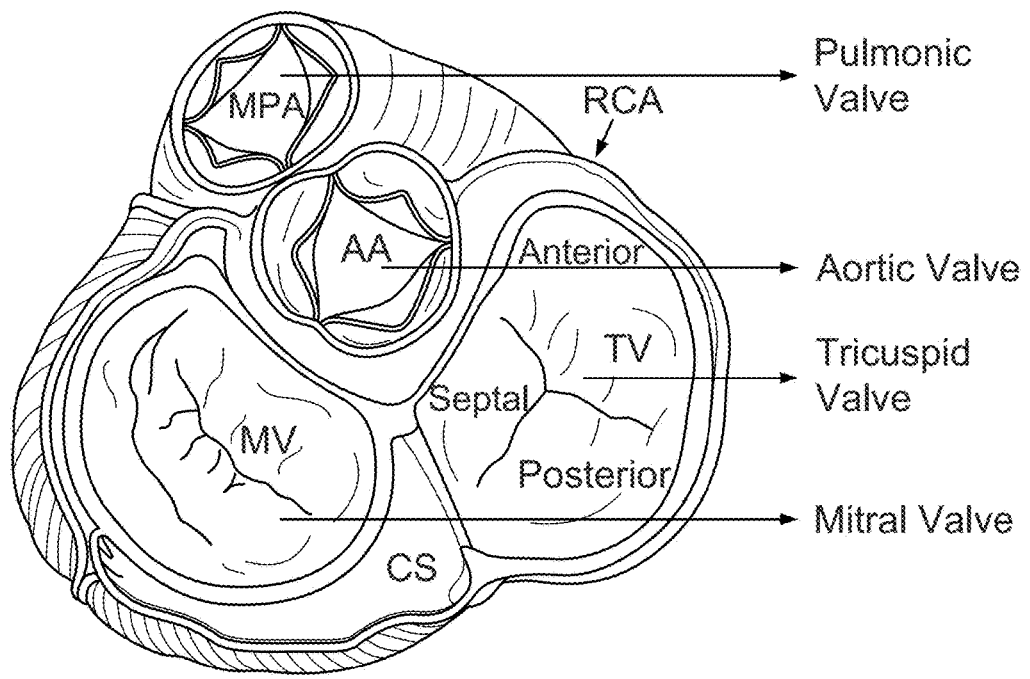
FIG. 1 shows a sectional view of a human heart along with the four heart valves that allow blood flow through a specific pathway: mitral valve, tricuspid valve, aortic valve and the pulmonary valve. The mitral and tricuspid valve may prevent backflow of blood into left atrium and right atrium respectively when the left and right ventricle contract respectively.
Figure 2:
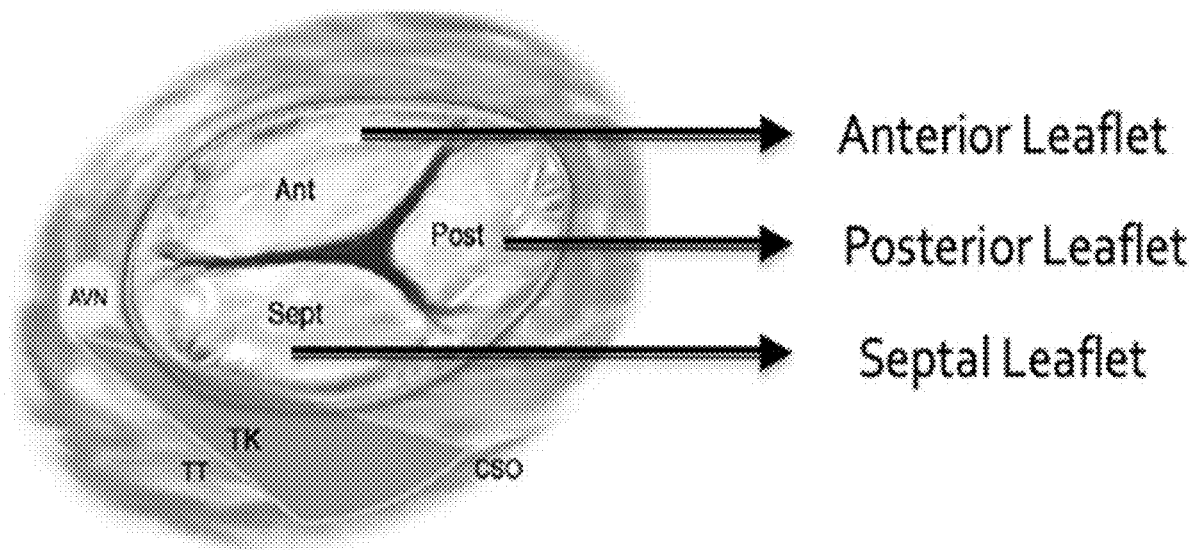
FIG. 2 shows a top view of the tricuspid valve of FIG. 1 having three native leaflets: anterior, posterior and septal.
Figure 3:
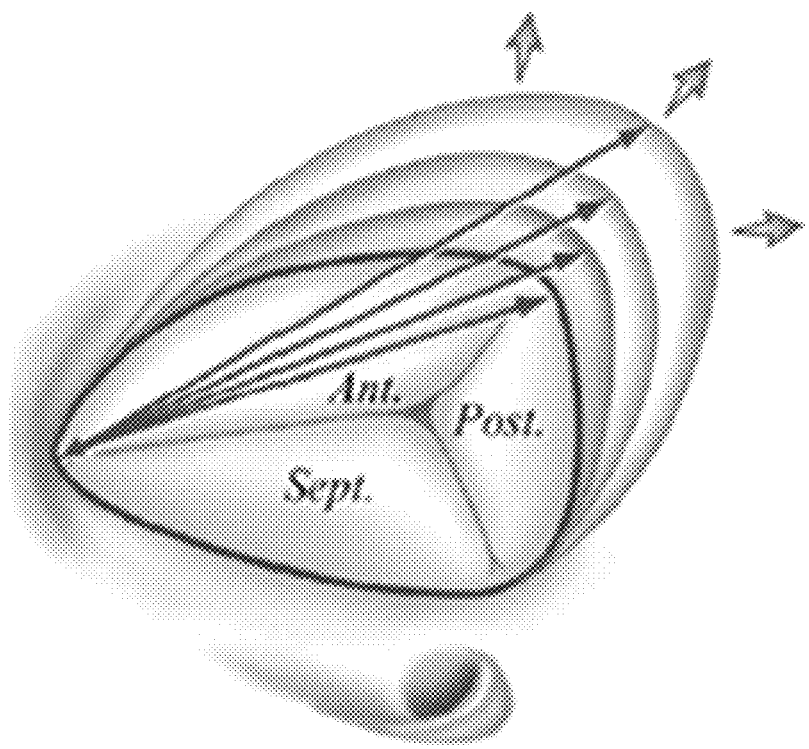
FIG. 3 shows the top view of a tricuspid annulus of FIG. 2, indicating anatomical changes that may be associated with the disease progression during tricuspid regurgitation. For example, the distance between the anterio-septal commissure and the anterio-posterior commissure of the native tricuspid valve may increase with the progression of the diseased state due to dilation of the tricuspid annulus.

Referring to FIGS. 1-3, the concepts described herein for the heart valve replacement system can be implemented for use at any of the four heart valves that allow blood flow through a specific pathway: mitral valve, tricuspid valve, aortic valve and the pulmonary valve. FIG. 2 depicts, for example, a targeted site at a tricuspid valve of the heart. As shown in FIG. 3, in some circumstances, the tricuspid valve may undergo the anatomical changes that cause tricuspid regurgitation, such as instances with the distance between the anterio-septal commissure and the anterio-posterior commissure of the native tricuspid valve increases with the progression of a diseased state due to dilation of the tricuspid annulus.

A. Example Embodiments of a Valve Prosthesis Device for Transcatheter Delivery

Figure 4A:
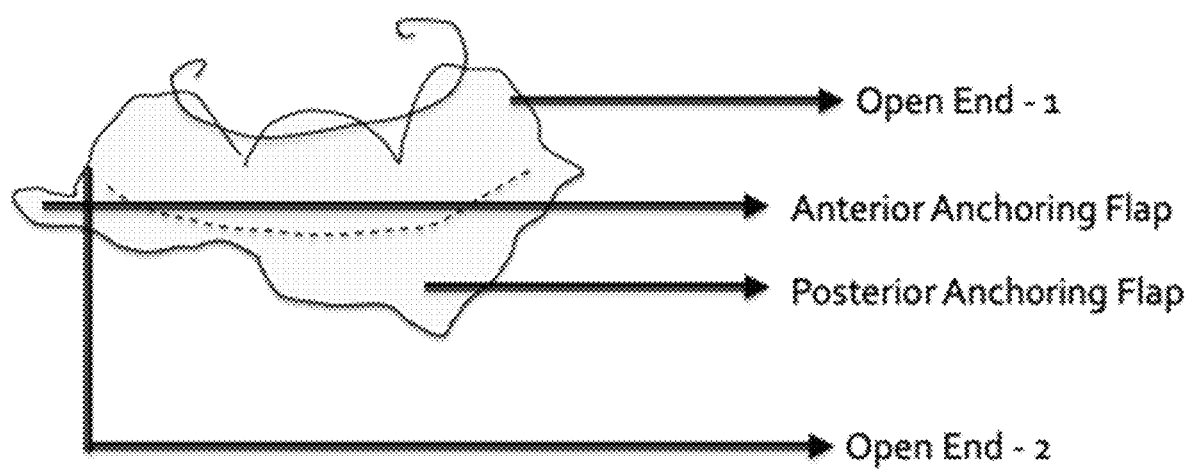
FIGS. 4A, 5A, and 6A shows perspective views of a first embodiment of a transcatheter valve prosthesis device, which can be deployed to replace the tricuspid valve of FIG. 3, in accordance with particular embodiments described herein. The first embodiment depicted in FIGS. 4A, 5A, and 6A is configured without an atrial shelf.
Figure 5A:
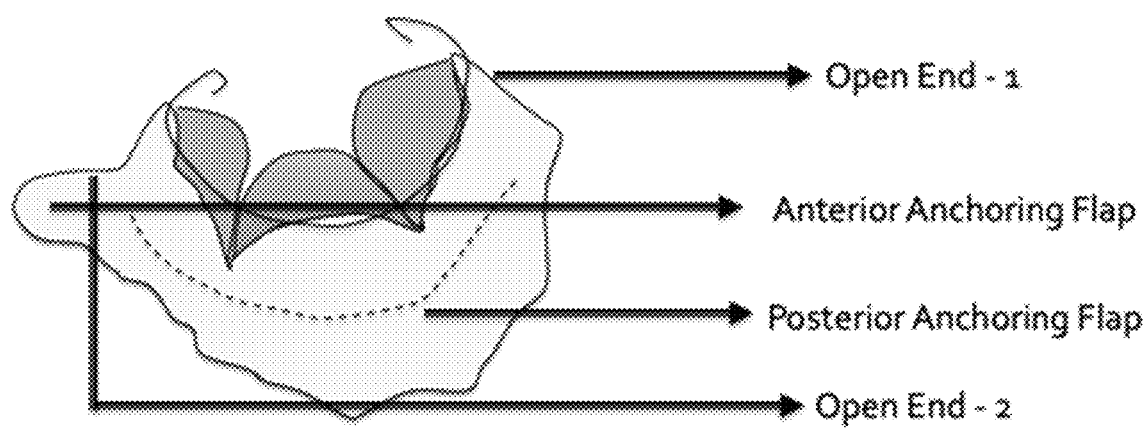
Figure 6A:
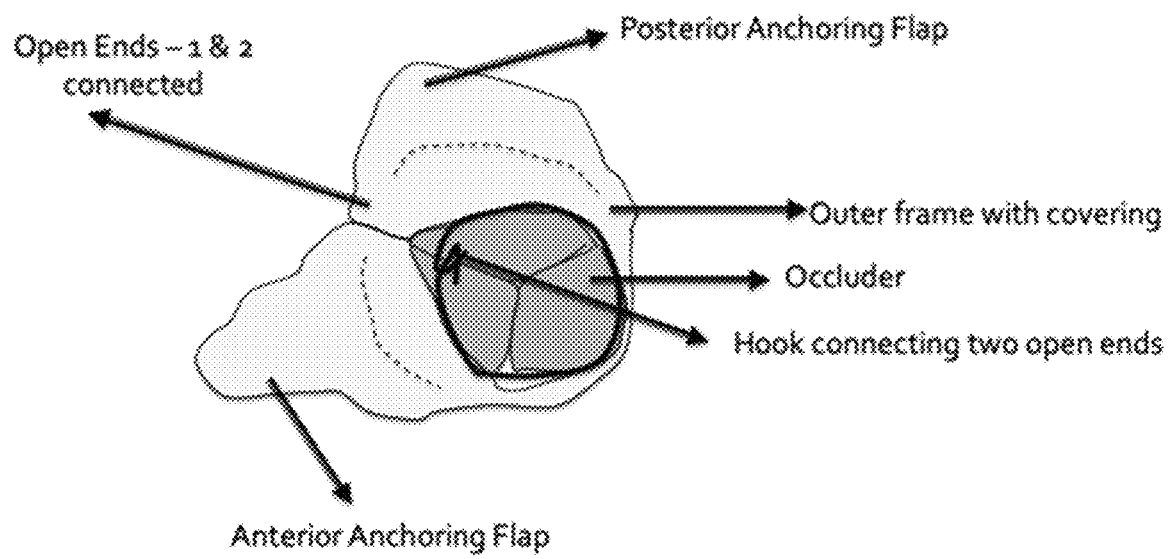
Figure 8A:
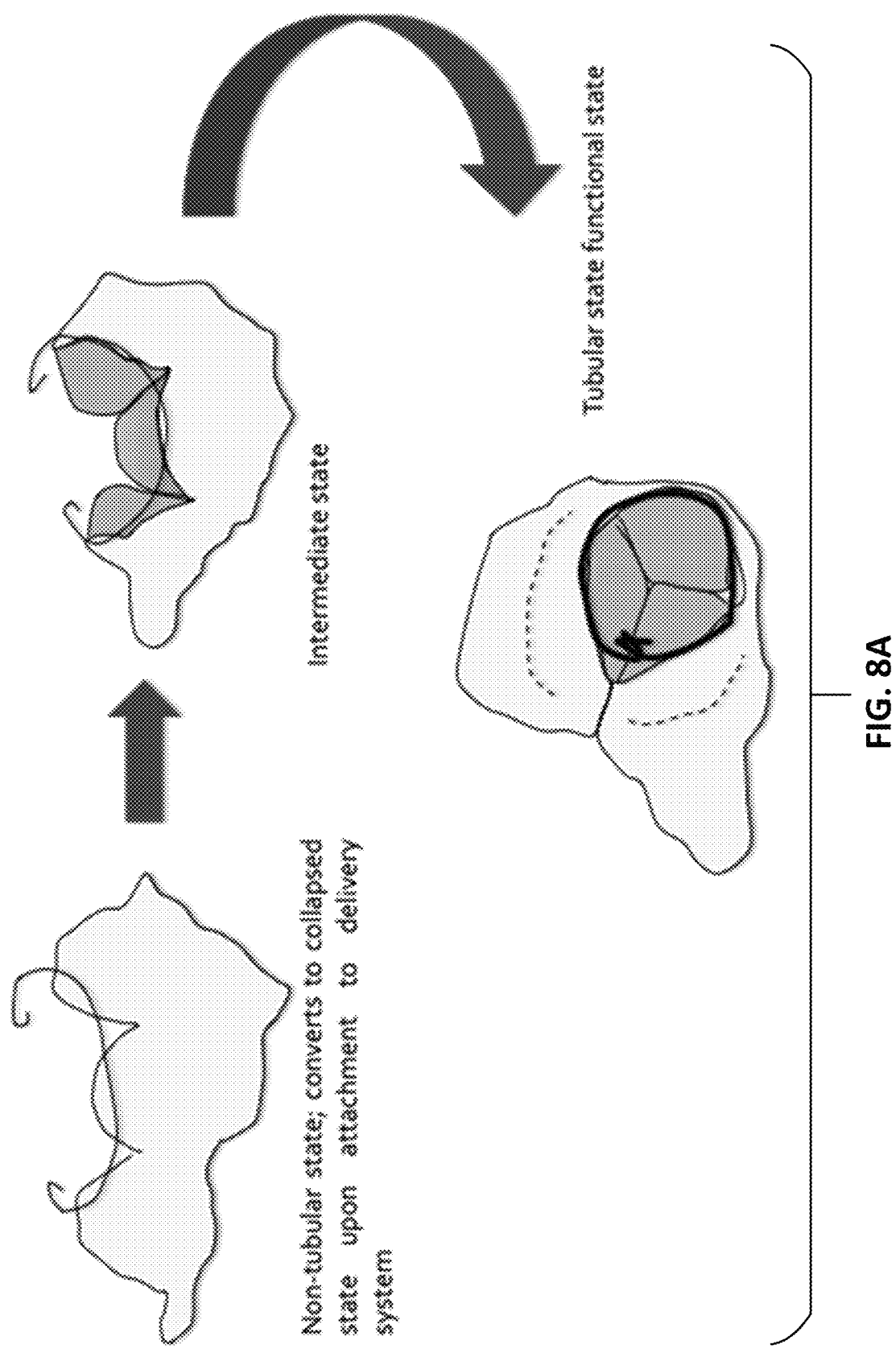
FIG. 8A shows the transformation of the first embodiment of the device of FIGS. 4A, 5A, and 6A to a deployed transcatheter tricuspid valve prosthesis device having anterior and posterior anchoring flaps in their functioning state.

Referring to FIGS. 4A, 5A, 6A, and 8A, for example, a first embodiment of a transcatheter valve prosthesis device can be deployed to replace the function of the native tricuspid valve of FIG. 3 so as to treat tricuspid valve regurgitation, for example. The first embodiment depicted in FIGS. 4A, 5A, and 6A is configured without an atrial shelf (an optional feature depicted in subsequent embodiments). FIG. 4A depicts the device in a first (delivery) configuration, FIG. 5A depicts the device in a second (intermediate) configuration, and FIG. 6A depicts the device in a third (deployed) configuration. As shown in FIG. 8A, the first embodiment of the device can transform, after delivery into the heart, from a first configuration to a deployed transcatheter tricuspid valve prosthesis device having anterior and posterior anchoring flaps in their functioning state.

Figure 4B:
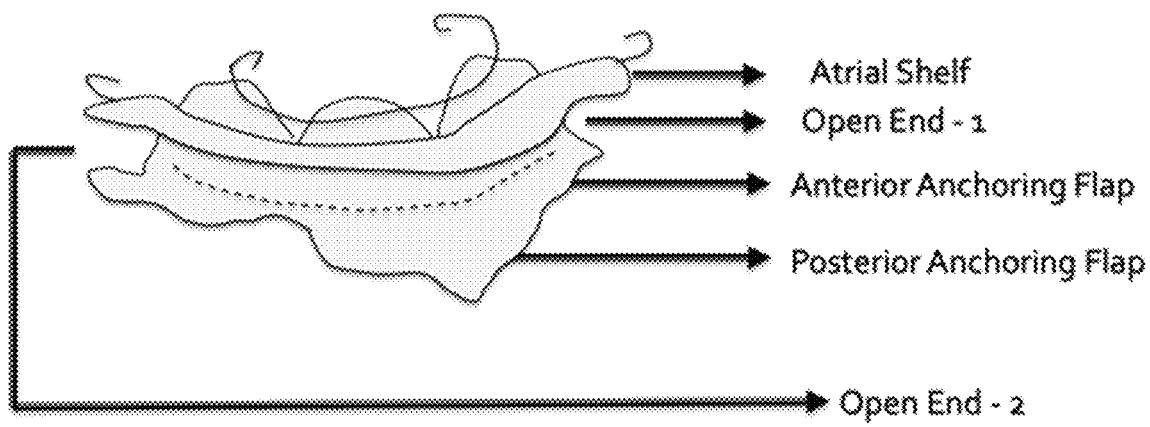
FIGS. 4B, 5B, and 6B shows perspective views of a second embodiment of a transcatheter valve prosthesis device, which can be deployed to replace the tricuspid valve of FIG. 3, in accordance with particular embodiments described herein. The second embodiment depicted in FIGS. 4B, 5B, and 6B includes an atrial shelf, and as shown in FIG. 6B, the anchoring flap and atrial shelf structures extend from an outer (non-cylindrical) frame while the occluder leaflets are positioned with a second inner (generally cylindrical) frame.
Figure 5B:
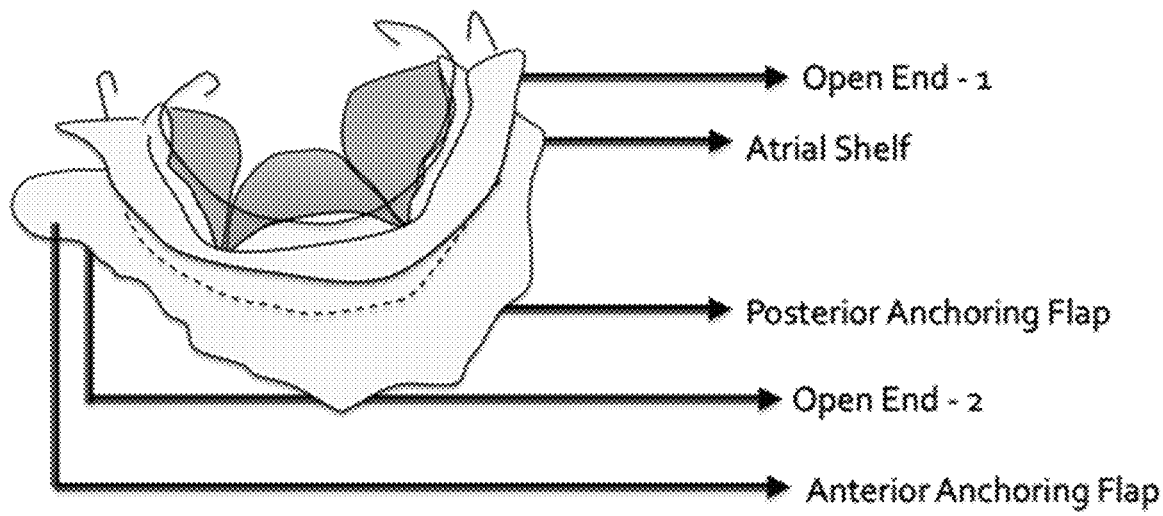
Figure 6B:
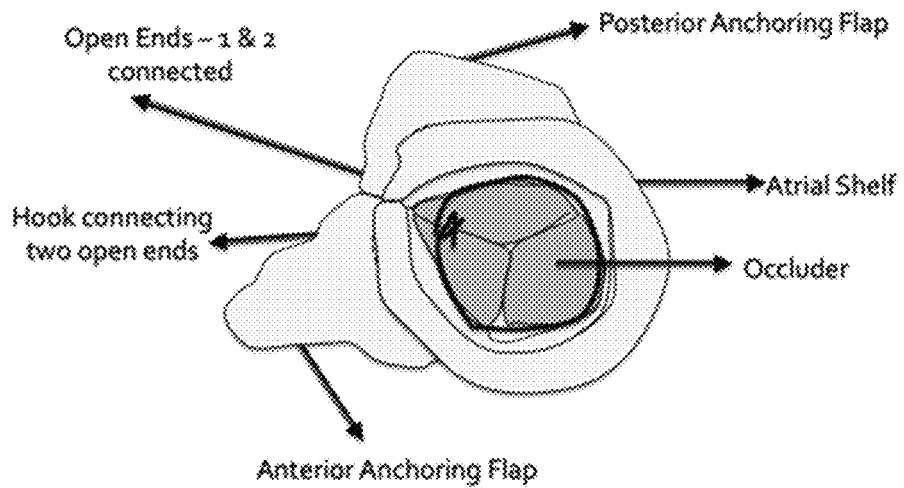

Referring now to FIGS. 4B, 5B, 6B, and 8B, a second embodiment of a transcatheter valve prosthesis device can be deployed to replace the tricuspid valve of FIG. 3. The second embodiment depicted in FIGS. 4B, 5B, and 6B includes an atrial shelf. Also, as shown in FIG. 6B, the anchoring flaps and atrial shelf structures extend from an outer (non-cylindrical) frame while the occluder leaflets are positioned with a second inner (generally cylindrical) frame. FIG. 4B depicts the device in a first (delivery) configuration, FIG. 5B depicts the device in a second (intermediate) configuration, and FIG. 6B depicts the device in a third (deployed) configuration. As shown in FIG. 8B, the second embodiment of the device can transform, after delivery into the heart, from a first configuration to a deployed transcatheter tricuspid valve prosthesis device having with anterior and posterior anchoring flaps in their functioning state and having an atrial shelf.

Figure 4C:
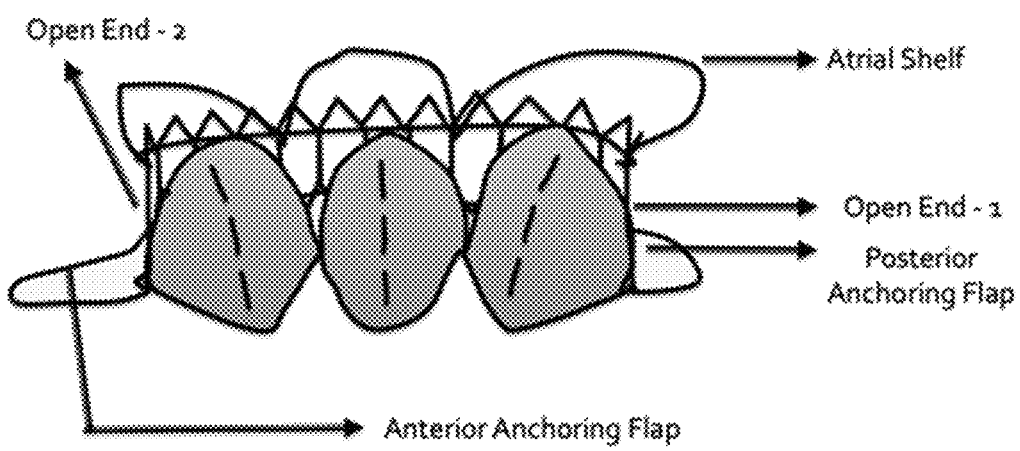
FIGS. 4C, 5C, and 6C shows perspective views of a third embodiment of a transcatheter valve prosthesis device, which can be deployed to replace the tricuspid valve of FIG. 3, in accordance with particular embodiments described herein. The third embodiment depicted in FIGS. 4C, 5C, and 6C is configured so that anchoring flap and atrial shelf structures extend from the same (generally cylindrical) frame as the occluder leaflets.
Figure 5C:
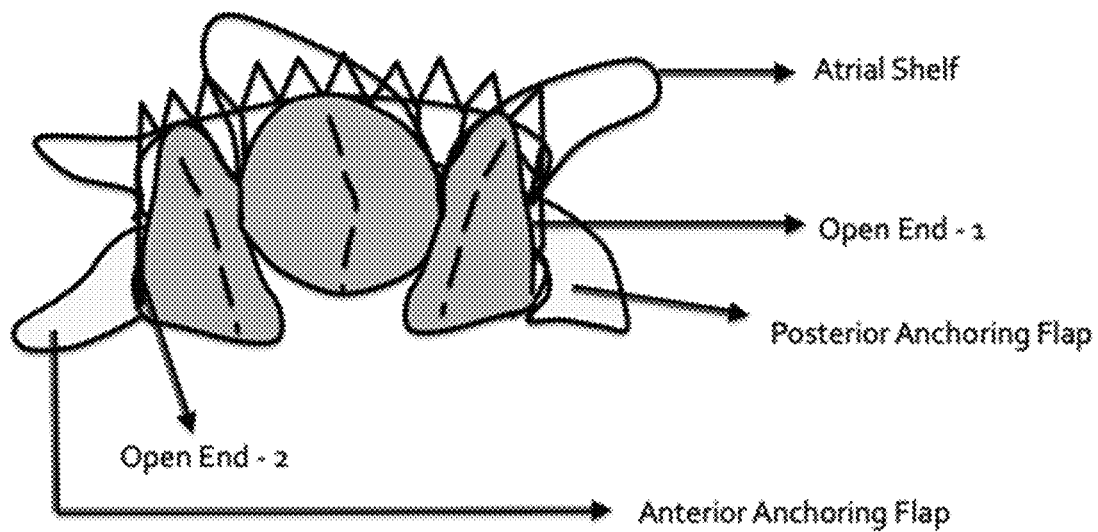
Figure 6C:
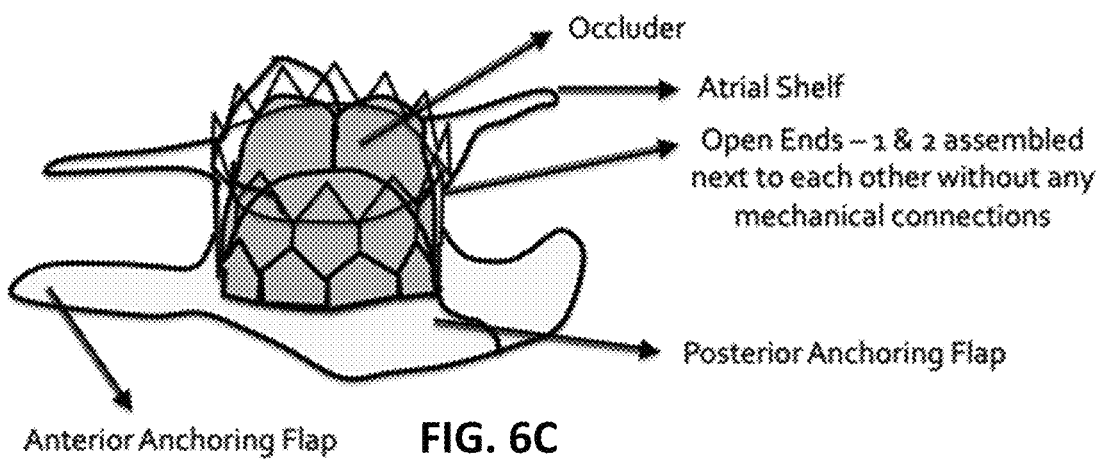
Figure 8C:
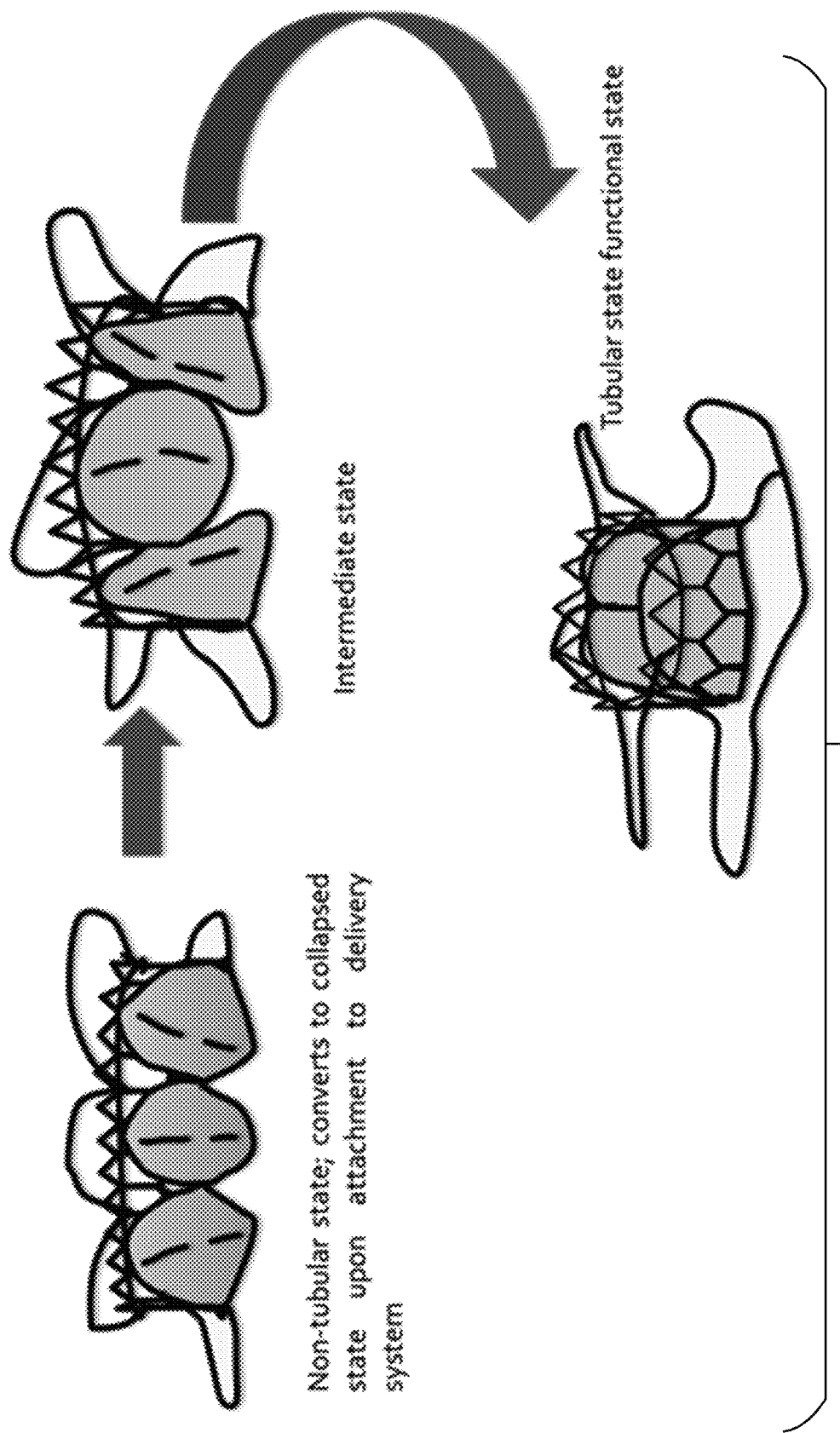
FIG. 8C shows the transformation of the third embodiment of the device of FIGS. 4C, 5C, and 6C to a deployed transcatheter tricuspid valve prosthesis device having anchoring flap and atrial shelf structures extend from the same (generally cylindrical) frame as the occluder leaflets.

Referring now to FIGS. 4C, 5C, 6C, and 8C, a third embodiment of a transcatheter valve prosthesis device can be deployed to replace the tricuspid valve of FIG. 3. The third embodiment depicted in FIGS. 4C, 5C, and 6C is configured so that anchoring flap and atrial shelf structures extend from the same (generally cylindrical) frame as the occluder leaflets. FIG. 4C depicts the device in a first (delivery) configuration, FIG. 5C depicts the device in a second (intermediate) configuration, and FIG. 6C depicts the device in a third (deployed) configuration. As shown in FIG. 8C, the third embodiment of the device can transform, after delivery into the heart, from a first configuration to a deployed transcatheter tricuspid valve prosthesis device having anchoring flap and atrial shelf structures extend from the same (generally cylindrical) frame as the occluder leaflets.

Figure 4D:
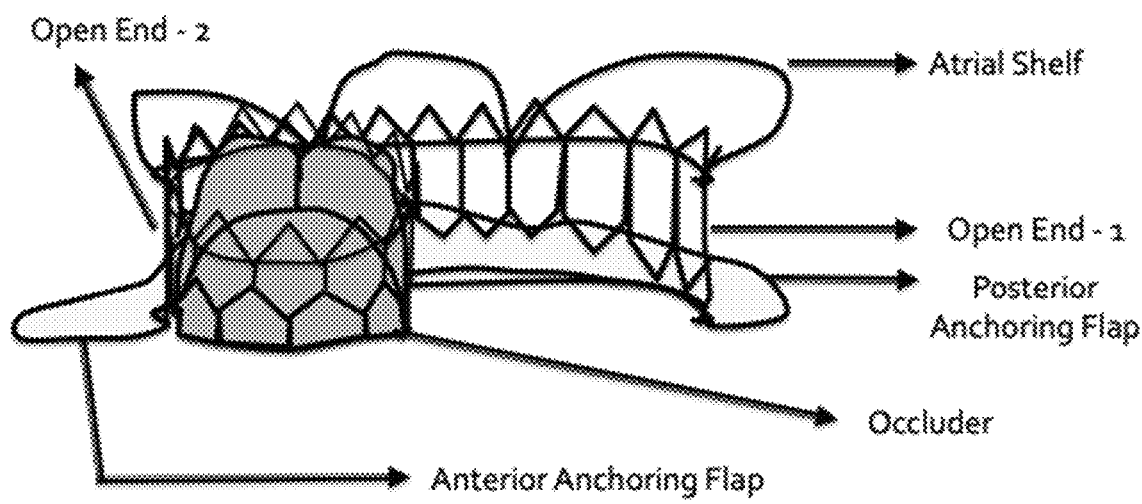
FIGS. 4D, 5D, and 6D shows perspective views of a fourth embodiment of a transcatheter valve prosthesis device, which can be deployed to replace the tricuspid valve of FIG. 3, in accordance with particular embodiments described herein. The fourth embodiment depicted in FIGS. 4D, 5D, and 6D includes an outer frame having open ends that can be joined together after delivery to the heart, and as shown in FIG. 5), the occluder leaflets are positioned with a cylindrical carrier frame formed without open ends (such that the outer frame wraps around the cylindrical carrier frame after delivery to the heart during the deployment stage).
Figure 5D:
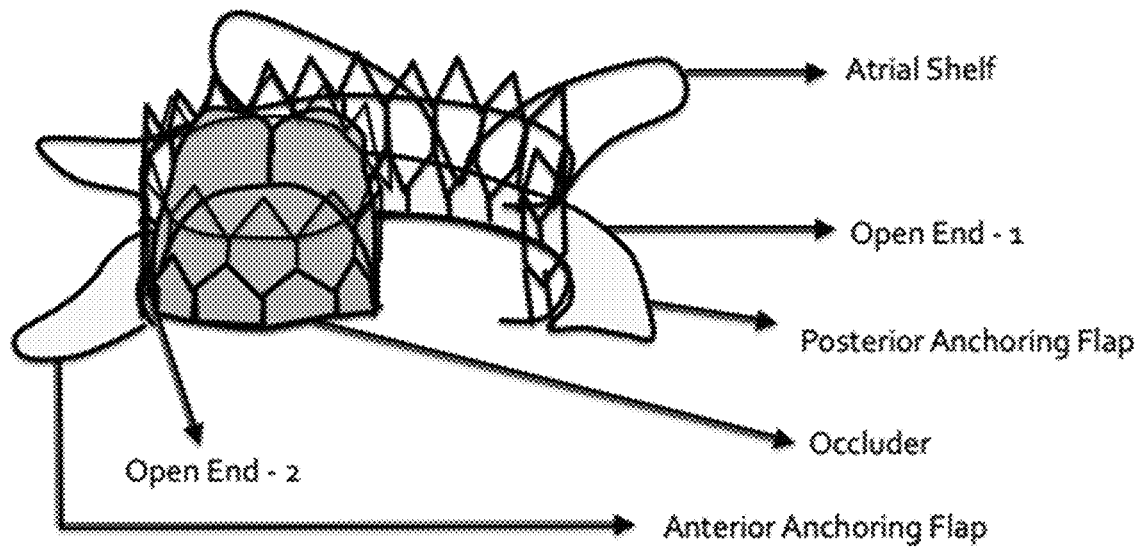
Figure 6D:
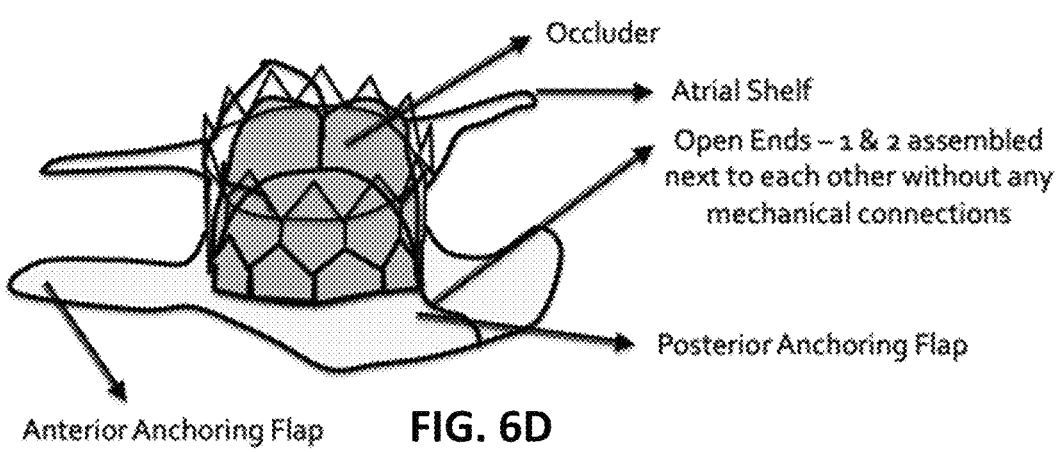
Figure 8D:
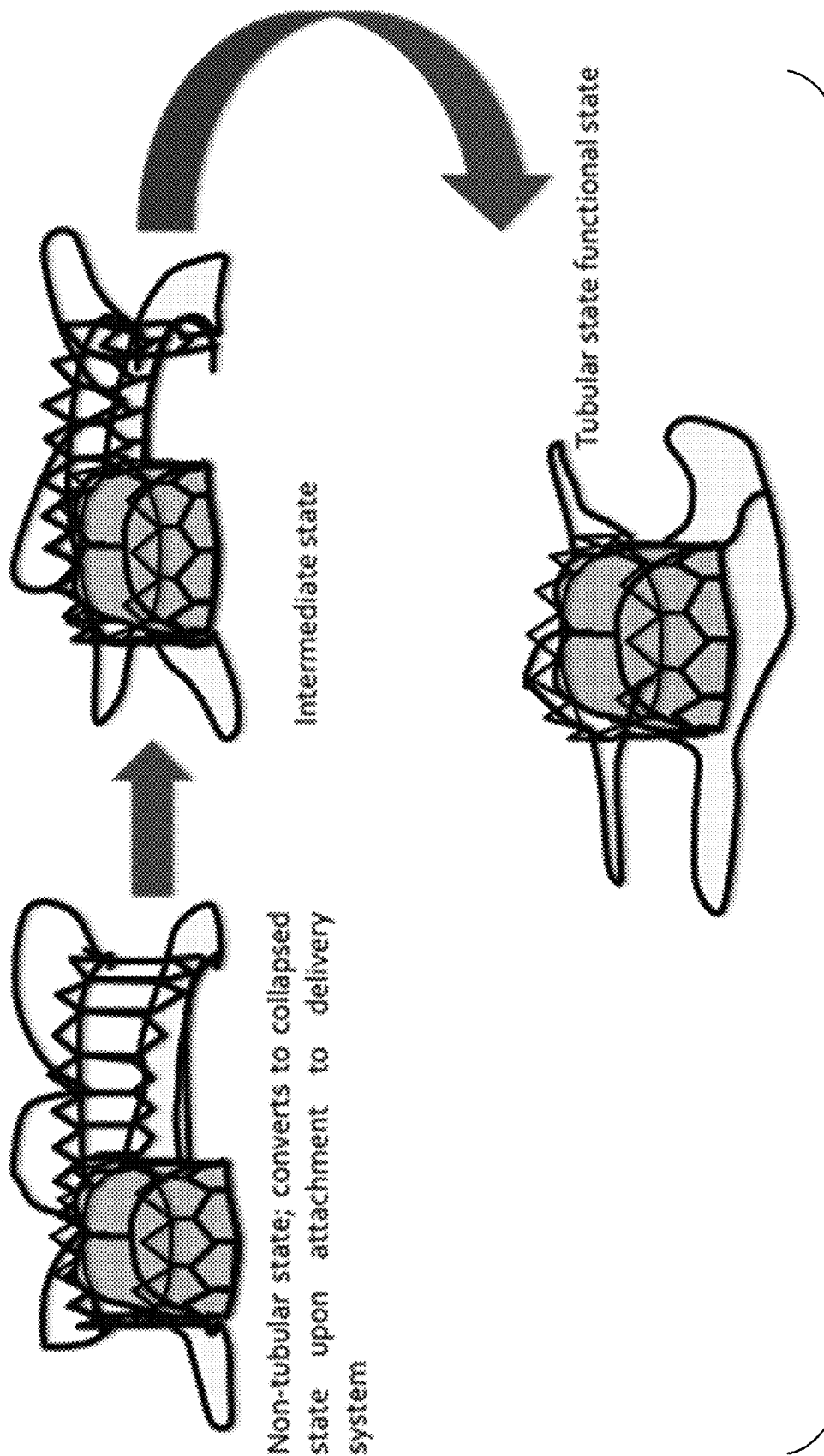
FIG. 8D shows the transformation of the fourth embodiment of the device of FIGS. 4D, 5D, and 6D to a deployed transcatheter tricuspid valve prosthesis device having the occluder leaflets positioned with a cylindrical carrier frame and having the outer frame wrapped around the cylindrical carrier frame.
Figure 10:
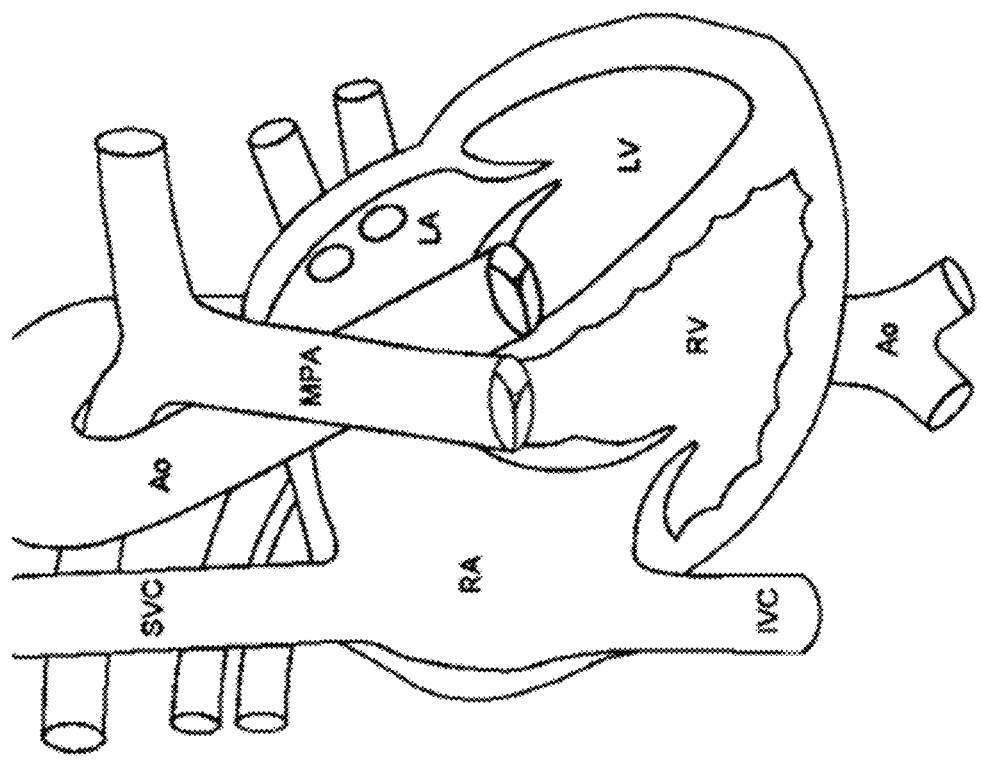
FIG. 10 shows the four chambers of the heart (right atrium, right ventricle, left atrium and left ventricle) as well the major blood vessels that bring blood to the heart (e.g., superior vena cava and inferior vena cava) and those that carry blood away from the heart (e.g., aorta and main pulmonary artery).
Figure 11A:
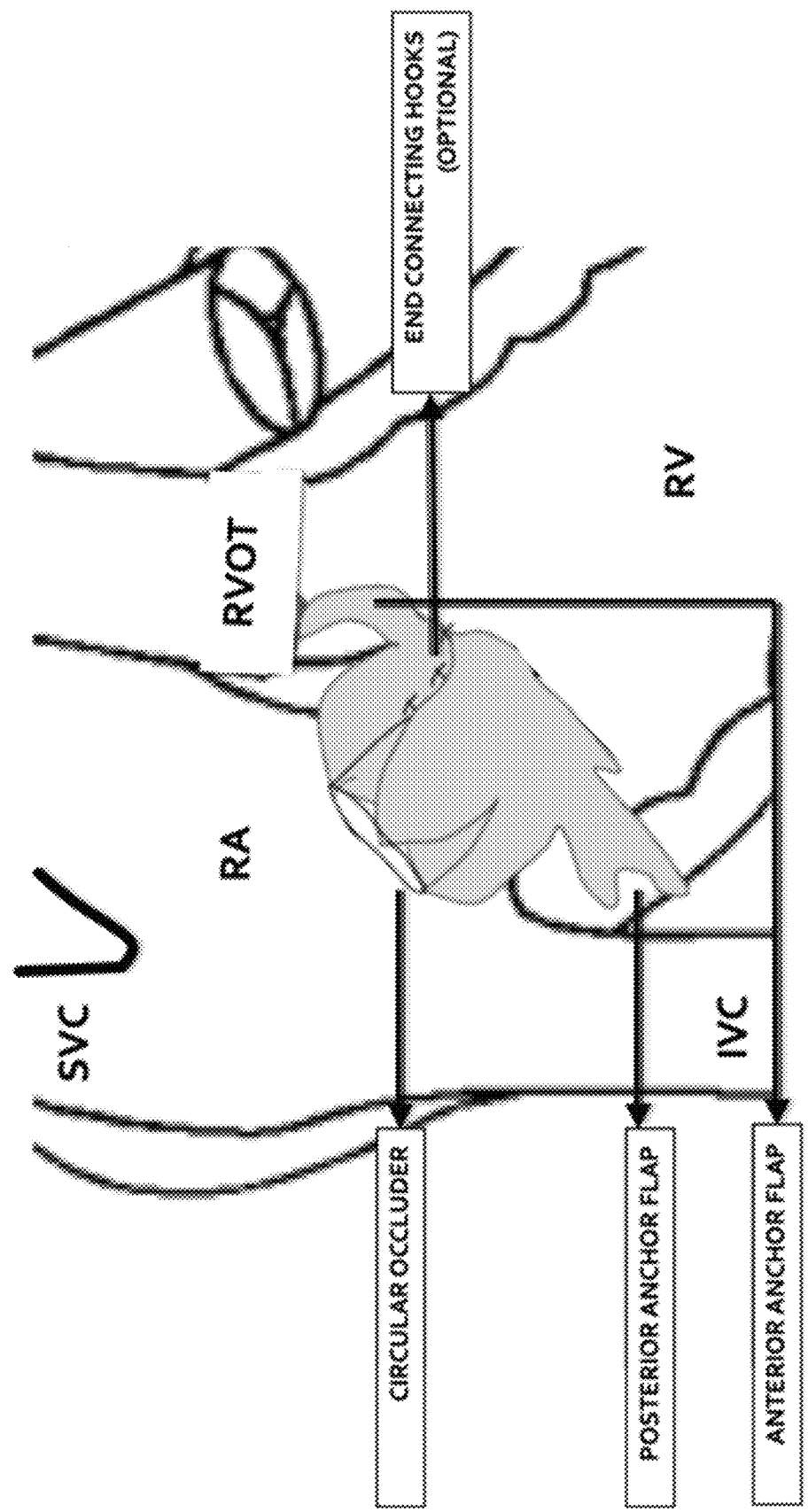
FIG. 11A shows a side view of a tricuspid annulus with the first embodiment of the transcatheter valve prosthesis device (of FIG. 8A) deployed in it.
Figure 11B:
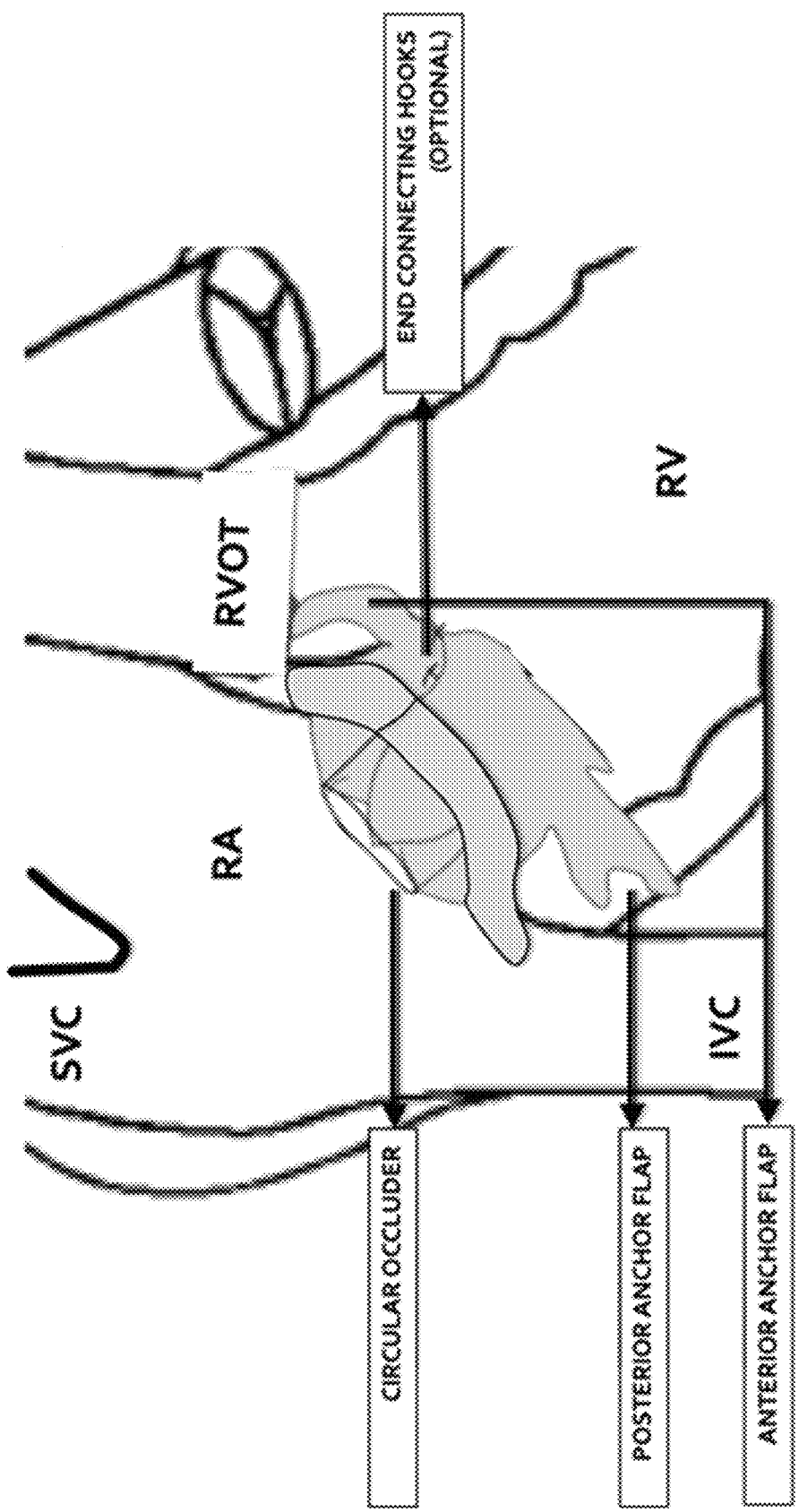
FIG. 11B shows a side view of a tricuspid annulus with one of the second embodiment (FIG. 8B), third embodiment (FIG. 8C), or fourth embodiment (FIG. 8D) deployed in it.

Referring now to FIGS. 4D, 5D, 6D, and 8D, a fourth embodiment of a transcatheter valve prosthesis device can be deployed to replace the tricuspid valve of FIG. 3. The fourth embodiment depicted in FIGS. 4D, 5D, and 6D includes an outer frame having open ends that can be joined together after delivery to the heart, and as shown in FIG. 5), the occluder leaflets are positioned with a cylindrical carrier frame formed without open ends (such that the outer frame wraps around the cylindrical carrier frame during deployment). FIG. 4D depicts the device in a first configuration, FIG. 5D depicts the device in a second (intermediate) configuration, and FIG. 6D depicts the device in a third (deployed) configuration. As shown in FIG. 8D, the fourth embodiment of the device can transform, after delivery into the heart, from a first configuration to a deployed transcatheter tricuspid valve prosthesis device having the occluder leaflets positioned with a cylindrical carrier frame and having the outer frame wrapped around the cylindrical carrier frame.

B. Valve Wrapped Around Inner Delivery Catheter

In particular embodiments, the transcatheter prosthetic heart valve has one free end that is preferentially located or connected to the proximal end of the distal section of an inner delivery catheter and another free end located or connected to the distal end of the distal section of the same inner delivery catheter. One such embodiment is further described in connection with FIGS. 18-20. This confirmation may optionally allow for axial separation along the length of the valve prosthesis thereby wrapping the valve around the inner catheter in a non-tubular helical or spiral fashion. In some instances, such a configuration during delivery can allow for a significantly reduced outer diameter profile, especially where only one leaflet is compressed against the delivery catheter at any given axial position along the catheter. Particular embodiments that can achieve such a beneficial configuration are depicted, for example, in FIGS. 4A-D, 5A-D, 6A-D, and 8A-D.

C. System Description—Valve Wrapped Inside Outer Sheath

In some embodiments, the transcatheter prosthetic heart valve has one free end that is preferentially located at the proximal end of the distal section of an outer sheath catheter and another free end located at the distal end of the distal section of an outer sheath catheter. This allows for axial separation along the length of the valve prosthesis thereby wrapping the valve inside the outer sheath catheter in a non-tubular helical or spiral fashion. This allows for a significantly reduced outer diameter profile as only one leaflet is compressed within the sheath catheter at any given axial position of the catheter. Particular embodiments that can achieve such a beneficial configuration are depicted in FIGS. 4A-D, 5A-D, 6A-D, and 8A-D.

D. System Description—Valve Wrapped Inside Outer Sheath and Around Inner Delivery Catheter In still further embodiments, the transcatheter prosthetic heart valve has one free end that is preferentially located or connected to the proximal end of the distal section of an inner delivery catheter and outer sheath catheter. The other free end of the prosthetic valve is located or connected to the distal end of the distal section of an inner delivery catheter and outer sheath catheter. This allows for axial separation along the length of the valve prosthesis thereby wrapping around the inner delivery catheter and also simultaneously wrapping inside the sheath catheter in a non-tubular helical or spiral fashion. This allows for a significantly reduced out diameter profile as only one leaflet is compressed against the delivery catheter at any given axial position of the catheter. Particular embodiments that can achieve such a beneficial configuration are depicted in FIGS. 4A-D, 5A-D, 6A-D, and 8A-D. One such embodiment is depicted in FIGS. 18-20.

2. Further Options for Valve Prosthesis Design and Construction a. Functional State Description of Prosthesis

The functioning state of the transcatheter heart valve prosthesis is described as the physical state of the heart valve after it is fully deployed at the intended native location within the patient's anatomy. In particular embodiments, there is provided herein a transcatheter prosthetic heart valve that is delivered in a non-tubular and linear configuration with two open ends that can be attached together or otherwise deployed closely inside the patient's body to achieve a functioning (generally tubular) valve prosthesis, such as depicted in FIGS. 6A-6D, 11A and 11B, wherein the valve prosthesis includes a structural frame made from various materials and/or combinations of materials.

In particular embodiments, there is provided a transcatheter prosthetic heart valve that, when deployed at the targeted native valve site, can function as a valve prosthesis defining a generally tubular path through which blood can flow. The structural frame provides mechanical support the flexible leaflets and covering materials of the transcatheter heart valve prosthesis. In the preferred embodiment, the structural frame (which can include an occluder frame, an anchoring skirt frame, and an optional outer frame) could be made from nitinol (NiTi), stainless steel, cobalt chromimum, MP35N steel, titanium, polymeric materials, other biocompatible materials, or any combination thereof. Some or all parts of the frame may be covered with covering materials, which are described below and may include a biocompatible polymer material (e.g., expanded polytetrafluoroethylene (ePTFE) or another synthetic material), natural tissues (e.g., bovine, porcine, ovine, or equine pericardium), or a combination thereof. Depicted as part of some embodiments in FIGS. 6A-D are varying configurations of structural frames with coverings. It should be understood that, in some of views depicted in FIGS. 4A-D, 5A-D, 6A-D, and 8A-D, at least a portion of the covering material is removed from view in the depicted structure purposes of illustrating the structural frame.

As described previously, the structural frame can be further divided into occluder frame, anchoring skirt frame and an optional outer frame.

i. Occluder Frame Design

In particular embodiments, there is provided a transcatheter prosthetic heart in its functional state, has an occluder that is circular and in turn made of two (2) or more flexible leaflets. The flexible leaflets are attached to the occluder frame through sutures thereby making the occluder frame the structural framework of the valve prosthesis occluder. Other embodiments of the prosthetic heart valve may include other non-circular closed shapes such as triangle, square, pentagon, hexagon, or other polygons for the occluder frame. A circular occluder with three (3) flexible leaflets as part of varying embodiments is/are depicted in FIGS. 4D, 5D and 6A-D.

ii. Outer Frame Design

In some embodiments, in its functioning state, the valve prosthesis has an optional non-cylindrical outer frame that links the proximal part (which is circular occluder frame in the preferred embodiment) and the distal part that terminates in the outer external anchoring skirt frame. Referring to FIGS. 6A and 6B, shown are some embodiments of a valve prostheses with an outer frame.

In some embodiments, in its functioning state, the valve prosthesis has no outer frame but instead the occluder frame is directly connected to anchoring skirt frame. Referring to FIGS. 6C and 6D, shown are some embodiments of a valve prosthesis without an outer frame. Referring to FIG. 6D, shown is one embodiment, where the occluder frame is adjacent to the frame that is also cylindrical, but has open ends and that connects to the anchoring skirt frame.

iii. Anchoring Skirt Frame Design

Referring to FIGS. 6A, 6B, 6C and 6D, a transcatheter prosthetic heart can be deployed in its functional state, and some embodiments may include an anchoring skirt frame that is connected to the occluder frame through the outer frame or is directly connected to the occluder frame in other embodiments. In these embodiments, the anchoring skirt also acts as the sealing skirt. In one embodiment for a transcatheter tricuspid valve replacement, the anchoring skirt includes an anterior flap and a posterior flap that provide anchoring as well as sealing in the anterior and posterior region of the tricuspid annulus. In other embodiments of transcatheter valve protheses for mitral, aortic and pulmonary valve replacements, the anchoring skirt will have shapes and features specific to anatomical features of those respective native valve sites. In some embodiments, in its functioning state, the prosthetic valve has an outer external anchoring skirt that extends distally and axially beyond the occluder portion by 0.1 mm to 25 mm, preferably in the 0.1 mm to 10 mm.

iv. Leaflet Design & Material

Referring to FIGS. 6A, 6B, 6C and 6D, in some embodiments, there is provided a transcatheter prosthetic heart in its functional state, has an occluder that is circular and in turn made of three or more flexible leaflets. The depicted embodiments employ three leaflets, which is referred to as tri-leaflet occluder. The occluder portion of the valve device can optionally employ configurations other than a tri-leaflet occluder. For example, bi-leaflet, quad-leaflet, or mechanical valve constructs can be used in some embodiments. In particular implementations described herein, the flexible leaflets are made of natural tissues such as porcine or bovine or equine or ovine pericardium. In such embodiments, the tissues are chemically cross-linked using glutaraldehyde or formaldehyde, or other aldehydes commonly used as cross-linking agents. In other embodiments, the flexible leaflets are made of polymers such as polyurethane, polyester (DACRON) or expanded polytetrafluoroethylene (ePTFE). The flexible leaflets are attached to structural frame using sutures that could be made of combination of material including but not limited to UHMWPE (ultra high molecular weight polyethylene) or nylon or polyester (DACRON).

v. Outer Cuff Design & Material

Referring to FIGS. 6A and 6B, in some embodiments, there is provided a transcatheter prosthetic heart valve in its functional state, having an outer frame that connected to the occluder. In its functioning state, the valve prosthesis has an outer frame that links the proximal part (which is circular in the preferred embodiment) and the distal part that terminates in the outer external anchoring skirt. In some embodiments, the outer frame is covered with an outer cuff that is made of natural tissues such as porcine or bovine or equine or ovine pericardium. In some such embodiments, the tissues are chemically cross-linked using glutaraldehyde or formaldehyde, or other aldehydes commonly used as crosslinking agents. In some other embodiments, the outer cuff is made of biocompatible polymers such as polyurethane, polyester (DACRON) or expanded polytetrafluoroethylene (ePTFE). The outer cuff is attached to outer frame using sutures that could be made of combination of material including but not limited to biocompatible polymers such as UHMWPE (ultra high molecular weight polyethylene) or nylon or polyester (DACRON).

vi. Anchoring Skirt Design & Material

Referring to FIGS. 6A, 68, 6C and 6D, in some embodiments, there is provided a transcatheter prosthetic heart in its functional state, has an anchoring skirt frame that is connected to the occluder frame through the outer frame. In one embodiment, the anchoring frame is covered with anchoring cuff, that is preferably in one embodiment, in contact with the native valve leaflets, native valve annulus, native ventricular tissue, native atrial tissue or a combination of all the native tissues. In other embodiment, the anchoring cuff could be attached to the inside of the anchoring skirt frame. In one embodiment, the anchoring cuff that is made of natural tissues such as porcine or bovine or equine or ovine pericardium. In such embodiments, the tissues are chemically cross-linked using glutaraldehyde or formaldehyde, or other aldehydes commonly used as crosslinking agents. In other embodiments, the outer cuff is made of polymers such as polyurethane, polyester (DACRON) or expanded polytetrafluoroethylene (ePTFE). The anchoring cuff is attached to anchoring skirt frame using sutures that could be made of combination of material including but not limited to UHMWPE (ultra high molecular weight polyethylene) or nylon or polyester (DACRON).

vii. End Connections

Referring to FIGS. 6A and 6B, in some embodiments, the transcatheter prosthetic heart valve can be deployed inside the patient's body (blood vessel such as artery or vein, native valve such as aortic or pulmonary or mitral or tricuspid, chambers of heart such as right atrium or left atrium or left ventricle or right ventricle) such that during the deployment, the two open ends of the valve prosthesis are connected to form a tubular heart valve prosthesis. The two open ends are connected with each other in the functioning state of the heart valve prosthesis through features referred to as end connections. These end connections can include hooks, barbs, cleats, folds, projections, overlapping flaps, or others.

Figure 7:
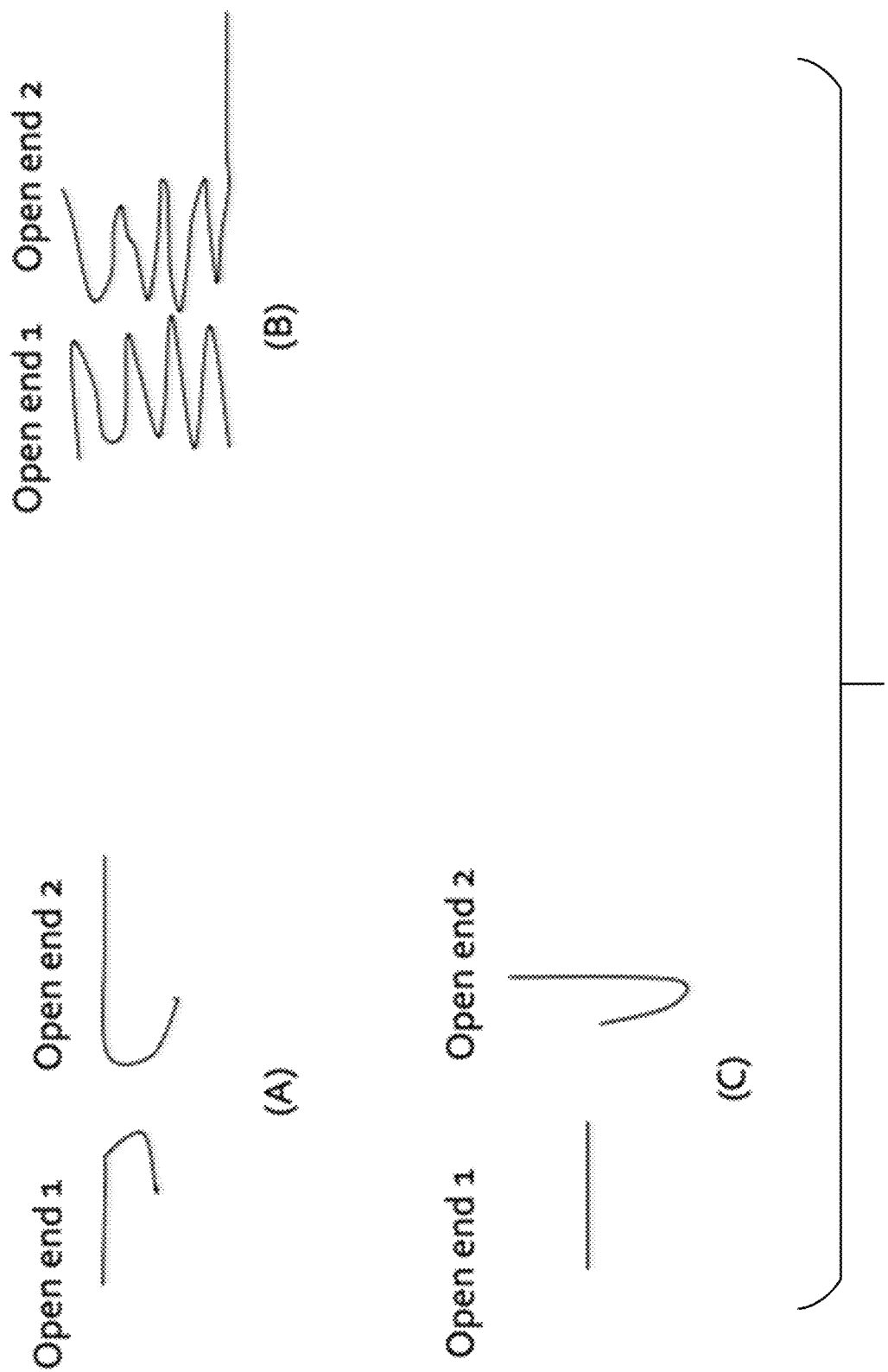
FIG. 7 shows different embodiments of connecting features on the two open ends of the transcatheter valve prosthesis: (A) horizontal hooks on both open ends, (B) combs on both open ends, and (C) vertical hook on one open end and tab on the other open end.

Depicted in FIGS. 7A, 7B and 7C are examples of different end connections. These end connections are on one or both open ends of the valve prosthesis and interact with each other or the other open end to create a mechanical lock. These end connections could be extensions of the structural frame and may be covered with coverings such as polyester or ePTFE or other such polymers.

Referring to FIGS. 6C and 6D, in some embodiments, the transcatheter prosthetic heart valve can be deployed inside the patient's body (blood vessel such as artery or vein, native valve such as aortic or pulmonary or mitral or tricuspid, chambers of heart such as right atrium or left atrium or left ventricle or right ventricle) such that during the deployment, the two open ends of the valve prosthesis are assembled or deployed adjacent to each other without a mechanical connection to appear in the form a tubular heart valve prosthesis in its functioning state.

b. Collapsed State Description

The collapsed state of the transcatheter heart valve prosthesis is described as the physical state of the heart valve starting from when it is loaded in or onto the delivery system until it is fully deployed in the functioning state.

In some embodiments, there is provided a transcatheter prosthetic heart valve in its collapsed state, where the structural frame and coverings (e.g., outer cuff and anchoring cuff) are all open ended, non-tubular, linear and are wrapped or folded around an inner delivery catheter in a helical or spiral fashion. Particular embodiments that can achieve such a collapsed state are depicted in FIGS. 4A-C and 5A-C. Further, referring to FIGS. 17-20, in some embodiments, the wrapping or folding of the valve(s) depicted in FIGS. 4A-C and 5A-C is such that a valve prosthesis (that is ultimately tubular looking in the functioning state) is delivered while configured as a helical, non-tubular valve prosthesis with open ends. The number of turns of the helix can be anywhere from 0.1 to 10. This is depicted in FIG. 19a, for example.

Figure 19:
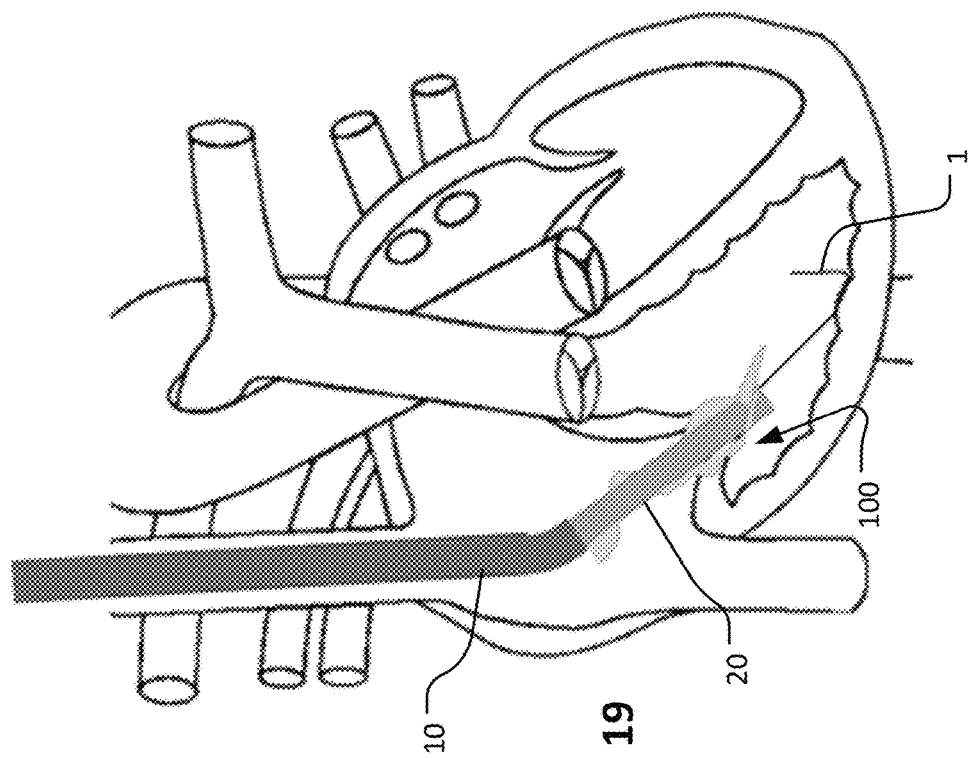
Figure 19A:
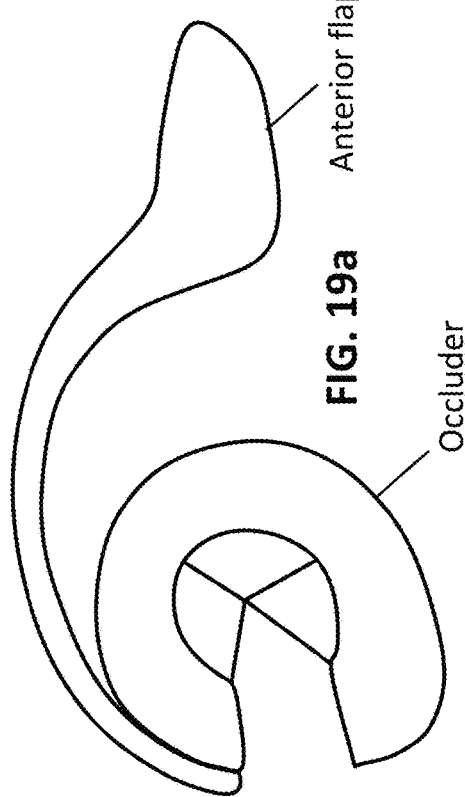

In FIG. 19a, a top view of the prosthetic valve showing the outer cuff, the anchoring cuff (anterior flap), and the occluder shows that each are in their non-tubular collapsed state during the initial state of deployment. FIG. 19d also shows the occluder portion (by itself) in the non-tubular state.

Figure 19B:
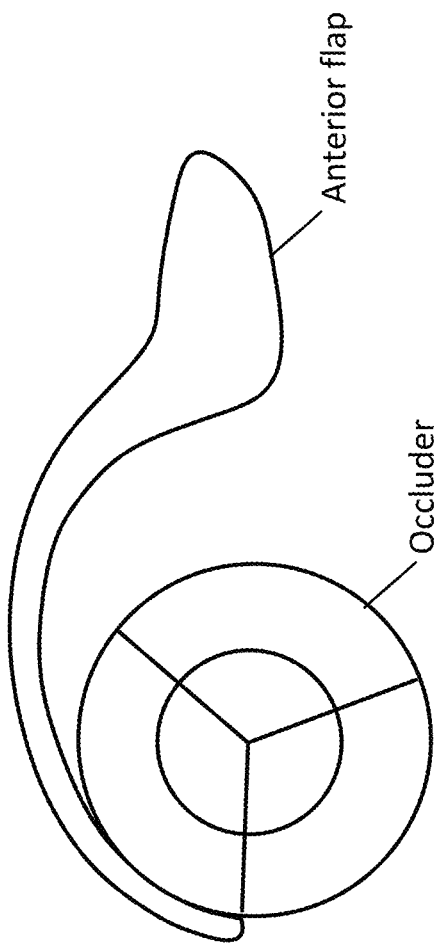

As depicted in FIG. 19b, when the release of the prosthetic valve from the delivery catheter takes begins to take place, the occluder portion of the prosthetic valve will begin to reconfigure into a final/delivered tubular configuration (also see FIG. 19e), while the anterior flap may still be extended/separated away from the occluder portion.

Figure 19C:
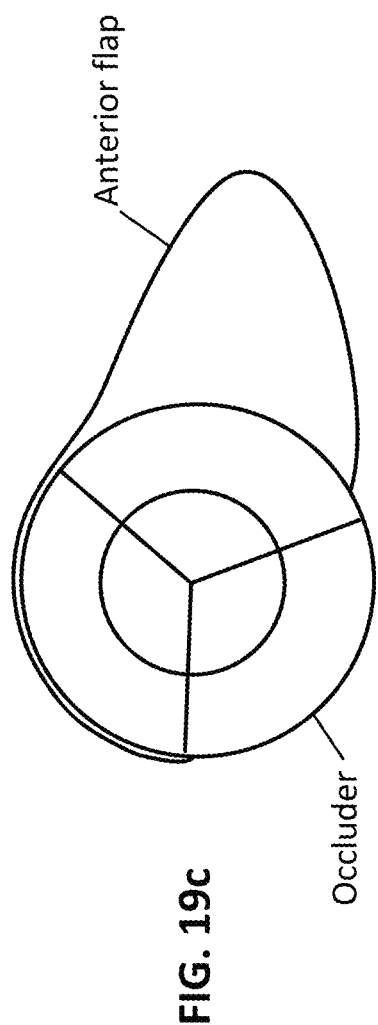
Figure 19D:
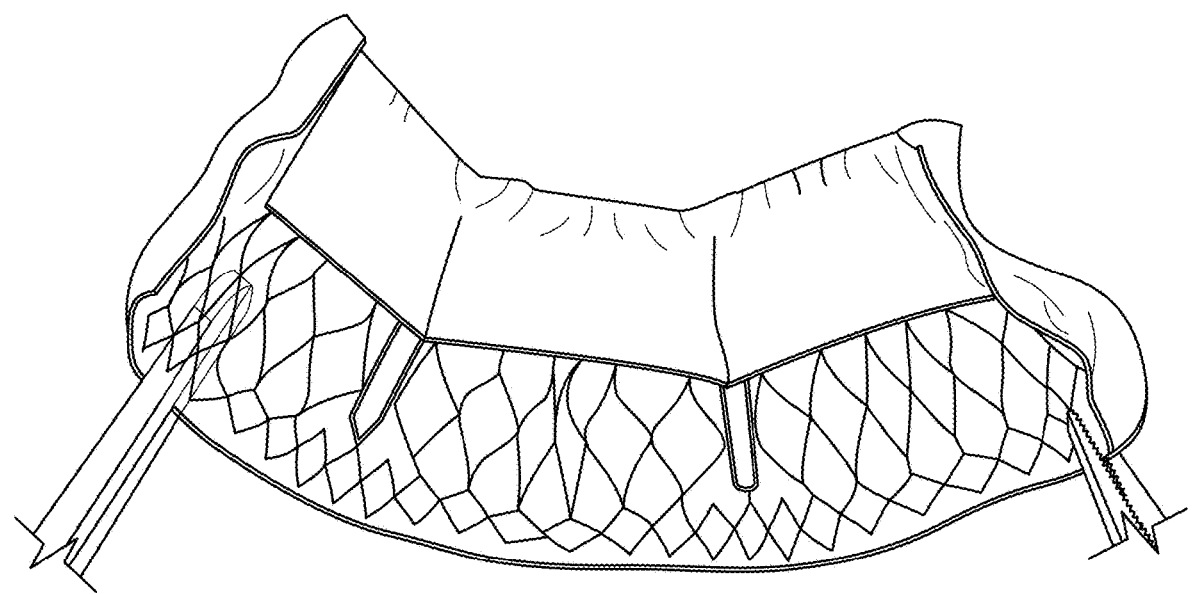

To complete the deployment of the prosthetic valve, as depicted in FIG. 19c, the anchoring cuff (anterior flap) becomes free to move adjacent to the occluder portion of the prosthetic valve.

Figure 19E:
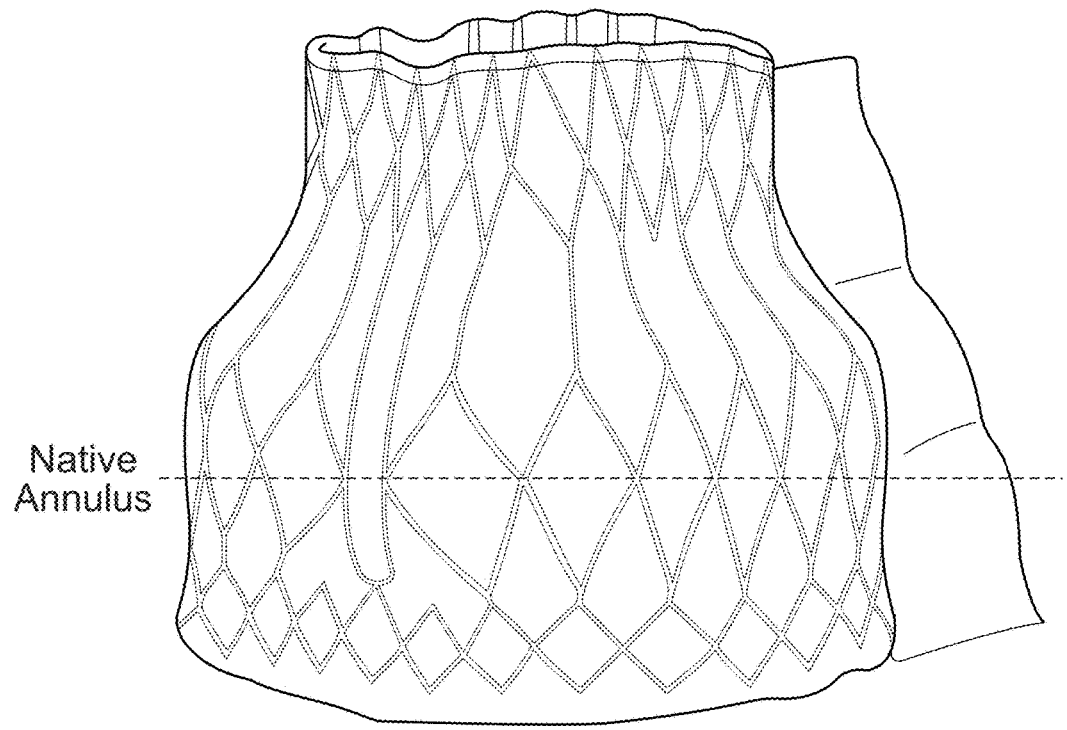

In FIG. 19e, the horizontal dashed line represents the position of the native valve annulus when the prosthetic valve is implanted in the native valve. It can be seen that the cells of the framework of the prosthetic valve are larger in the mid-body region at the native valve annulus than are the cells at the upper and lower ends of the framework. The larger cells of the mid-body region provide enhanced flexibility to enable the valve to conform to the natural shape of the opening of the native valve at the valve annulus.

In some embodiments, there is provided a transcatheter prosthetic heart in its collapsed state, where the structural frame and coverings (i.e. outer cuff and anchoring cuff) except the occluder are all open ended, non-tubular linear and are wrapped or folded inside an outer delivery sheath catheter in a helical or spiral fashion. The occluder, in contrast, is tubular and is diametrically collapsed in the collapsed state. Particular embodiments that can achieve such a collapsed state are depicted in FIGS. 4D and 5D. In some such embodiments, while such a transcatheter prosthetic heart valve in its collapsed state, the structural frame and coverings of the outer cuff and anchoring cuff are open ended, non-tubular, linear and wrapped or folded inside an outer delivery sheath catheter in a helical or spiral fashion, while the occluder is tubular. The number of turns of the helix/spiral can be anywhere from 0.1 to 10.

3. Description of Delivery System Design and Construction

In particular embodiments, there is provided a delivery system that is used for the delivery of transcatheter prosthetic heart valves described herein. The delivery system also transforms the transcatheter valve prosthesis from a non-tubular, linear, helical and open-ended form in its collapsed state to a tubular prosthesis in its functioning state through methods described herein.

Referring to FIGS. 12-23, an example system and method of delivering and deploying of the valve prosthesis devices described herein includes one such delivery system, which can comprise an outer delivery sheath and inner delivery catheter. For example, as showing in FIGS. 12-23, the delivery system includes an outer delivery sheath catheter 10, inside of which there is an inner delivery catheter 20 to which the non-tubular, linear, helical and open-ended valve prosthesis 100 is attached on the outside. In one preferred embodiment, this delivery sheath catheter 10 may be deflectable or steerable in one plane, for example, as depicted in the example of FIGS. 15-22. In other embodiments, there may be two (2) or more deflection planes that may or may not be orthogonal to each other. Other embodiments of this catheter 10 may also have no deflection and/or may have a fixed curve associated with it. To the inside of the delivery catheter 10, in one preferred embodiment, there is a lumen for guidewire 1 (for example, as depicted in the example of FIGS. 15-21).

Figure 17:
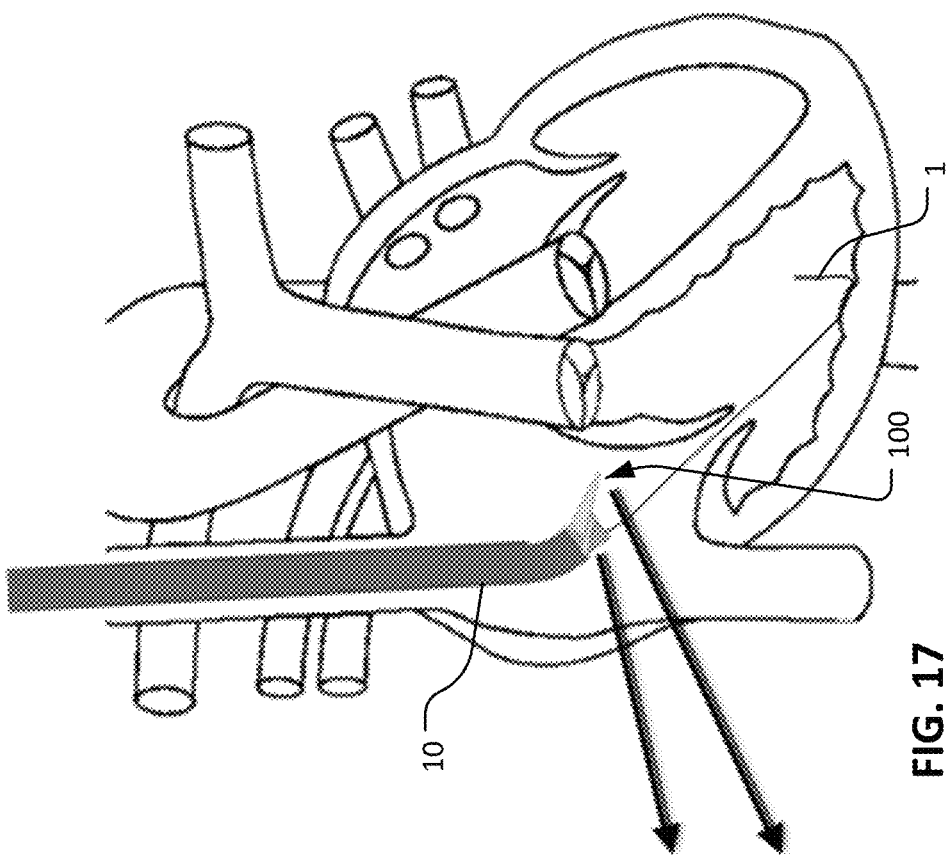
Figure 18:
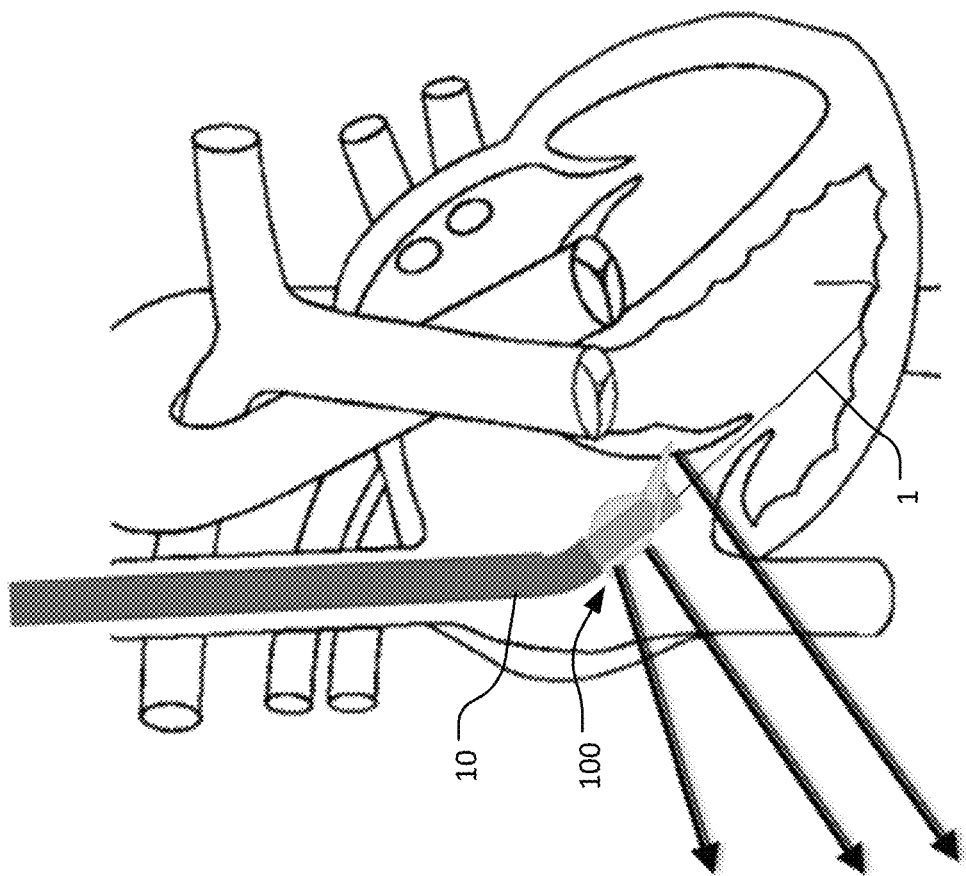

Referring to FIGS. 17-19, in some embodiments, the delivery system includes an outer delivery sheath catheter 10, inside of which there is an inner delivery catheter 20 to which the non-tubular, linear, helical and open-ended valve prosthesis 100 is attached on the outside. To the inside of the delivery catheter 10, in some embodiments, there may be another internal steerable catheter 20. To the inside of the internal steerable catheter 20, in some optional embodiments, there may be lumen for a guidewire 1. In one embodiment, this inner steerable catheter 20 may be deflectable or steerable in one plane. In other embodiments, there may be two (2) or more deflection planes that may or may not be orthogonal to each other. To the inside of the delivery catheter 10, in one preferred embodiment, there is a lumen for a guidewire 1.

In one preferred embodiment, the delivery sheath catheter 10 is the primary catheter that provides access to the right atrium for a tricuspid valve replacement as also depicted in FIGS. 15-22. Other embodiments may include a delivery sheath catheter that provides access to left atrium, left ventricle, aorta, pulmonary artery or right ventricle.

4. Method of Delivery of Transcatheter Valve

Referring to FIGS. 12-23, an example method to deploy some embodiments of a transcatheter tricuspid valve prosthesis is described. Similar methods to deploy transcatheter prostheses in mitral, aortic and pulmonary positions can be extrapolated.

Figure 12:
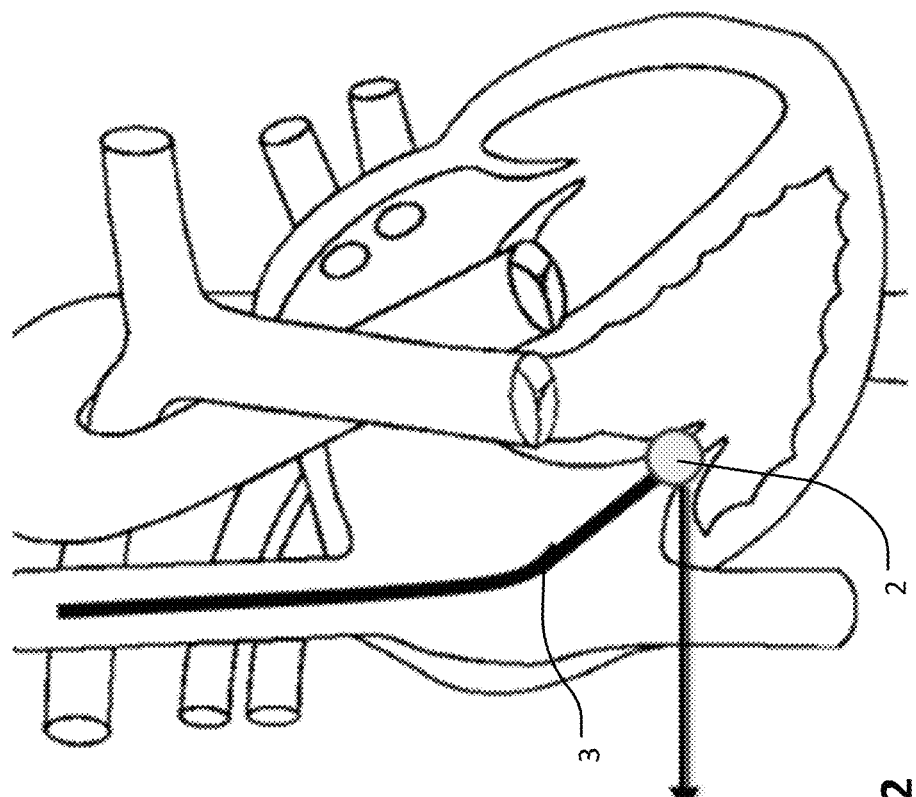
FIGS. 12-23 show a example method of deploying of a transcatheter tricuspid valve prosthesis, such as one of the first embodiment (FIG. 8A), the second embodiment (FIG. 8B), third embodiment (FIG. 8C), or fourth embodiment (FIG. 8D), with the method including the transformation of valve prosthesis device to its tubular form at the targeted site of the native tricuspid annulus.
Figure 13:
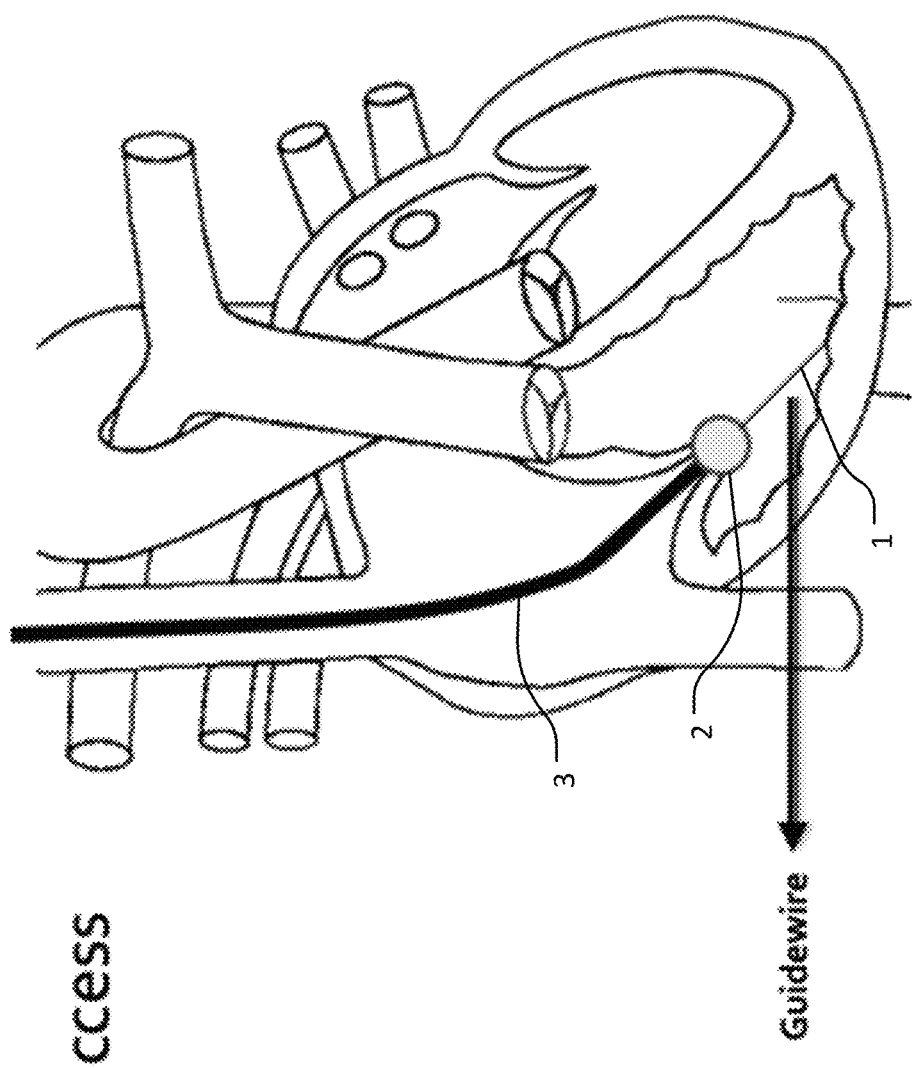
Figure 14:
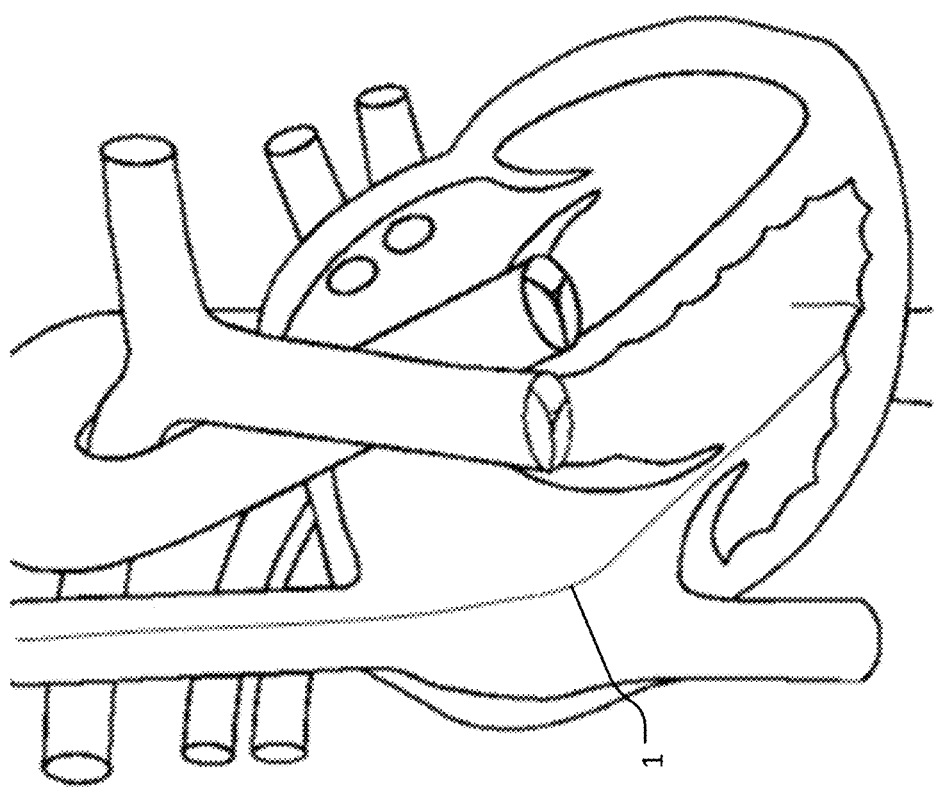

In particular embodiments, a balloon 2 may be positioned within and/or floated across the tricuspid annulus as depicted in FIGS. 12 and 13. The balloon catheter 3 may be inserted into the patient's blood vessel either through preferred trans-jugular venous access or through a trans-femoral venous access. While a trans-jugular venous access will access the right atrium through the superior vena cava, a trans-femoral venous will access the right atrium through the inferior vena cava. Guidewire 1 may then be inserted through the lumen of the balloon catheter 3 into the right ventricle.

Figure 15:
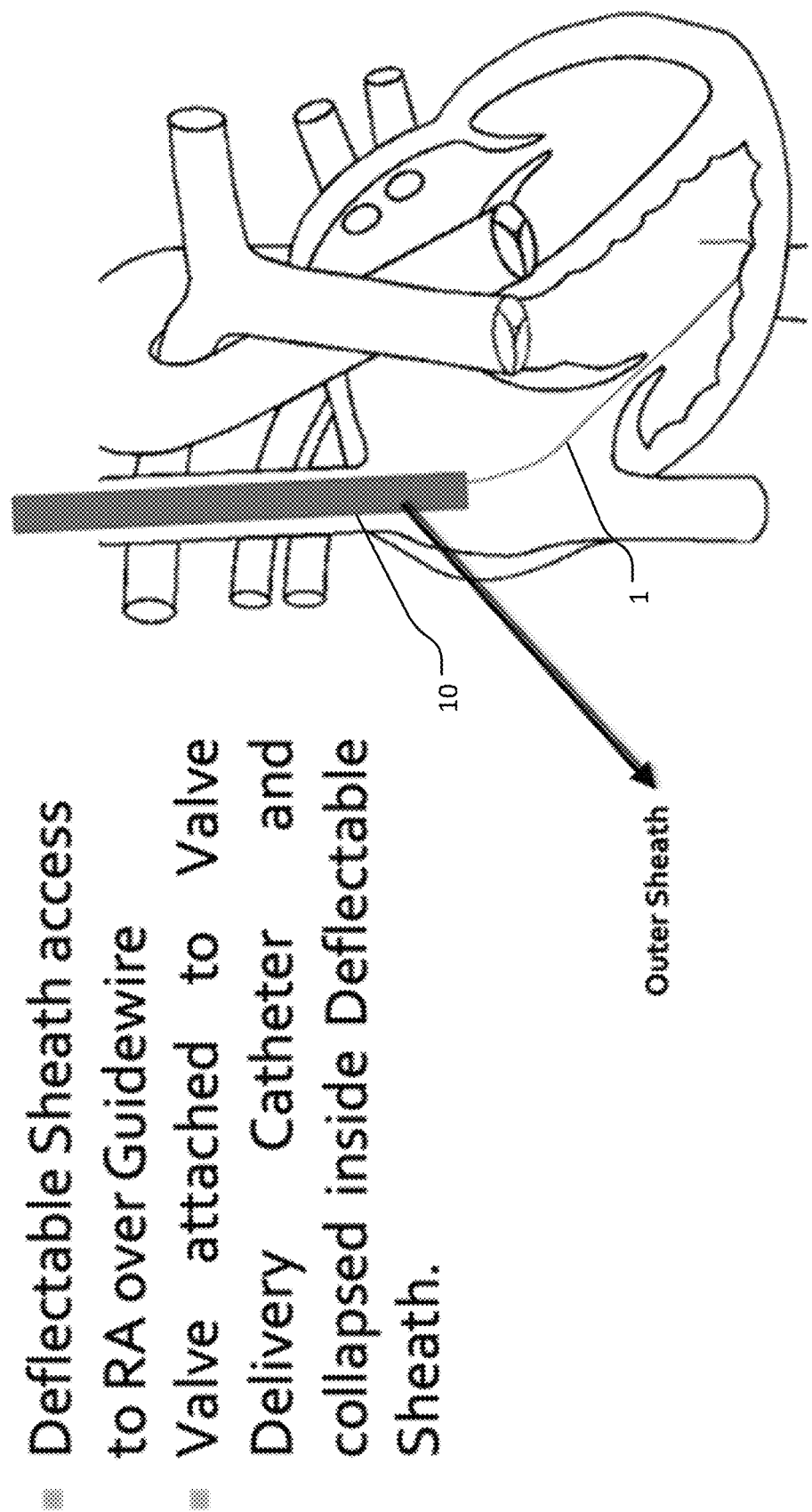
Figure 16:
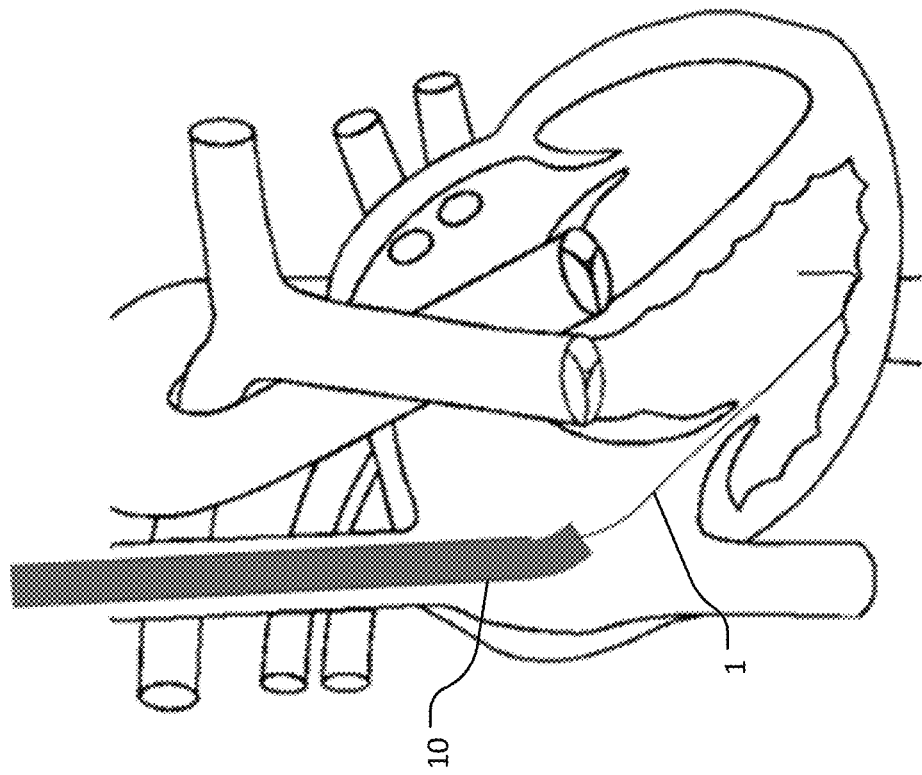

In one preferred embodiment, a delivery system comprising of an outer deflectable sheath catheter 10 and an inner delivery catheter 20 with a transcatheter valve prosthesis 100 wrapped or folded around it and connected to it may be inserted into the patient's blood vessel all the way up to right atrium as depicted in FIG. 15. Referring to FIG. 16, the outer deflectable sheath 10 may be deflected to point the system towards the tricuspid annular plane. Referring to FIGS. 17-19, the valve prosthesis 100 may then be unsheathed by advancing the valve delivery catheter 20.

In one such embodiment, the transcatheter valve prosthesis 100 that non-tubular, linear, helical and open-ended as well as is attached to the delivery catheter 20 is advanced such that some sections of the valve prosthesis 100 may begin to engage the intended native site (as depicted in FIG. 19). Referring to FIGS. 20, 21, 22 and 23, in one such embodiment, describing a transcatheter tricuspid valve prosthesis 100, an anterior anchoring flap may engage with anterior region of the tricuspid annulus followed by the posterior anchoring flap engaging with the posterior region of the tricuspid annulus. During the engagement of different sections, the valve is also assembled in its functioning state at the native valve annulus site, similar to one depicted in FIGS. 20, 21, 22 and 23.

Figure 20:
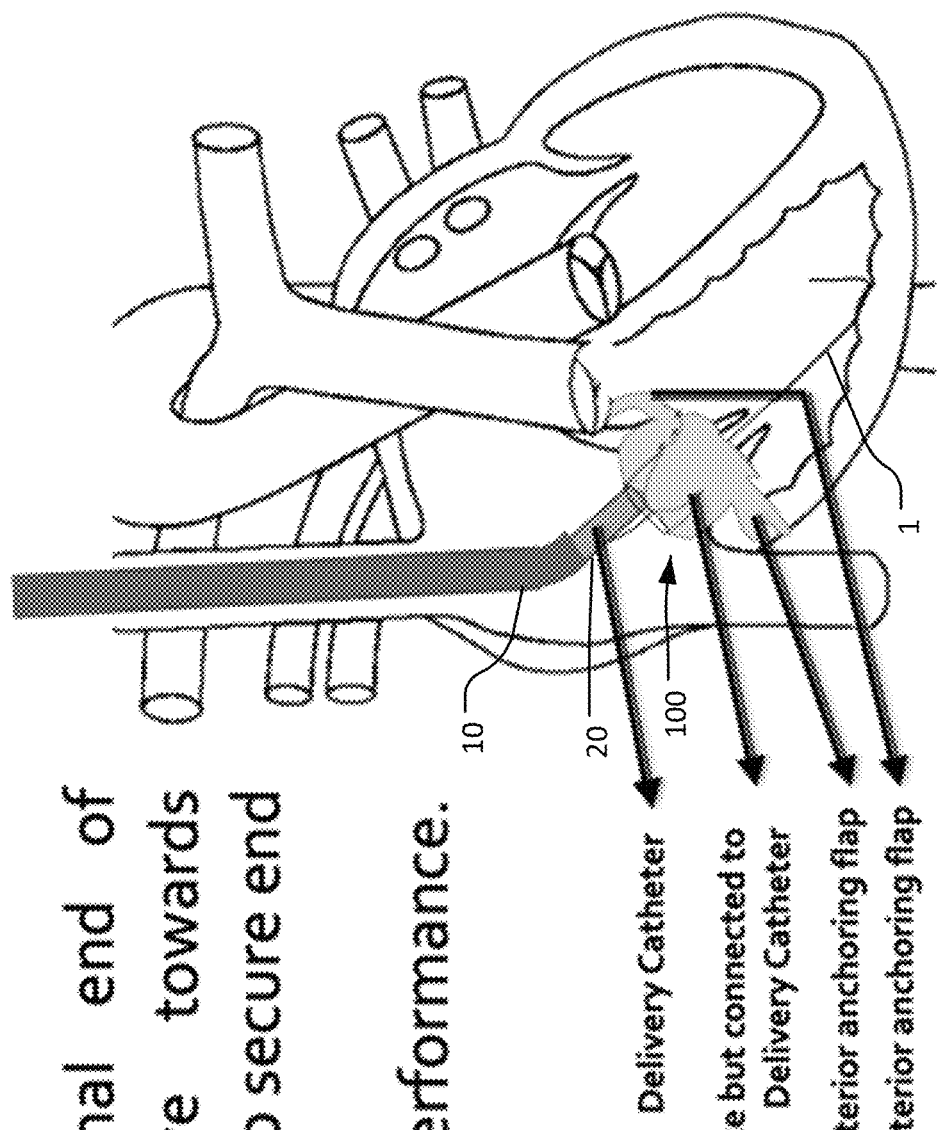
Figure 21:
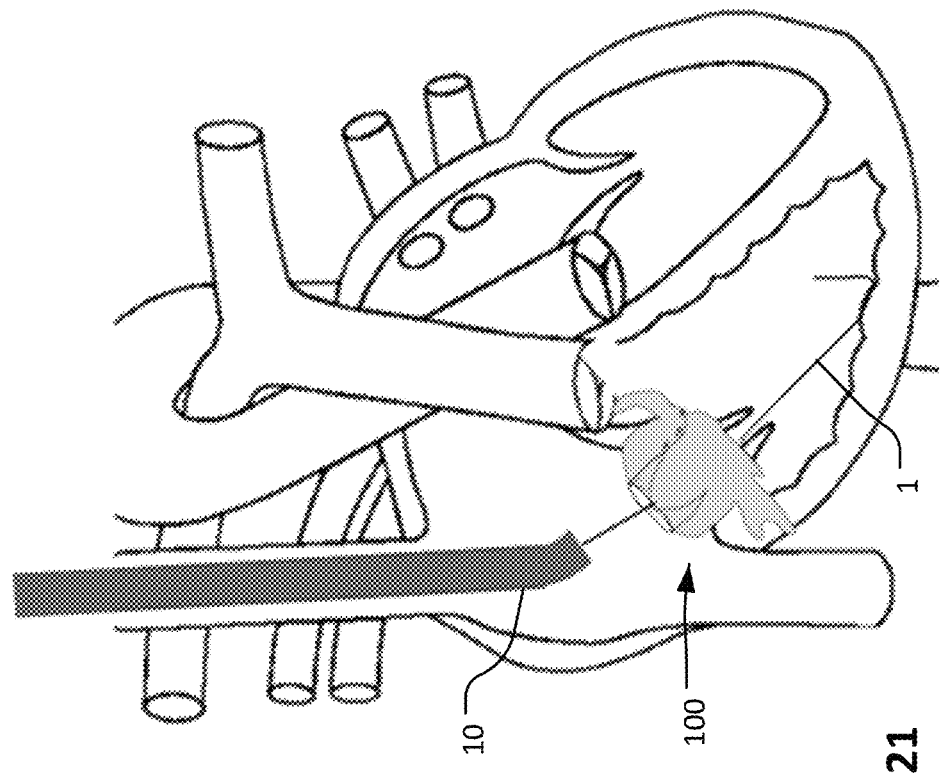

Referring to FIGS. 20 and 21, in some embodiments, the transcatheter valve prosthesis 100 in its functioning state is then unattached from the valve delivery catheter 20 and is deployed.

Figure 22:
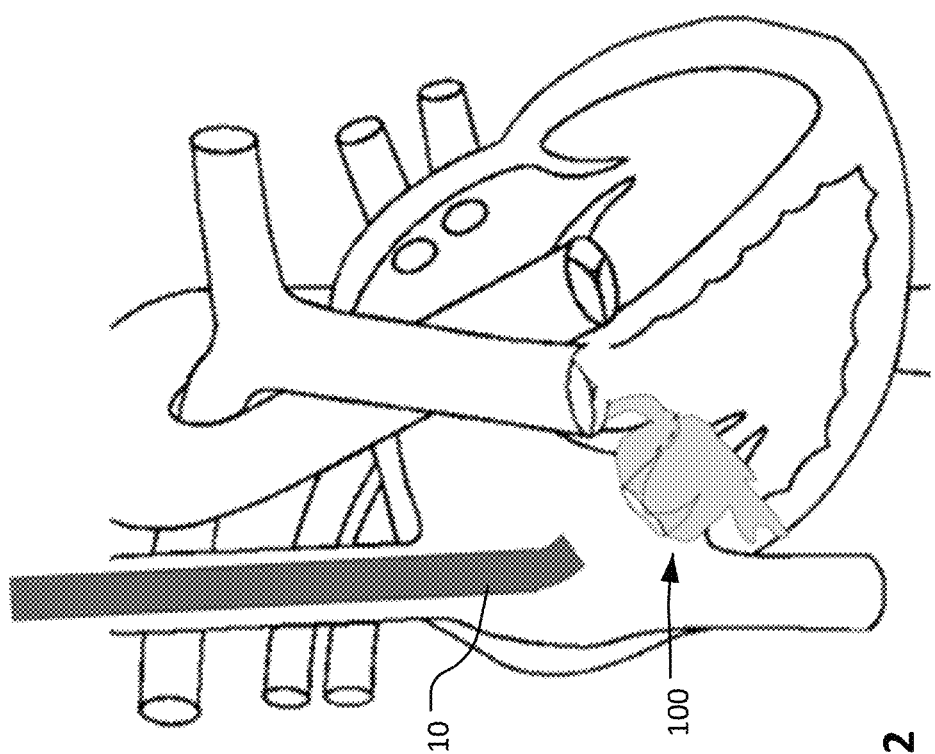
Figure 23:
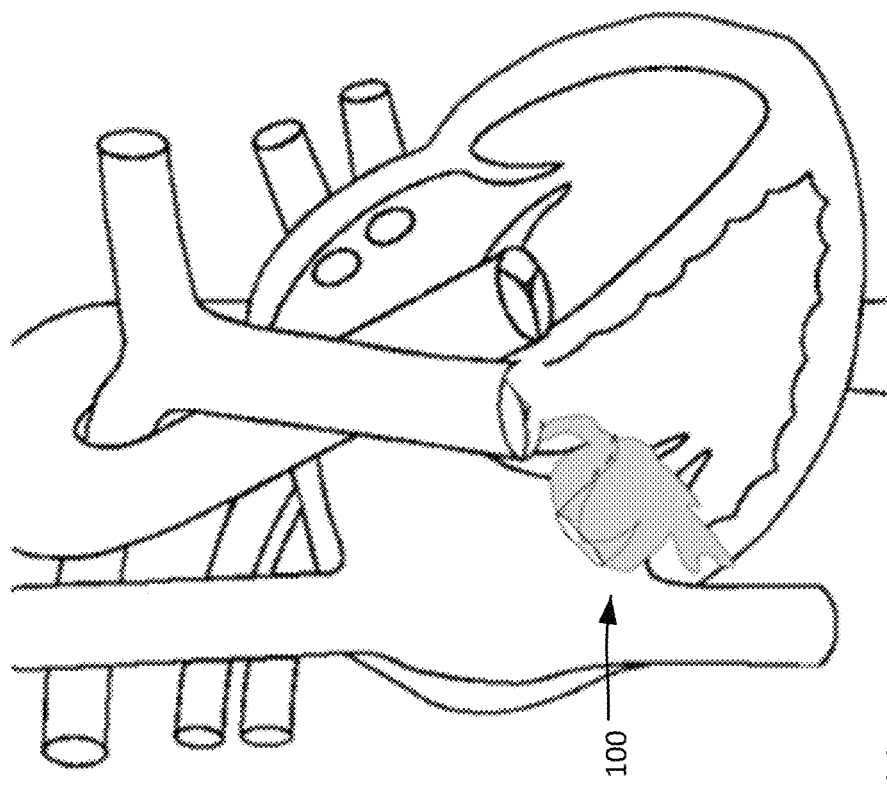

Referring to FIGS. 21, 22 and 23, in some embodiments, the valve delivery catheter 20, guidewire 1 and outer deflectable sheath catheter 10 are all removed from the patient's blood vessel and ultimately fully from the body.

In some other embodiments, the valve delivery catheter 20, guidewire 1, inner steerable and outer deflectable sheath catheter 10 are all removed from the patient's blood vessel and ultimately fully from the body.

5. Additional Embodiments of Transcatheter Prosthetic Valves

FIGS. 24a-24d illustrate another example transcatheter valve prosthesis in accordance with some embodiments provided herein. The depicted example valve prosthesis 200 broadly includes a frame 210, a covering 260, and leaflets 270. In the manner of the example valve prosthesis described above in the context of FIGS. 4D, 5D, and 8D, the occluder portion of the valve prosthesis 200 is tubular (both during delivery and thereafter), while other portions of the valve prosthesis 200 are not tubular (e.g., anchoring flaps).

Figure 24B:
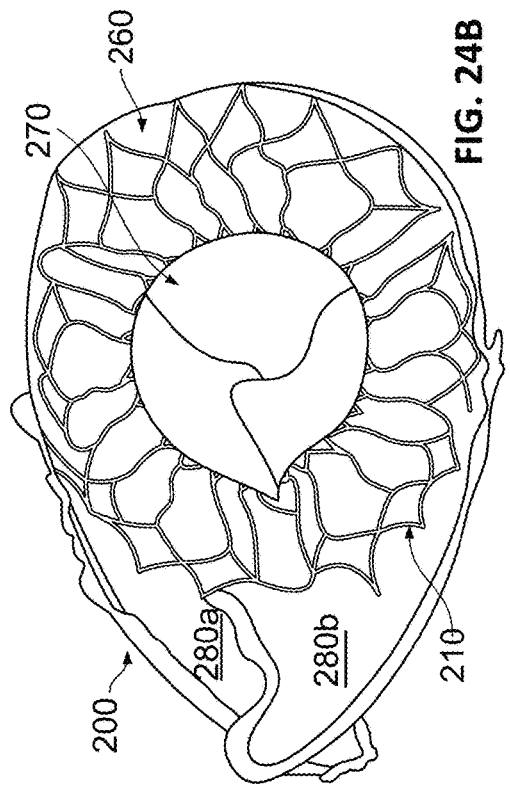
FIGS. 24a-24d show various views of another example transcatheter valve prosthesis device in accordance with some embodiments.
Figure 24D:
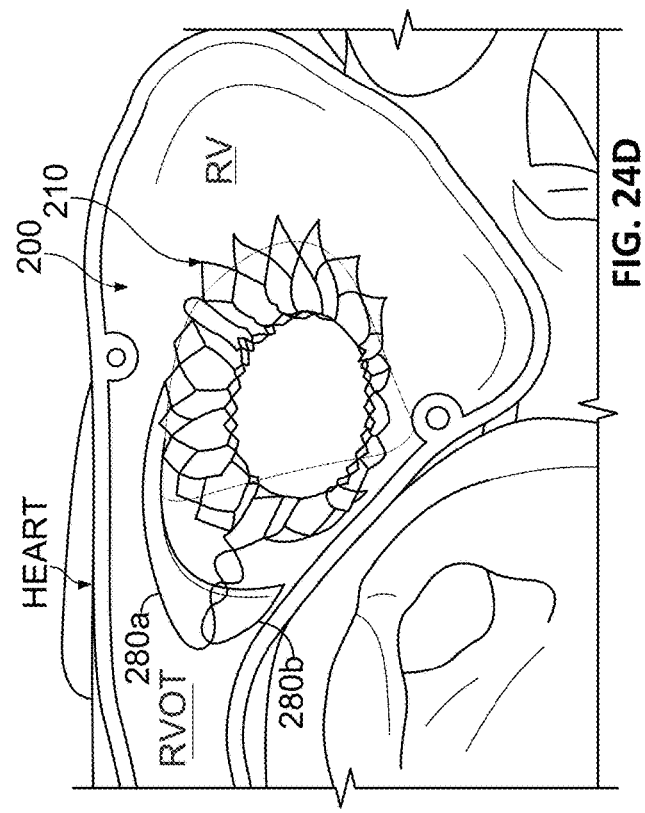

The valve prosthesis 200 can be implanted in various locations within the human body including, but not limited to, a native tricuspid valve location, for example. In such a case, the smaller diameter end of the valve prosthesis 200 is positioned in the right atrium and the larger, flared end is positioned in the right ventricle (RV). For example, FIG. 24d shows a view of the valve prosthesis 200 (without the covering 260) implanted in a simulated heart. The perspective of the view is in the RV looking superiorly toward the right atrium (via the native tricuspid valve). The right ventricular outflow tract (RVOT) is also visible. The RVOT is the portion of the RV where blood being expelled from the RV travels toward the pulmonary valve on its way to the lungs.

The leaflets 270 and the surrounding portions of the frame 210 to which the leaflets 270 are attached make up the occluder portion of the valve prosthesis 200. For example, the frame 210 defines a circular inlet 212 where the edges of leaflets 270 are attached to the frame 210. Other side edges of the leaflets 270 are attached to posts of the frame 210. The leaflets 270 also have distal free edges that are coapable with each other to facilitate the opening and sealing of the one-way valve prosthesis 200.

Figure 24A:
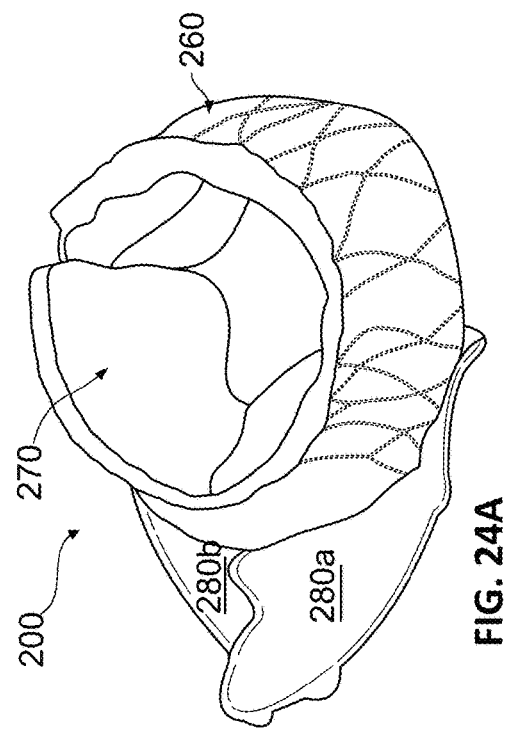
Figure 24C:
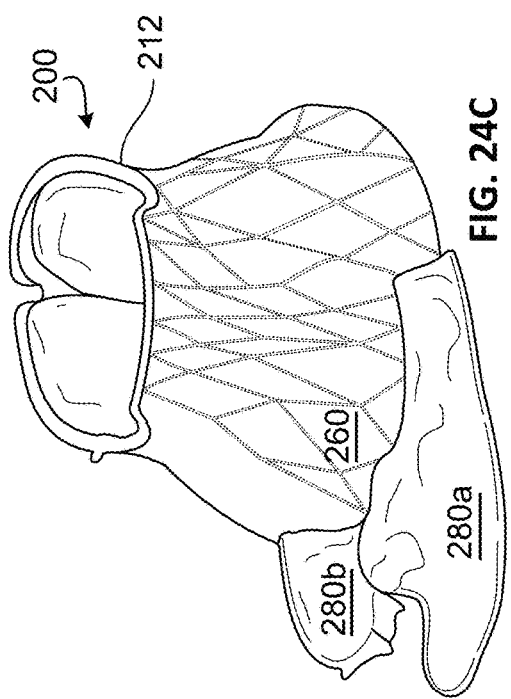

In the depicted embodiment, the valve prosthesis 200 includes a first anterior anchoring flap 280a and a second anterior anchoring flap 280b. The first and second anterior flaps 280a-b are near to each other (even overlapping in some cases), but are distinctly separate from each other. That is, two different, separate portions of the frame 210 provide individual structural support to each of the first and second anterior flaps 280a-b, and separate portions of the covering 260 are attached on the first and second anterior flaps 280a-b. Accordingly, the first and second anterior flaps 280a-b are separate from each other (e.g., see FIG. 24c), and can be wrapped onto or over each other in the collapsed delivery configuration to advantageously facilitate a lower profile of the valve prosthesis 200 in the collapsed delivery configuration. However, in the deployed natural shape orientations of the first and second anterior flaps 280a-b (as shown in FIGS. 24a, 24b, and 24d), both of the first and second anterior flaps 280a-b extend laterally from the main body of the valve prosthesis 200 in the same direction. Accordingly, the first and second anterior flaps 280a-b are, when deployed, adjacent to each other or overlap each other. While the depicted embodiment includes two anterior flaps, in some embodiments one, three, four, or more than four anterior flaps can be included.

In some cases, a patient may have a pacemaker lead passing through the tricuspid valve. Such a pacemaker lead can, in some cases, advantageously pass between the first and second anterior flaps 280a-b. Accordingly, the valve prosthesis 200 can facilitate the pass-through of the pacemaker lead while still providing sealing to prevent tricuspid valve regurgitation from the RV to the right atrium.

The first and second anterior flaps 280a-b form a part of the skirt portion of the valve prosthesis 200 that, along with the occluder portion of the valve prosthesis 200, interfaces with the native tricuspid valve to fill, cover, and/or seal the opening defined by the native tricuspid valve. For example, in FIG. 24d it can be seen that the overlapping first and second anterior flaps 280a-b will, at least in some implementations, cover or seal an anterior portion of the opening defined by the native tricuspid valve. That is the case because, while the main body of the valve prosthesis 200 is essentially circular in cross-section, the opening defined by the native tricuspid valve is not circular. In other words, in combination with the main body of the valve prosthesis 200 (which has a circular cross-sectional shape), the laterally-extending first and second anterior flaps 280a-b help to cover and fluidly seal the native tricuspid valve opening which is not circular (e.g., with the opening being oblong, or irregularly shaped).

The first and second anterior flaps 280a-b extend into the RVOT and thereby help to anchor the valve prosthesis 200 with respect to the RVOT (e.g., see FIG. 24d). That is, the first and second anterior flaps 280a-b extend laterally from the main body of the valve prosthesis 200 and into the RVOT region of the RV. The first and second anterior flaps 280a-b contact the wall of the RV in the RVOT region to anchor the valve prosthesis 200 in place, and to provide migration resistance. For example, during contraction of the RV, the first and second anterior flaps 280a-b become pressed against the wall of the RVOT to help prevent the valve prosthesis 200 from being pushed into the right atrium because of the pressure differential between the RV and right atrium during contraction of the RV.

The first and second anterior flaps 280a-b extend into the RVOT and overlap one axially on top of the other. This arrangement is functionally akin to a cantilevered beam arrangement. With the first and second anterior flaps 280a-b overlapping on each other, the bending resistance of the first and second anterior flaps 280a-b is increased (as compared to a single flap or non-overlapping flaps). This arrangement enables an advantageous extent of rigidity, without having to use framework members that are larger in cross-section. That is, the overlapping arrangement of the first and second anterior flaps 280a-b allow for the use of smaller framework members, which in turn importantly allows for a smaller collapsed delivery size (diameter). In other words, overlapping arrangement of the first and second anterior flaps 280a-b provides a support structure that is thicker without having to use a tubing with higher wall thickness (from which the framework is created); ultimately providing the bending stiffness or rigidity that potentially keeps the valve prosthesis 200 stable when RV pressure acts on the device.

In some embodiments, such as the depicted embodiment, the first and second anterior flaps 280a-b comprise minimal frame members. For example, as best visible in FIG. 24d, the frame 210 comprising the the first and second anterior flaps 280a-b is only made up of peripheral frame members that extend from the frame 210 of the main body. This minimal framework means the first and second anterior flaps 280a-b have a low amount of metal, which advantageously minimizes the potential for adverse effects such as, but not limited to, hemolysis.

FIGS. 25a-25d illustrate another example transcatheter valve prosthesis in accordance with some embodiments provided herein. The depicted example 300 broadly includes a frame 310, a covering 360, and leaflets 370. In the manner of the example valve prosthesis described above in the context of FIGS. 4D, 5D, and 8D, the occluder portion of the valve prosthesis 300 is tubular (both during delivery and thereafter), while other portions of the valve prosthesis 300 are not tubular (e.g., the anchoring flaps that extend anteriorly and posteriorly).

Figure 25A:
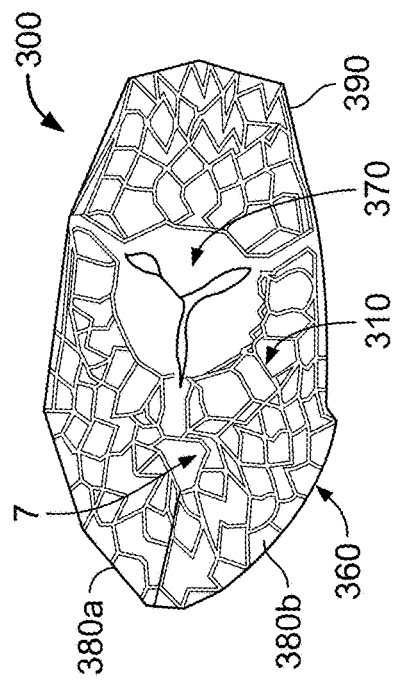
FIGS. 25a-25f show various views of another example transcatheter valve prosthesis device in accordance with some embodiments.
Figure 25B:
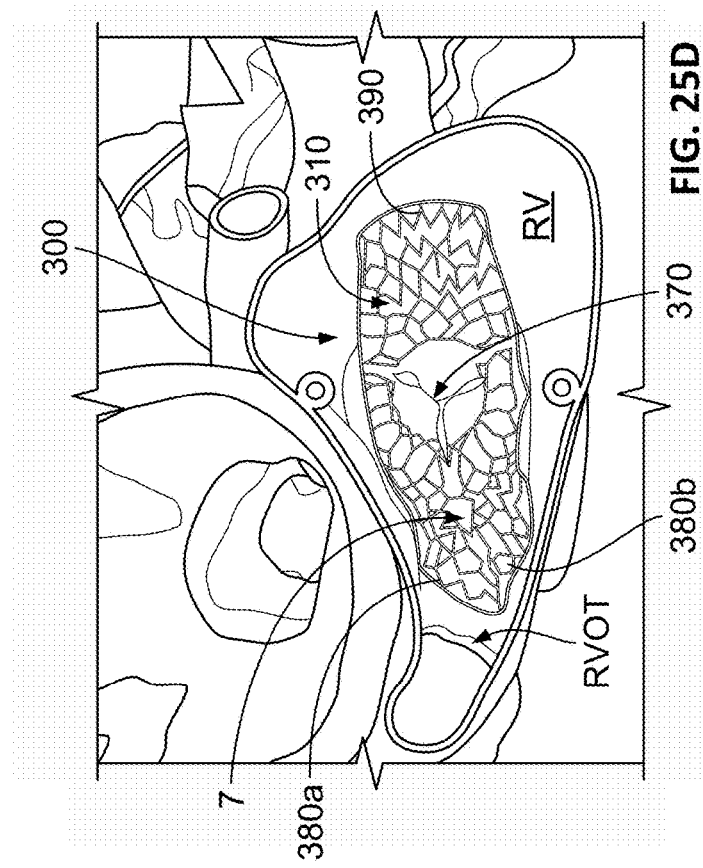
Figure 25C:
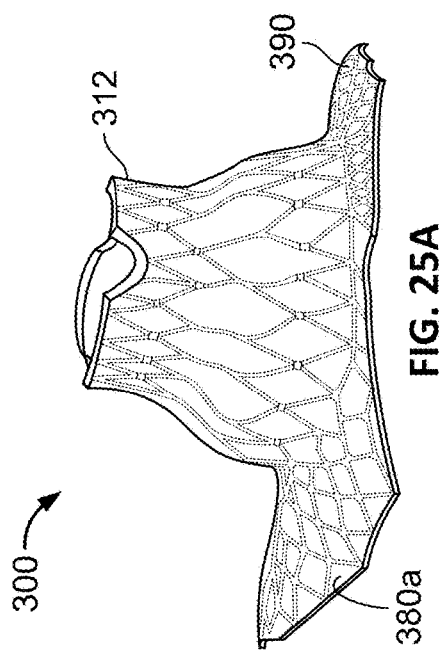
Figure 25D:
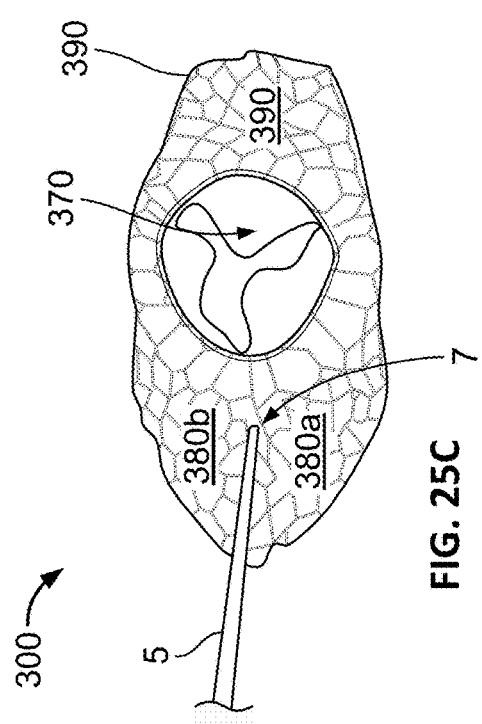

The valve prosthesis 300 can be implanted in various locations within the human body including, but not limited to, a native tricuspid valve location, for example. In such a case, the smaller diameter end of the valve prosthesis 300 is positioned in the right atrium and the larger, flared end is positioned in the right ventrical (RV). For example, FIG. 25d shows a view of the valve prosthesis 300 (without the covering 360) implanted in a simulated heart. The perspective of the view is in the RV looking superiorly toward the right atrium (via the native tricuspid valve). The RVOT is also visible. The RVOT is the portion of the RV where blood being expelled from the RV travels toward the pulmonary valve on its way to the lungs.

The leaflets 370 and the surrounding portions of the frame 310 to which the leaflets 370 are attached make up the occluder portion of the valve prosthesis 300. For example, the frame 310 defines a circular inlet 312 where the edges of leaflets 370 are attached to the frame 310. Other side edges of the leaflets 370 are attached to posts of the frame 310. The leaflets 370 also have distal free edges that are coapable with each other to facilitate the opening and sealing of the one-way valve prosthesis 300.

In the depicted embodiment, the valve prosthesis 300 includes multiple sealing and anchoring flaps that become positioned in the RV when the valve prosthesis 300 is implanted in a native tricuspid valve. For example, the valve prosthesis 300 includes a first anterior anchoring flap 380a, a second anterior anchoring flap 380b, and a posterior anchoring flap 390.

The first and second anterior flaps 380a-b are near to each other (even overlapping in some cases), but are distinctly separate from each other. That is, two different, separate portions of the frame 310 provide individual structural support to each of the first and second anterior flaps 380a-b, and separate portions of the covering 360 are attached on the first and second anterior flaps 380a-b. Accordingly, the first and second anterior flaps 380a-b are separate from each other, and can be wrapped onto or over each other in the collapsed delivery configuration to advantageously facilitate a lower profile of the valve prosthesis 300 in the collapsed delivery configuration. However, in the deployed natural shape orientations of the first and second anterior flaps 380a-b (as shown in FIGS. 25a-d), both of the first and second anterior flaps 380a-b extend laterally from the main body of the valve prosthesis 300 in the same direction. Accordingly, the first and second anterior flaps 380a-b are, when deployed, adjacent to each other or overlap each other. While the depicted embodiment includes two anterior flaps, in some embodiments one, three, four, or more than four anterior flaps can be included.

In some cases, a patient may have a pre-existing pacemaker lead passing through the tricuspid valve at the time that the valve prosthesis 300 is implanted in the tricuspid valve. The configuration of the valve prosthesis 300 with its separate first and second anterior flaps 380a-b can advantageously allow the valve prosthesis 300 to be implanted without needing to remove such a pre-existing pacemaker lead. Instead, the pre-existing pacemaker lead can, in some cases, be positioned to advantageously pass between the first and second anterior flaps 380a-b (e.g., see FIG. 25c which shows a pacemaker lead 5 passing between the first and second anterior flaps 380a-b). The pacemaker lead 5 can pass through an area between the first and second anterior flaps 380a-b that can be referred to as the lead insertion zone 7 (see FIGS. 25b-d). The first and second anterior flaps 380a-b can be wrapped around the pre-existing pacemaker lead. Accordingly, the valve prosthesis 300 can facilitate the pass-through of the pacemaker lead while still providing sealing to prevent tricuspid valve regurgitation from the RV to the right atrium.

The lead insertion zone 7 defined between the first and second anterior flaps 380a-b can also advantageously accommodate a future installation of a pacemaker lead at a point in time after the valve prosthesis 300 has been implanted in the tricuspid valve. In such a case, the pacemaker lead can be advanced through the lead insertion zone 7 so that the pacemaker lead is extending through the valve prosthesis 300 between the first and second anterior flaps 380a-b.

The first and second anterior flaps 380a-b and the posterior anchoring flap 390 form a part of the skirt portion of the valve prosthesis 300 that, along with the occluder portion of the valve prosthesis 300, interfaces with the native tricuspid valve to fill, cover, and/or seal the opening defined by the native tricuspid valve. For example, in FIG. 25d it can be seen that the overlapping first and second anterior flaps 380a-b and the posterior anchoring flap 390 will, at least in some implementations, cover or seal the anterior and posterior portions of the opening defined by the native tricuspid valve. That is the case because, while the main body of the valve prosthesis 300 is essentially circular in cross-section, the opening defined by the native tricuspid valve is not circular. In other words, in combination with the main body of the valve prosthesis 300 (which has a circular cross-sectional shape), the first and second anterior flaps 380a-b and the laterally-extending posterior anchoring flap 390 help to cover and fluidly seal the native tricuspid valve opening which is not circular (e.g., with the opening being oblong, or irregularly shaped).

The first and second anterior flaps 380a-b extend into the RVOT and thereby help to anchor the valve prosthesis 300 with respect to the RVOT (e.g., see FIG. 25d). That is, the first and second anterior flaps 380a-b extend laterally from the main body of the valve prosthesis 300 and into the RVOT region of the RV. The first and second anterior flaps 380a-b contact the wall of the RV in the RVOT region to anchor the valve prosthesis 300 in place, and to provide migration resistance. For example, during contraction of the RV, the first and second anterior flaps 380a-b become pressed against the wall of the RVOT to help prevent the valve prosthesis 300 from being pushed into the right atrium because of the pressure differential between the RV and right atrium during contraction of the RV.

The posterior anchoring flap 390 extends laterally from the main body of the valve prosthesis 300. The posterior anchoring flap 390 extends directionally opposite from the extension direction of the first and second anterior flaps 380a-b. In some embodiments, the posterior anchoring flap 390 extends 180° opposite from the extension direction of the first and second anterior flaps 380a-b. While the depicted embodiment includes a single posterior anchoring flap 390, in some embodiments two or more posterior anchoring flap portions can be included (e.g., analogous to the first and second anterior flaps 380a-b).

Figure 25E:
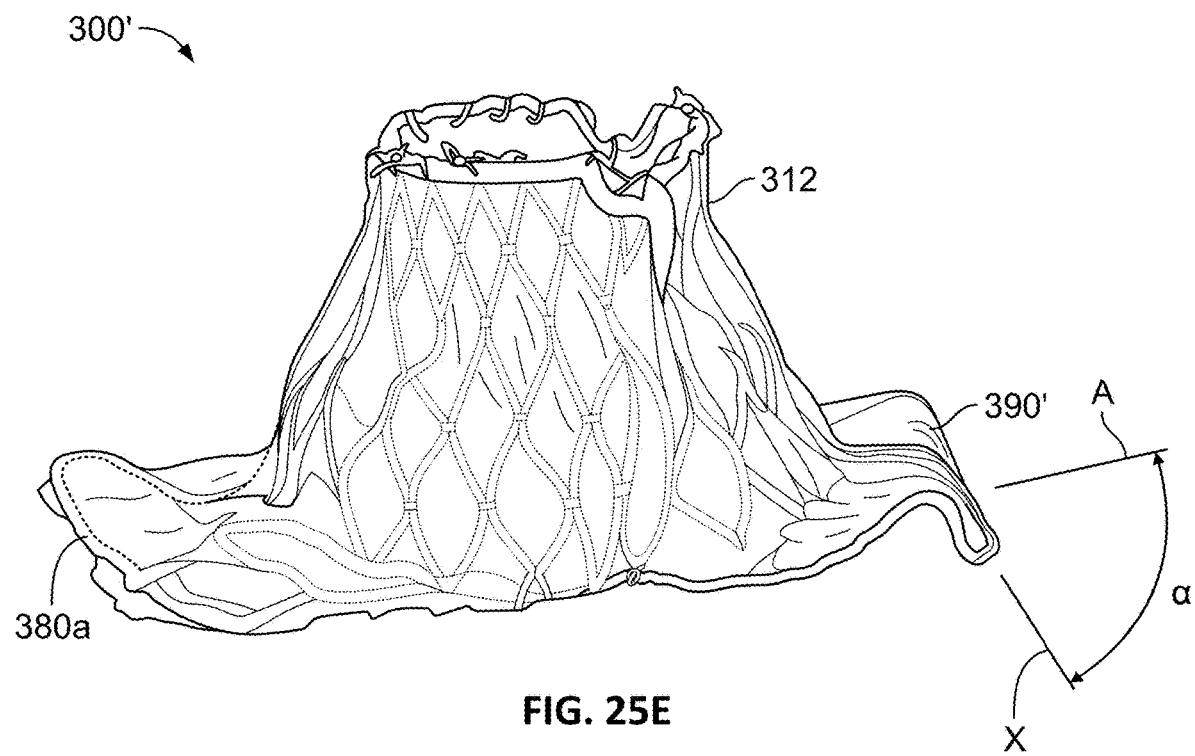
Figure 25F:
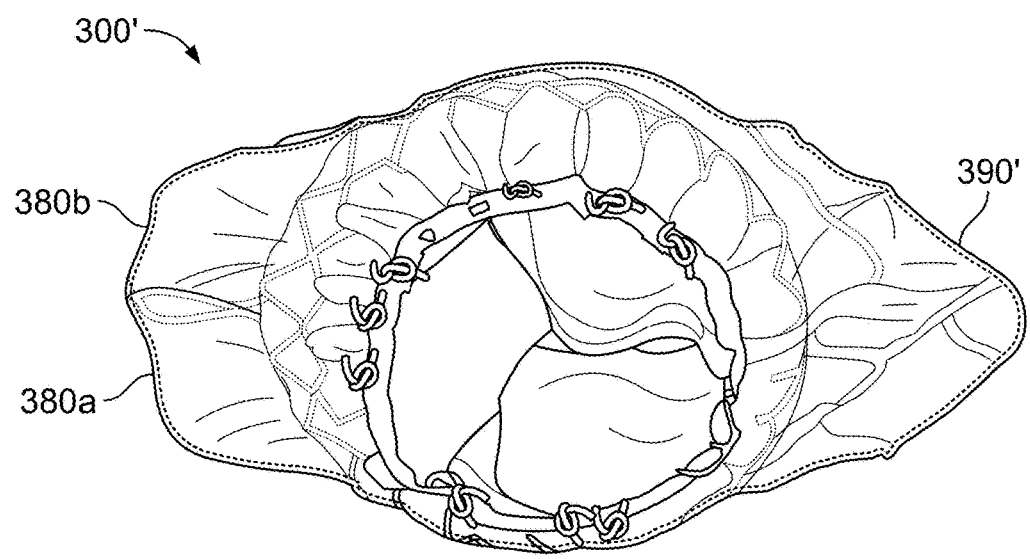

Referring also to FIGS. 25e and 25f, the posterior anchoring flap 390 can be designed with various shapes and arrangements. For example, an example valve prosthesis 300' (which is a variation of the valve prosthesis 300) includes a posterior anchoring flap 390'. The tip or free end portion of the posterior anchoring flap 390' is angled relative to the lateral axis "A" of the main body of the valve prosthesis 300'. The portion of the posterior anchoring flap 390' that extends directly from the main body also extends along the lateral axis "A". However, the distal tip portion of the posterior anchoring flap 390' extends along an axis "X." An angle α is defined between the axes "A" and "X." In some embodiments, the angle α is in a range between 70° to 110°, or 80° to 100°, or 60° to 90°, or 90° to 120°, or 40° to 80°, or 30° to 90°, or 60° to 120°, without limitation.

In some embodiments, having the posterior anchoring flap 390' with the angle α is advantageous because the posterior anchoring flap 390' is thereby made less traumatic to the heart wall. In other words, the angle α of the posterior anchoring flap 390' makes the the posterior anchoring flap 390' conform more closely to the natural anatomical topography of the posterior section of the RV (behind the posterior leaflet of the tricuspid valve) where the posterior anchoring flap 390' ultimately resides.

Still referring to FIGS. 25a-25d, the first and second anterior flaps 380a-b, in combination, are larger than the posterior anchoring flap 390. For example, the first and second anterior flaps 380a-b are wider and extend farther laterally than the posterior anchoring flap 390. While the first and second anterior flaps 380a-b are two distinct members, the posterior anchoring flap 390 is a single, unitary member.

In some embodiments, when the valve prosthesis 300 is in its collapsed delivery configuration within a delivery sheath, the portions of the valve prosthesis 300 are arranged relative to each other as follows. The first and second anterior flaps 380a-b (which can be wrapped on each other) are distal-most. The occluder portion with the three leaflets 370 is proximal-most within the delivery sheath. The posterior anchoring flap 390 is arranged between the distal-most first and second anterior flaps 380a-b and the proximal-most occluder portion.

Figure 26:
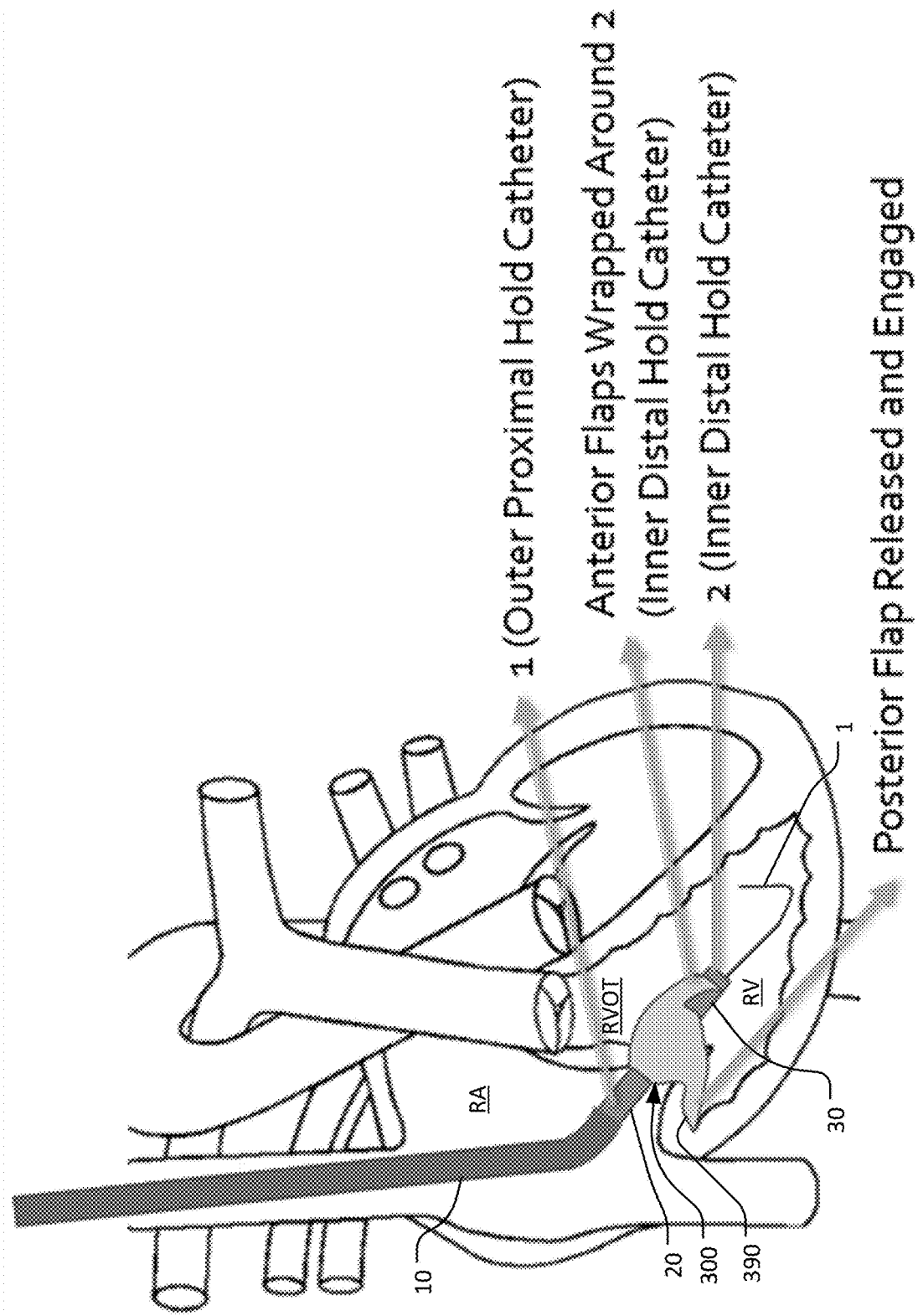
FIGS. 26-33 show a deployment system and sequential method of deploying the transcatheter valve prosthesis device of FIGS. 25a-25d.
Figure 27:
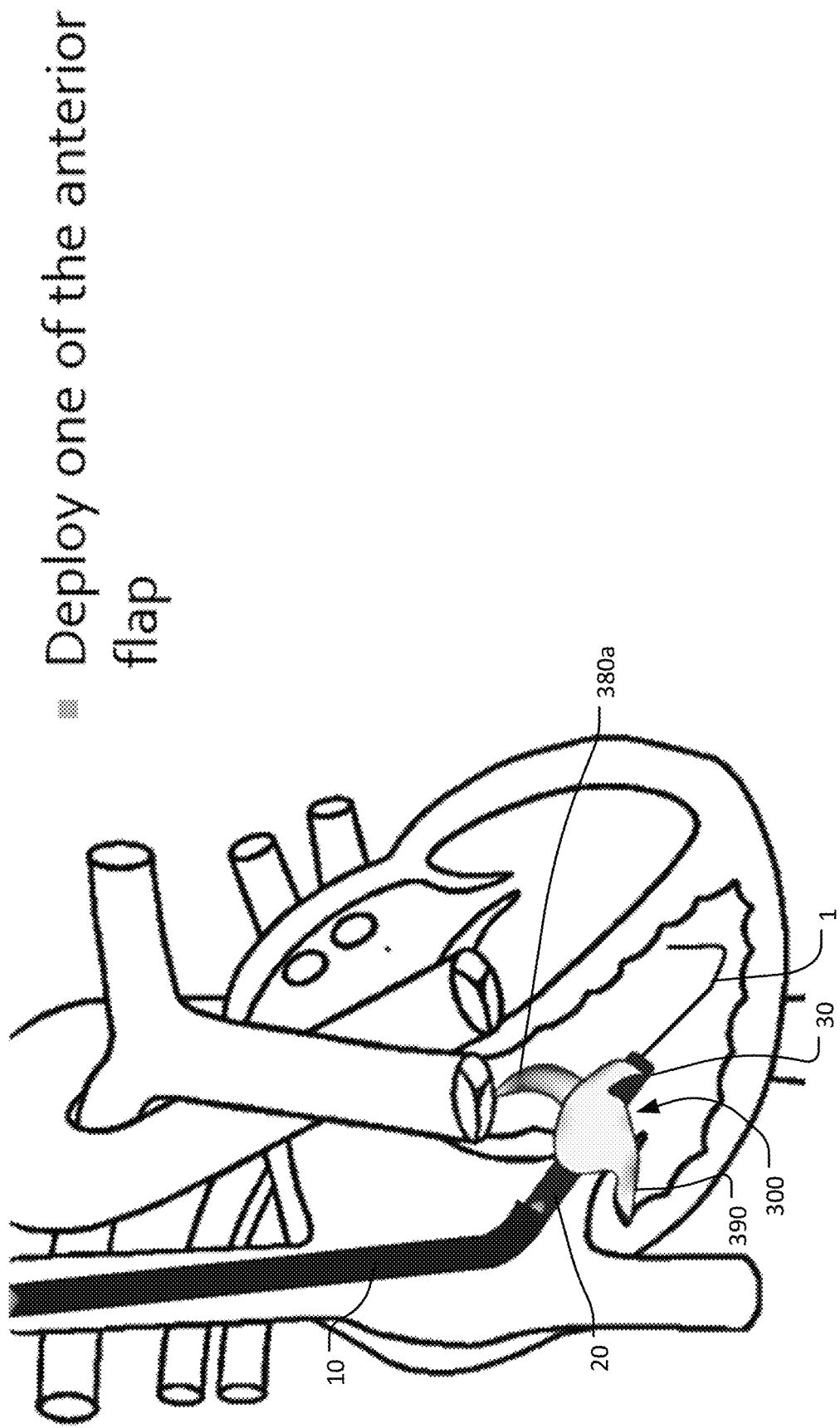
Figure 28:
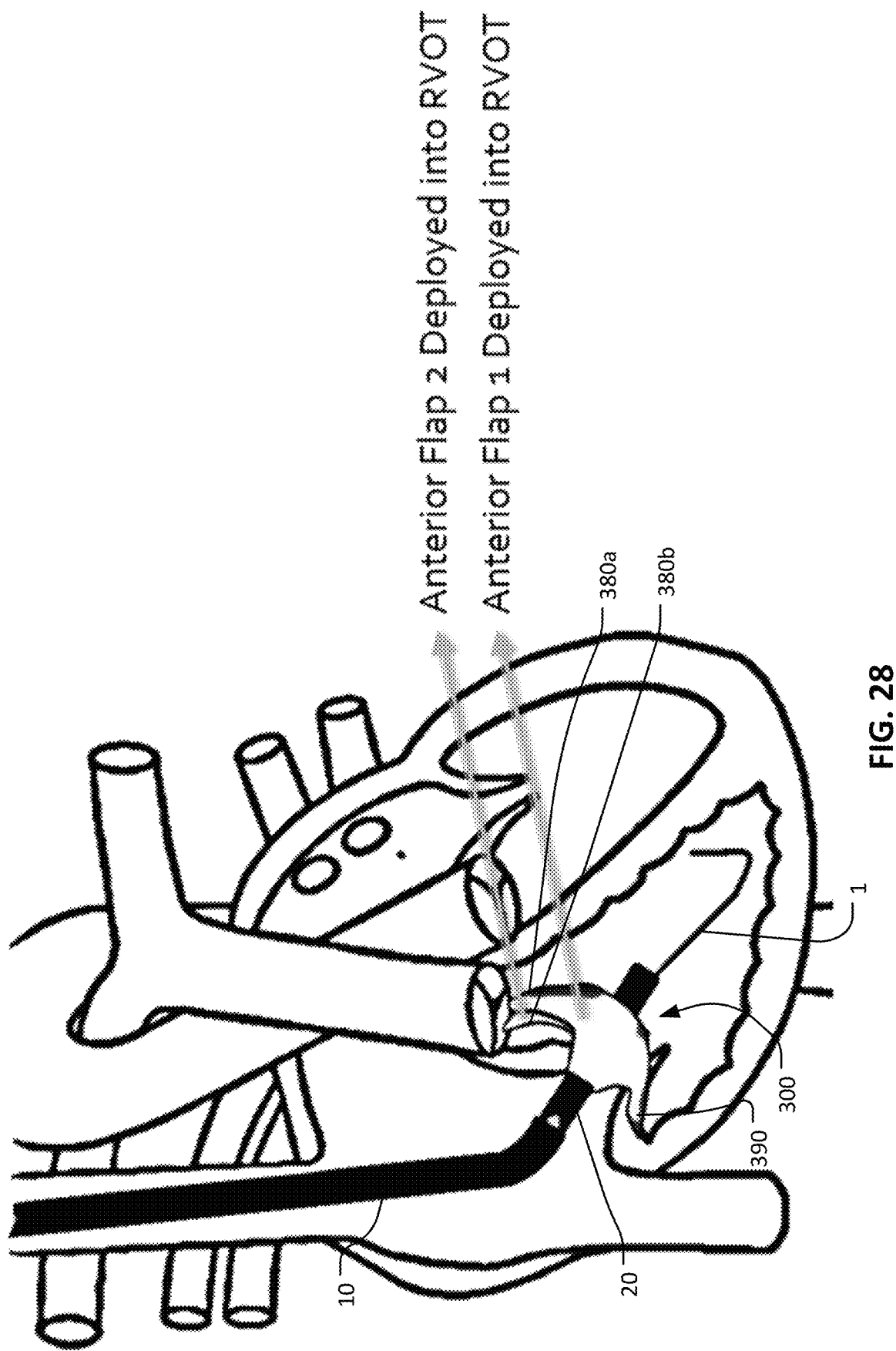
Figure 29:
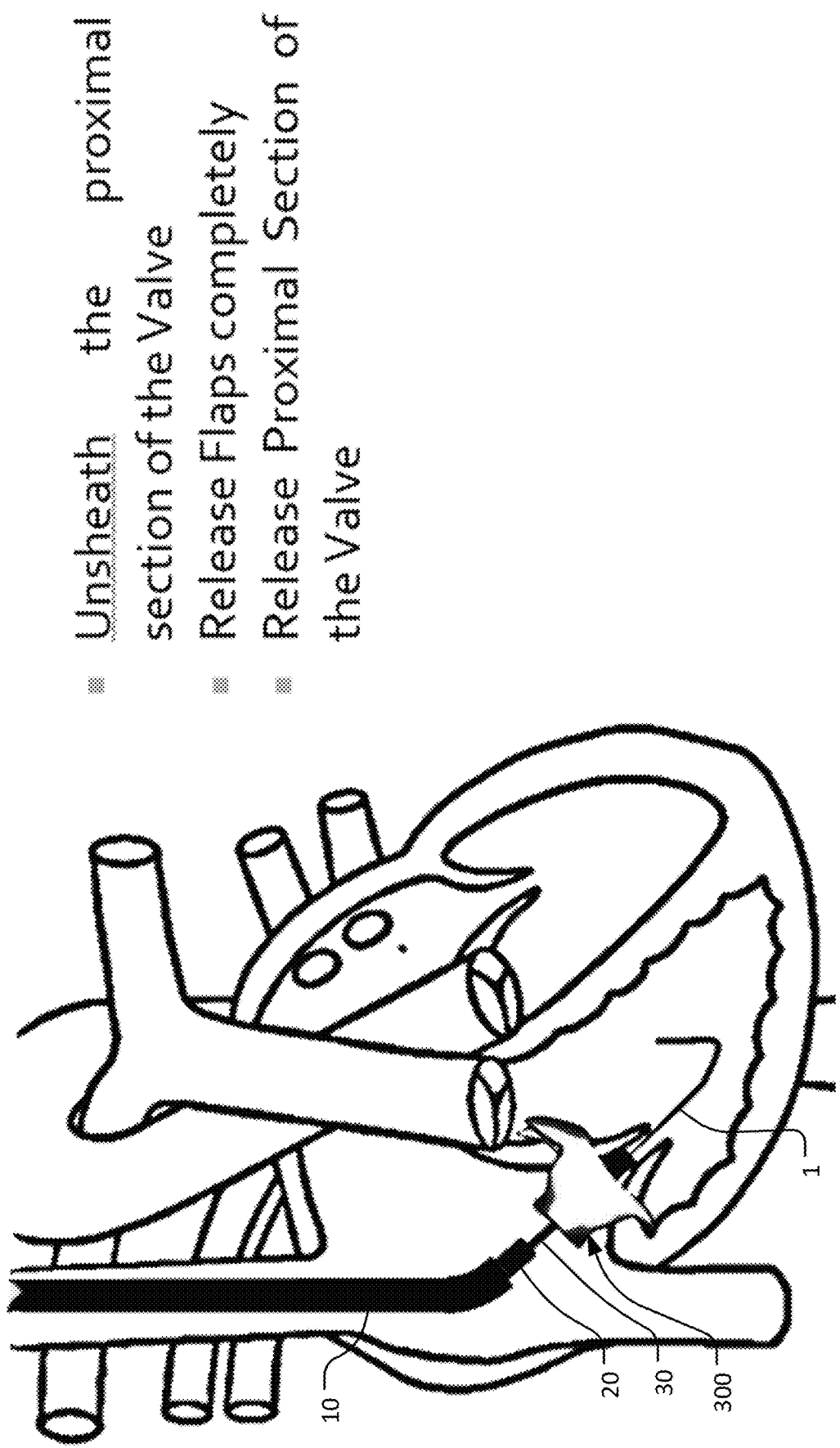
Figure 30:
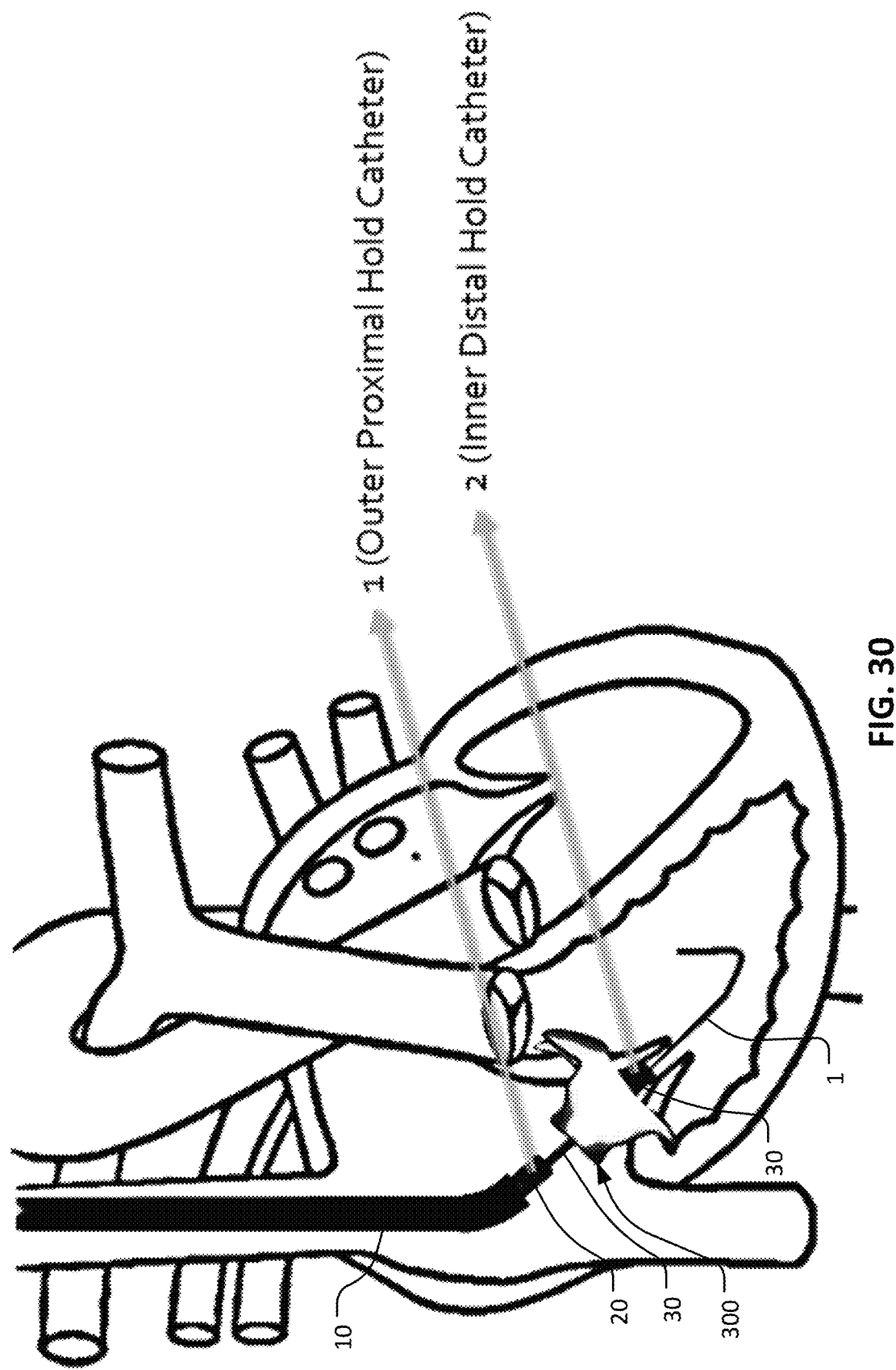
Figure 31:
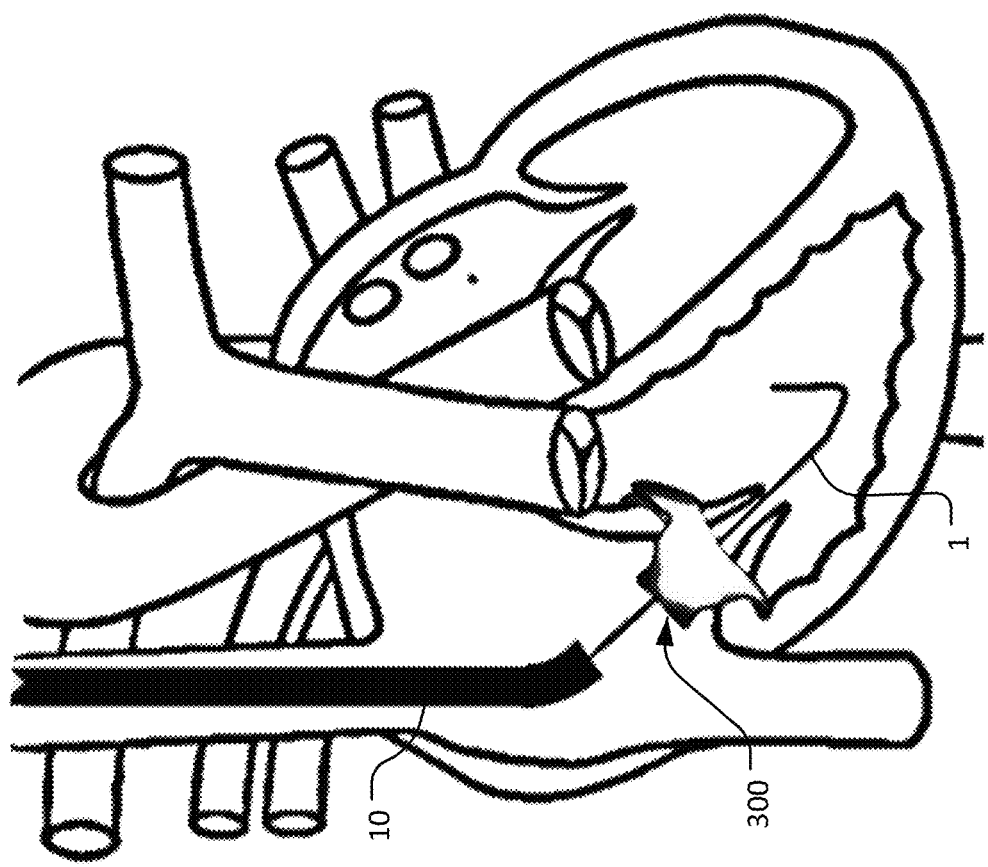
Figure 32:
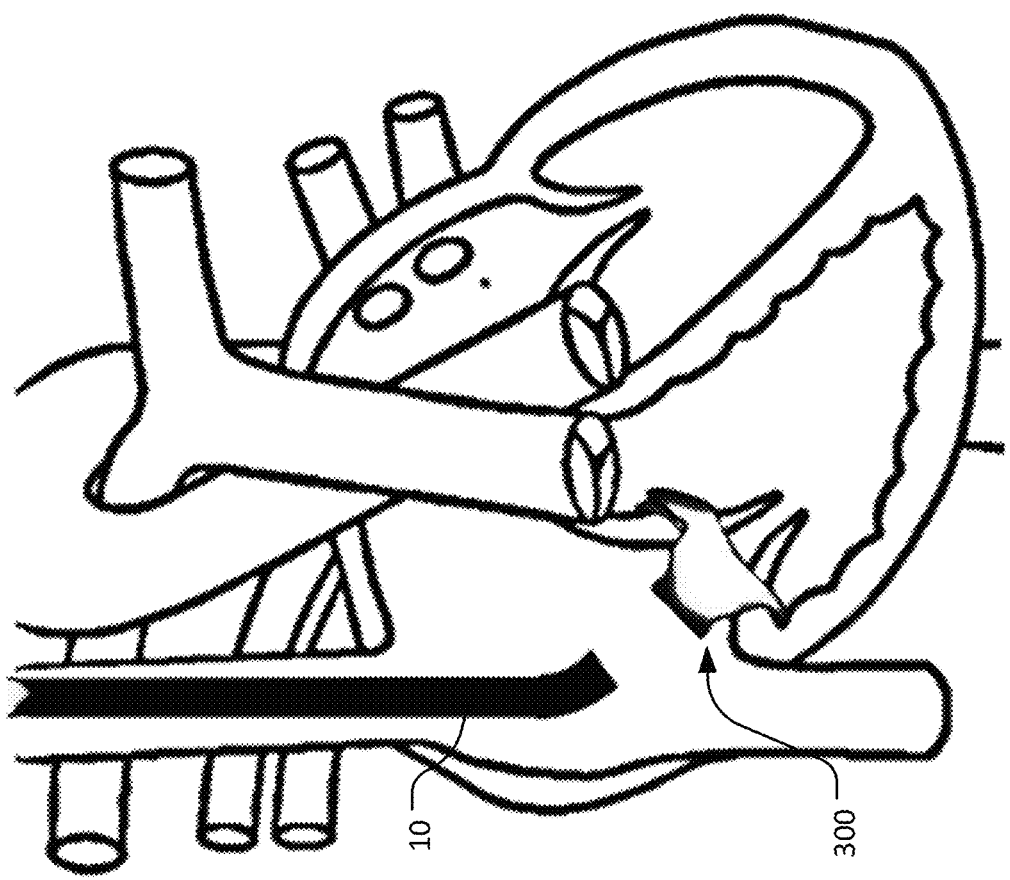
Figure 33:
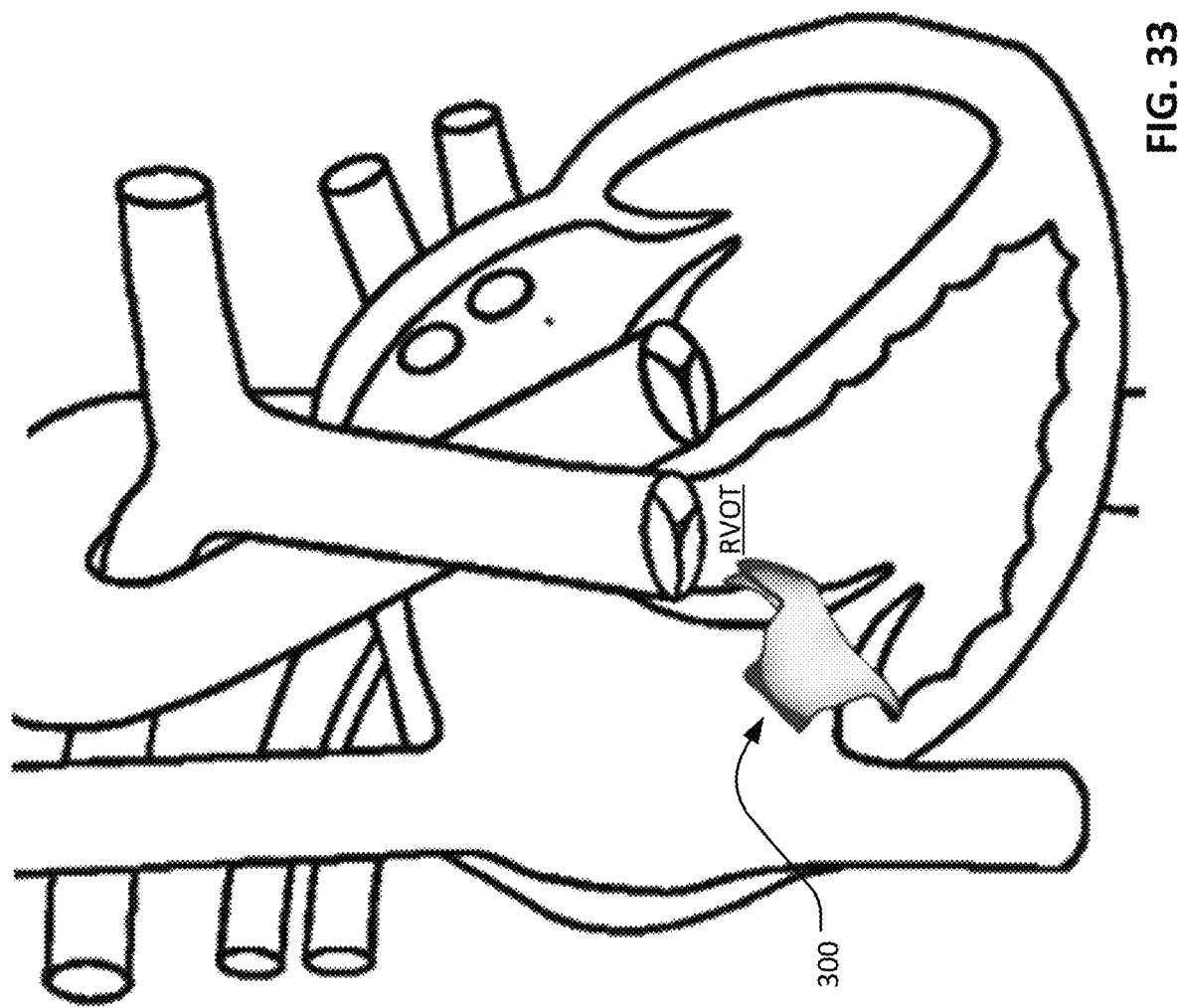

FIGS. 26-33 depict an example sequence for the deployment of the valve prosthesis 300 in a native tricuspid valve site. As depicted by the sequential figures, in some embodiments the posterior anchoring flap 390 is deployed first (see FIG. 26). Then the first and second anterior flaps 380a-b are sequentially deployed into the RVOT (FIGS. 27 and 28). After that, the occluder portion of the valve prosthesis 300 is deployed (FIG. 29). Finally, the deployment system comprising a sheath, outer hold catheter and inner hold catheter are detached from the valve prosthesis 300 and removed from the heart.

As shown in FIG. 26, a sheath catheter 10 containing the valve prosthesis 300 configured in its collapsed delivery configuration is navigated to the right atrium (RA) and superior to the native mitral valve. In some embodiments, a guidewire 1 can be placed first and the sheath catheter 10 containing the valve prosthesis 300 can be advanced over the guidewire 1. The valve prosthesis 300 can be releasably attached to an outer proximal hold catheter 20 and an inner distal hold catheter 30. In some embodiments, the inner distal hold catheter 30 is slidably disposed within the outer proximal hold catheter 20. The first and second anterior flaps 380a-b can be wrapped around the inner distal hold catheter 30 and on each other.

Figure 26A:
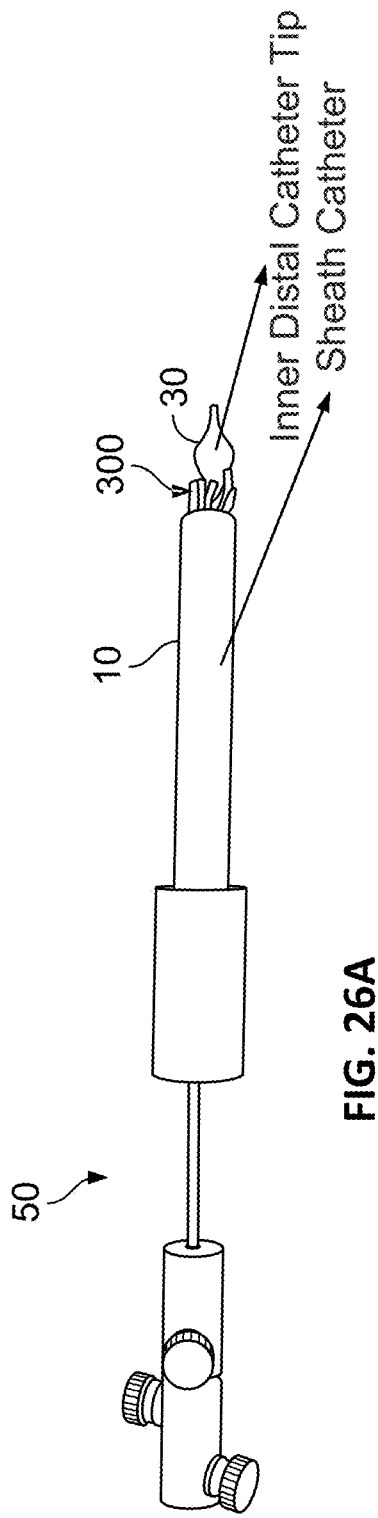
Figure 26B:
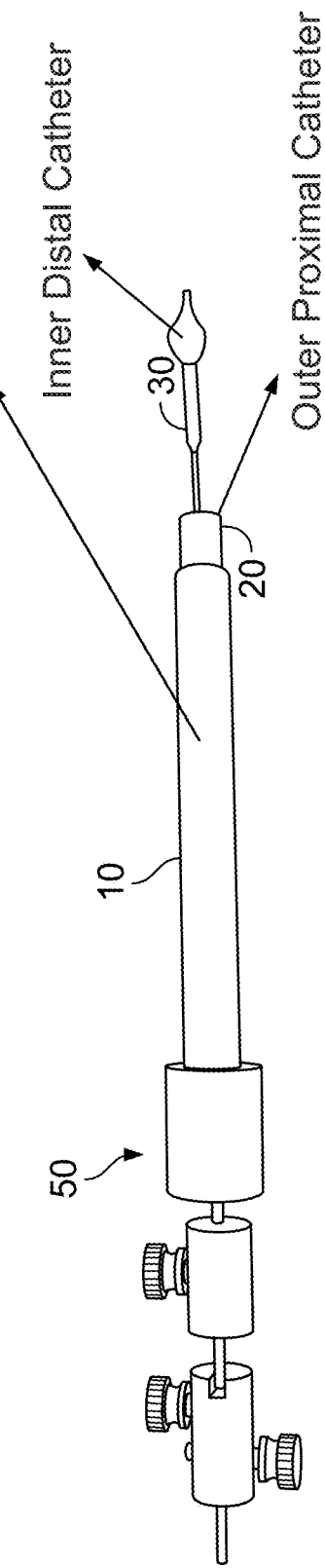

Referring also to FIGS. 26a and 26b, an example deployment system 50 is depicted. It should be understood that the depicted version of the deployment system 50 is not fully representative of the envisioned system that would be used to percutaneously implant the valve prosthesis 300 in a native tricuspid valve site via the patient's vasculature (which can include a groin incision to access the femoral vein and then navigating to enter into the RA via the superior vena cava). In some embodiments, the sheath catheter 10 is steerable in one or more planes. The inner distal catheter 10 is within a lumen of the outer proximal catheter 20, and the outer proximal catheter 20 is within a lumen of the sheath catheter 10.

In some embodiments, the valve prosthesis 300, in its collapsed delivery configuration, can be confined within the lumen of the sheath catheter 10 (e.g., see FIG. 26a), and attached to both the inner distal catheter 10 and the outer proximal catheter 20. For example, the first and second anterior flaps 380a-b can be removably attached to the inner distal catheter 10, and the main body of the valve prosthesis 300 can be removably attached to the outer proximal catheter 20. In some embodiments, the first and second anterior flaps 380a-b can be removably attached to the inner distal catheter 10 by removable sutures (one suture for each of the first and second anterior flaps 380a-b). A clinician can controllably deploy the first and second anterior flaps 380a-b by slacking and then removing the removable sutures. In some embodiments, the main body of the valve prosthesis 300 can be removably attached to the outer proximal catheter 20 by a removable suture. A clinician can controllably deploy the main body of the valve prosthesis 300 by slacking and then removing the removable suture. In some embodiments, the posterior anchoring flap 390 is controllably deployed simply by unsheathing it (no removable suture is necessary). However, in some embodiments the posterior anchoring flap 390 is deployed using a removable suture.

Still referring to FIG. 26, the posterior anchoring flap 390 can be deployed to extend laterally from the main body of the valve prosthesis 300 by retracting the sheath catheter 10.

Referring to FIG. 27, next, one of the anterior flaps can be deployed to extend laterally from the main body of the valve prosthesis 300 and into the RVOT. This can be either the first anterior flap 380a or the second anterior flap 380b. In some embodiments, this is performed by controllably releasing a first suture that is attaching the anterior flap to the inner distal catheter 30.

Referring to FIG. 28, next, the remaining one of the anterior flaps can be deployed to extend laterally from the main body of the valve prosthesis 300 and into the RVOT. In some embodiments, this is performed by controllably releasing a second suture that is attaching the anterior flap to the inner distal catheter 30. Now both of the first and second anterior flaps 380a-b are deployed in the RVOT.

Referring to FIG. 29, the proximal occluder section of the valve prosthesis 300 is unsheathed from the sheath catheter 10. In some embodiments, this is performed by controllably releasing a third suture that is attaching the main body to the outer proximal catheter 20. Now the valve prosthesis 300 begins to function as the patient's tricuspid valve.

Referring to FIGS. 30-33, the delivery system 50 is then detached from the valve prosthesis 300 and removed from the patient. The valve prosthesis 300 remains implanted in/at the patient's tricuspid valve.

Figure 34:
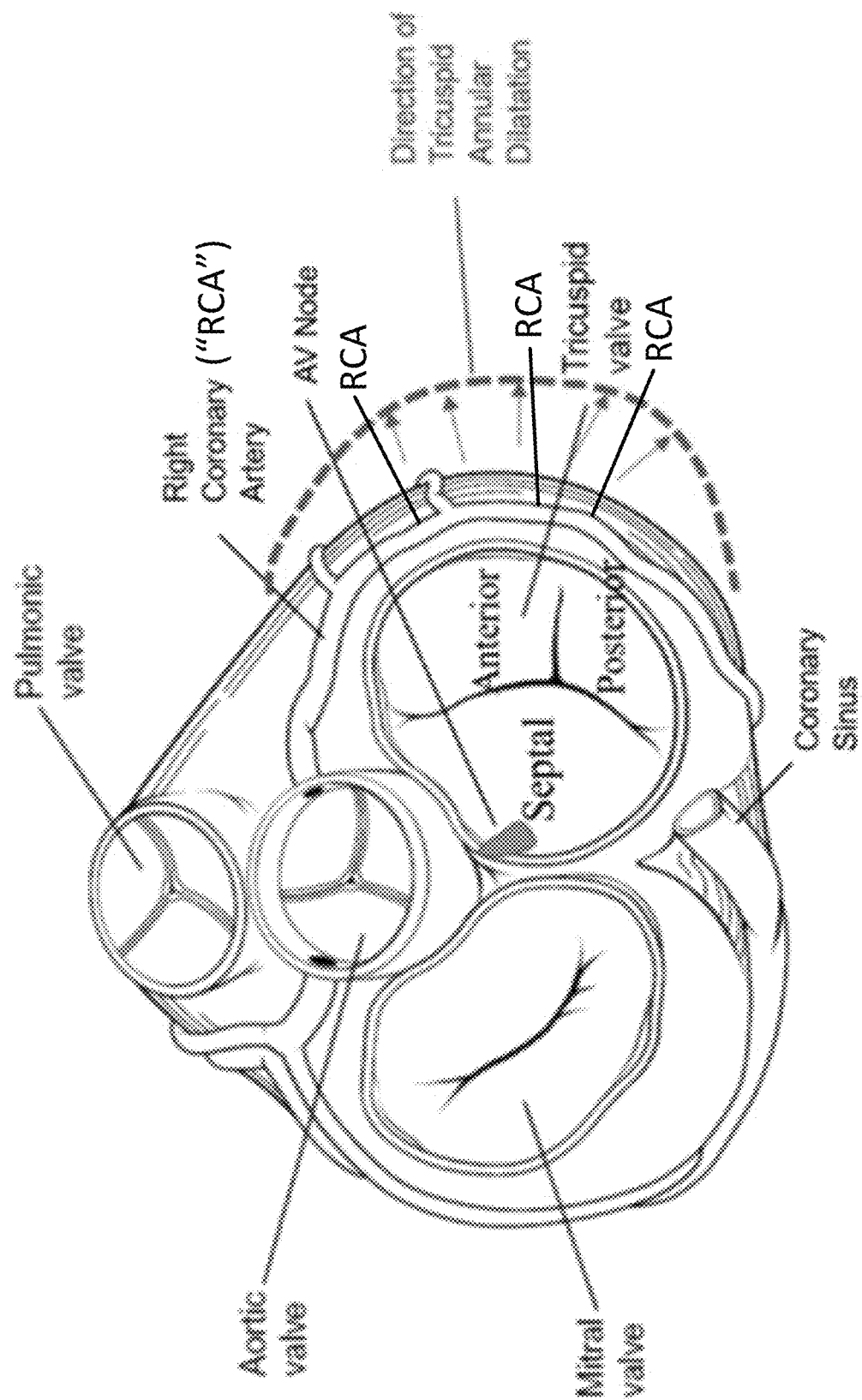
FIGS. 34-36 show that the prosthetic valve devices described herein are atraumatic devices that do not cause restrictions of the coronary arteries.

Referring to FIG. 34, when a prosthetic valve is implanted in the native tricuspid valve, there is a significant potential of causing restrictions of the right coronary artery (RCA). As shown, the RCA surrounds a portion of the tricuspid valve. If the implantation of the prosthetic tricuspid valve distorts certain portions of the native tricuspid valve or adjacent heart walls (e.g., by applying radial force), then the RCA can become restricted as a result. This would be seriously detrimental as the RCA supplies oxygenated blood to portions of the heart muscle to keep the heart viable.

Figure 35:
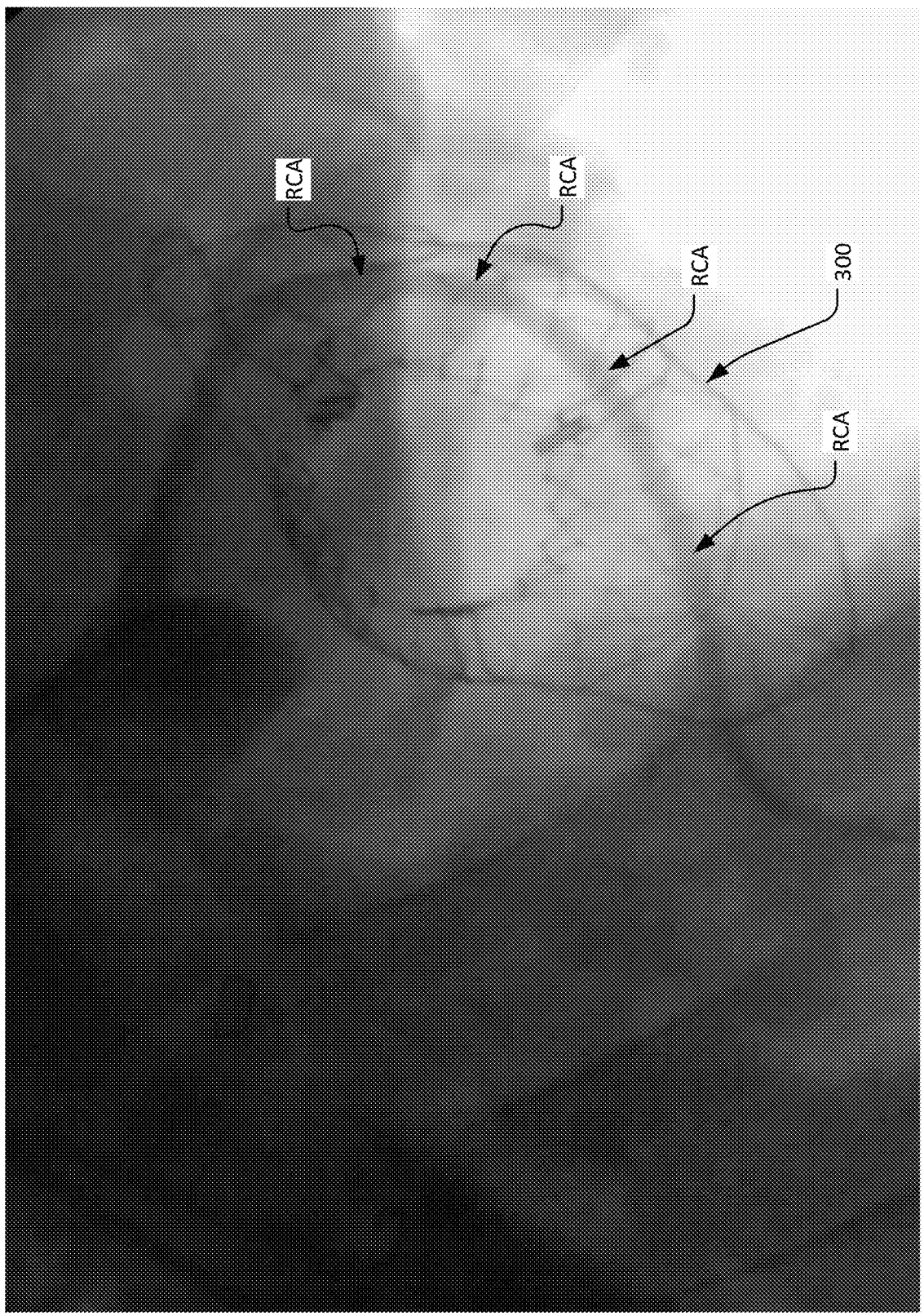
Figure 36:
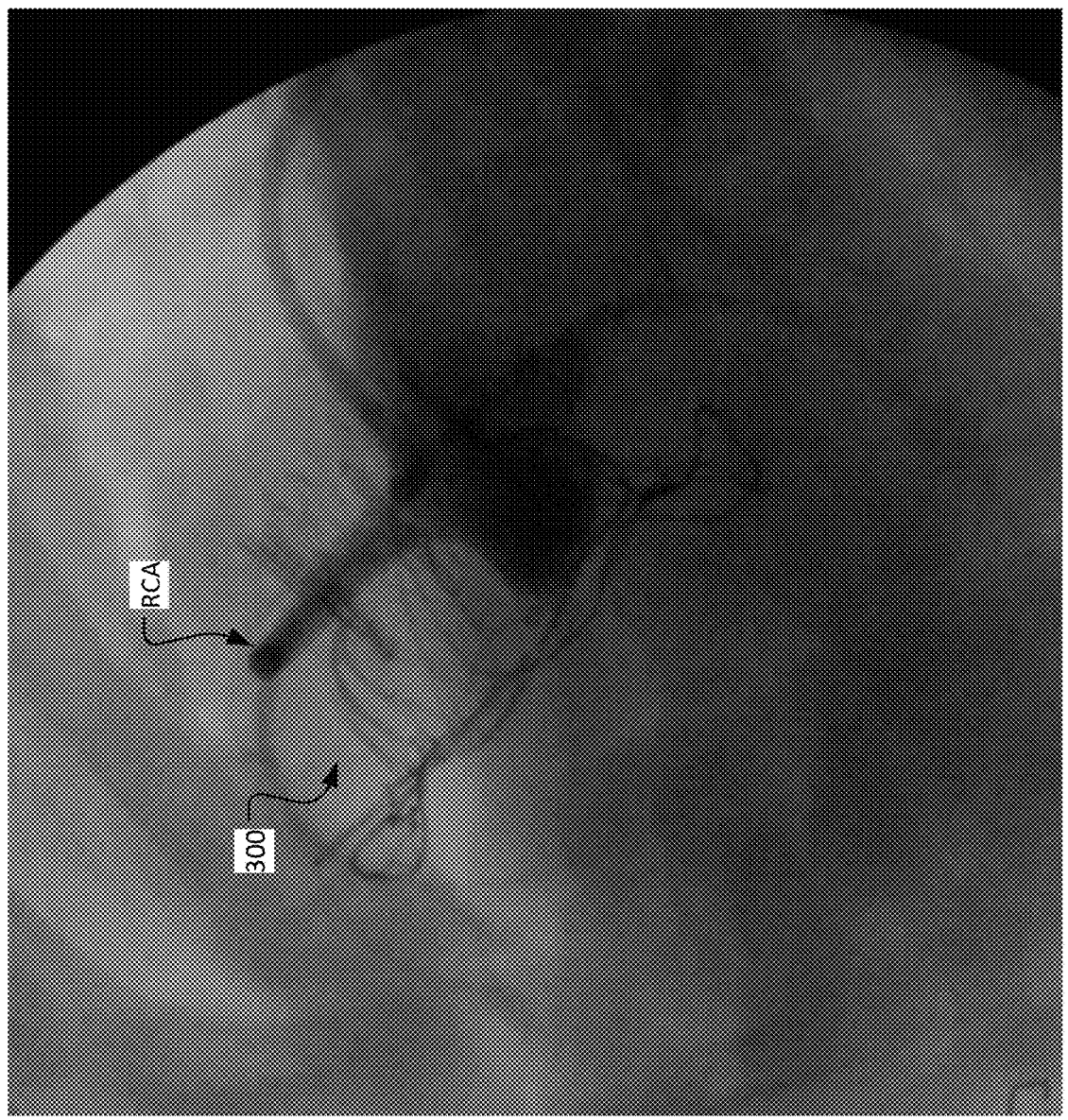

FIGS. 35 and 36 are radiographic (X-ray or fluoroscopic) images showing an implanted prosthetic valve prosthesis 300 (as described above) that has been implanted in a native tricuspid valve site. FIG. 35 shows a top view, and FIG. 36 shows a side view. Due to the radiographic nature of the components of the prosthetic valve prosthesis 300, only the frame is visible on these images. In addition, the RCA is visible. A contrast agent was injected to cause the RCA to be visibly shown in these X-ray images. There images show that the valve prosthesis 300 implanted in a native tricuspid valve advantageously does not cause restriction of the RCA. This is at least in part because the valve prosthesis 300 strategically does not have septal and/or medial anchoring features that can impinge the blood flow through the RCA. Instead, the valve prosthesis 300 has anchoring features in anterior and posterior regions, as described above. Moreover, embodiments having the posterior anchoring flap 390' with the angle α is advantageous because the posterior anchoring flap 390' is thereby made less traumatic to the heart wall and the RCA. In other words, the angle α of the posterior anchoring flap 390' makes the the posterior anchoring flap 390' conform more closely to the natural anatomical topography of the posterior section of the RV (behind the posterior leaflet of the tricuspid valve) where the posterior anchoring flap 390' ultimately resides. This also serves to mitigate the potential for causing restrictions to the RCA.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Although a number of implementations have been described in detail above, other modifications are possible. For example, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A prosthetic tricuspid valve comprising:
   a main body comprising an occluder having valve leaflets;
   a first anterior flap extending laterally from an end of the main body; and
   a second anterior flap extending laterally from the end of the main body in a same direction as the first anterior flap,
   wherein portions of the first anterior flap and the second anterior flap overlap each other when the prosthetic tricuspid valve is deployed, and
   wherein having the portions of the first anterior flap and the second anterior flap that overlap each other increases a bending resistance of the first anterior flap and the second anterior flap in combination as compared to the first anterior flap and the second anterior flap individually.

2. The prosthetic tricuspid valve of claim 1, further comprising a posterior flap extending laterally from the end of the main body in an opposite direction as the first and second anterior flaps.

3. The prosthetic tricuspid valve of claim 2, wherein the first and second anterior flaps extend farther laterally than the posterior flap.

4. The prosthetic tricuspid valve of claim 3, wherein the first and second anterior flaps in combination are wider than the posterior flap.

5. The prosthetic tricuspid valve of claim 2, wherein a framework of the prosthetic tricuspid valve that comprises the main body, the first and second anterior flaps, and the posterior flap is made of a single, unitary material that was cut and expanded.

6. The prosthetic tricuspid valve of claim 2, wherein a distal tip portion of the posterior flap extends along an axis that is at a non-zero angle relative to a portion of the posterior flap that extends directly from the main body.

7. The prosthetic tricuspid valve of claim 1, wherein having the portions of the first anterior flap and the second anterior flap as separate members configure the prosthetic tricuspid valve to have a pacemaker lead pass through the prosthetic tricuspid valve between the first and second anterior flaps.

8. The prosthetic tricuspid valve of claim 1, further comprising one or more additional anterior flaps extending laterally from the end of the main body in the same direction as the first and second anterior flaps.

9. The prosthetic tricuspid valve of claim 1, further comprising two or more posterior flaps extending laterally from the end of the main body in an opposite direction as the first and second anterior flaps.

10. The prosthetic tricuspid valve of claim 1, further comprising a deployment system comprising:
a sheath catheter defining a first lumen;
an outer proximal catheter slidably disposed within the first lumen and defining a second lumen; and
an inner distal catheter slidably disposed within the second lumen,
wherein the prosthetic tricuspid valve is disposed within the first lumen in a low profile delivery configuration and is releasably attached to both the outer proximal catheter and the inner distal catheter.

11. The prosthetic tricuspid valve of claim 10, wherein the main body is releasably attached to outer proximal catheter, and wherein the first and second anterior flaps are releasably attached to the inner distal catheter.

12. The prosthetic tricuspid valve of claim 11, wherein the prosthetic tricuspid valve further comprises a posterior flap extending laterally from the end of the main body in an opposite direction as the first and second anterior flaps, and wherein the posterior flap is disposed within the first lumen while not being directly attached to the deployment system.

13. The prosthetic tricuspid valve of claim 11, wherein the first and second anterior flaps are individually releasably attached to the inner distal catheter.

14. A prosthetic tricuspid valve comprising:
a main body comprising an occluder having valve leaflets;
a first anterior flap extending laterally from an end of the main body; and
a second anterior flap extending laterally from the end of the main body in a same direction as the first anterior flap,
wherein having the portions of the first anterior flap and the second anterior flap as separate members configure the prosthetic tricuspid valve to have a pacemaker lead pass through the prosthetic tricuspid valve between the first and second anterior flaps.

15. The prosthetic tricuspid valve of claim 14, wherein portions of the first anterior flap and the second anterior flap overlap each other.

16. The prosthetic tricuspid valve of claim 15, wherein having the portions of the first anterior flap and the second anterior flap that overlap each other increases a bending resistance of the first anterior flap and the second anterior flap in combination as compared to the first anterior flap and the second anterior flap individually.

17. The prosthetic tricuspid valve of claim 14, further comprising a posterior flap extending laterally from the end of the main body in an opposite direction as the first and second anterior flaps.

18. The prosthetic tricuspid valve of claim 17, wherein the first and second anterior flaps in combination are wider than the posterior flap.

19. A prosthetic tricuspid valve comprising:
a main body comprising an occluder having valve leaflets;
a first anterior flap extending laterally from an end of the main body;
a second anterior flap extending laterally from the end of the main body in a same direction as the first anterior flap; and
two or more posterior flaps extending laterally from the end of the main body in an opposite direction as the first and second anterior flaps.

20. The prosthetic tricuspid valve of claim 19, wherein portions of the first anterior flap and the second anterior flap overlap each other.

21. The prosthetic tricuspid valve of claim 20, wherein having the portions of the first anterior flap and the second anterior flap that overlap each other increases a bending resistance of the first anterior flap and the second anterior flap in combination as compared to the first anterior flap and the second anterior flap individually.

22. The prosthetic tricuspid valve of claim 19, wherein having the portions of the first anterior flap and the second anterior flap as separate members configure the prosthetic tricuspid valve to have a pacemaker lead pass through the prosthetic tricuspid valve between the first and second anterior flaps.

* * * * *